US008778382B2

(12) United States Patent
Howard et al.

(10) Patent No.: US 8,778,382 B2
(45) Date of Patent: Jul. 15, 2014

(54) TAMPER RESISTANT TRANSDERMAL DOSAGE FORM

(75) Inventors: Stephen A. Howard, Danbury, CT (US); Bruce Reidenberg, Rye, NY (US)

(73) Assignee: Purdue Pharma L.P., Stamford, CT (US)

( * ) Notice: Subject to any disclaimer, the term of this patent is extended or adjusted under 35 U.S.C. 154(b) by 1214 days.

(21) Appl. No.: 10/835,535

(22) Filed: Apr. 30, 2004

(65) Prior Publication Data

US 2005/0002997 A1    Jan. 6, 2005

Related U.S. Application Data

(60) Provisional application No. 60/467,235, filed on Apr. 30, 2003, provisional application No. 60/467,243, filed on Apr. 30, 2003.

(51) Int. Cl.
A61K 9/00    (2006.01)
A61F 2/00    (2006.01)

(52) U.S. Cl.
USPC .......................................... 424/429; 424/427

(58) Field of Classification Search
CPC .. A61K 9/7023; A61K 9/7084; A61K 9/7092
See application file for complete search history.

(56) References Cited

U.S. PATENT DOCUMENTS

| | | |
|---|---|---|
| 1,602,344 A | 10/1926 | Eagle |
| 2,807,262 A | 9/1957 | Lew |
| 3,598,122 A | 8/1971 | Zaffaroni |
| 3,598,123 A | 8/1971 | Zaffaroni |
| 3,731,683 A | 5/1973 | Zaffaroni |
| 3,742,951 A | 7/1973 | Zaffaroni |
| 3,773,955 A | 11/1973 | Pachter et al. |
| 3,797,494 A | 3/1974 | Zaffaroni |
| 3,966,940 A | 6/1976 | Pachter et al. |
| 3,996,934 A | 12/1976 | Zaffaroni |
| 3,598,122 B1 | 11/1982 | Zaffaroni |
| 3,742,951 B1 | 11/1982 | Zaffaroni |
| 4,457,933 A | 7/1984 | Gordon et al. |
| 4,539,256 A | 9/1985 | Shipman |
| 4,573,995 A | 3/1986 | Chen et al. |
| 4,582,835 A | 4/1986 | Lewis et al. |
| 4,588,580 A | 5/1986 | Gale et al. |
| 4,588,580 B1 | 5/1986 | Gale et al. |
| 4,626,539 A | 12/1986 | Aungst et al. |
| 4,666,441 A | 5/1987 | Andriola et al. |
| 4,687,481 A * | 8/1987 | Nuwayser ..................... 424/449 |
| 4,693,776 A | 9/1987 | Krampe et al. |
| 4,743,249 A * | 5/1988 | Loveland ...................... 424/447 |
| 4,746,515 A | 5/1988 | Cheng et al. |
| 4,788,064 A | 11/1988 | Patel et al. |
| 4,806,341 A | 2/1989 | Chien et al. |
| 4,822,802 A | 4/1989 | Levy et al. |
| 4,839,174 A | 6/1989 | Baker et al. |
| 4,879,297 A | 11/1989 | Mahjour et al. |
| 4,906,463 A | 3/1990 | Cleary et al. |
| 4,917,688 A | 4/1990 | Nelson et al. |
| 4,954,343 A | 9/1990 | Hosaka et al. |
| 4,960,467 A | 10/1990 | Peck |
| 4,971,799 A | 11/1990 | Nakagawa et al. |
| 4,978,532 A | 12/1990 | El-Rashidy |
| 4,994,267 A | 2/1991 | Sablotsky |
| 5,032,403 A | 7/1991 | Sinnreich |
| 5,032,637 A | 7/1991 | Therriault et al. |
| 5,053,227 A | 10/1991 | Chiang et al. |
| 5,066,494 A | 11/1991 | Becher |
| 5,120,546 A | 6/1992 | Hansen et al. |
| 5,123,900 A * | 6/1992 | Wick ................................ 602/41 |
| 5,132,115 A * | 7/1992 | Wolter et al. .................. 424/448 |
| 5,149,538 A | 9/1992 | Granger et al. |
| 5,149,719 A | 9/1992 | Ferber et al. |
| 5,176,917 A * | 1/1993 | Muller ........................... 424/448 |
| 5,185,329 A | 2/1993 | Gawin et al. |
| 5,186,939 A | 2/1993 | Cleary et al. |
| 5,236,714 A | 8/1993 | Lee et al. |
| 5,264,219 A | 11/1993 | Godbey et al. |
| 5,306,503 A | 4/1994 | Müller et al. |
| 5,342,623 A | 8/1994 | Enscore et al. |
| 5,344,656 A | 9/1994 | Enscore et al. |
| 5,352,457 A | 10/1994 | Jenkins |
| 5,352,516 A | 10/1994 | Therriault et al. |
| 5,372,819 A | 12/1994 | Godbey et al. |

(Continued)

FOREIGN PATENT DOCUMENTS

DE    35 26 339 A1    1/1986
DE    35 46 830 C2    1/1986

(Continued)

OTHER PUBLICATIONS

Peterson et al. "Design, development, manufacturing, and testing of transdermal delivery systems" In Transdermal and Topical Drug Delivery Systems Ed. Ghosh, Pfister, and Yum. Taylor and Francis:Boca Raton, 1997 pp. 249-277.*
Ahmedzai, S., et al., "Transdermal Fentanyl verus Sustained-Release Oral Morphine in Cancer Pain: Preference, Efficacy and Quality of Life," *J. Pain Symptom Mgmt.*. 13:254-261, Elsevier (1997).
Allan, L., et al., "Randomised Crossover Trial of Transdermal Fentanyl and Sustained Release Oral Morphine for Treating Chronic Non-Cancer Pain," *BMJ* 322: 1-7, BMJ Publishing Group (2001).
Alsahaf, M.H., and Stockwell, M., "Respiratory Failure Due to the Combined Effects of Transdermal Fentanyl and Epidural Bupivacaine/Diamorphine Following Radical Nephrectomy," *J. Pain Symptom Mgmt.* 20:210-213, Elsevier (2000).
Anderson, D.T., and Muto, J.J., "Duragesic Transdermal Patch: Postmortem Tissue Distribution of Fentanyl in 25 Cases," *J. Anal. Toxicol.* 24:627-634, Preston Publications (2000).

(Continued)

*Primary Examiner* — Juliet Switzer
*Assistant Examiner* — Caralynne Helm
(74) *Attorney, Agent, or Firm* — Sterne, Kessler, Goldstein & Fox P.L.L.C.

(57) ABSTRACT

The invention comprises a transdermal dosage form comprising an active agent component comprising an active agent and an adverse agent component comprising an adverse agent, wherein the active agent component defines at least one channel extending substantially there through.

20 Claims, 41 Drawing Sheets

(56) References Cited

U.S. PATENT DOCUMENTS

| | | | |
|---|---|---|---|
| 5,395,907 A | 3/1995 | Zajaczkowski | |
| 5,462,743 A * | 10/1995 | Turner et al. | 424/448 |
| 5,462,745 A | 10/1995 | Enscore et al. | |
| 5,474,783 A | 12/1995 | Miranda et al. | |
| 5,494,680 A | 2/1996 | Peterson | |
| 5,508,367 A | 4/1996 | Zajaczkowski | |
| 5,518,734 A | 5/1996 | Stefano et al. | |
| 5,536,263 A | 7/1996 | Rolf et al. | |
| 5,565,268 A | 10/1996 | Zajaczkowski | |
| 5,573,778 A | 11/1996 | Therriault et al. | |
| 5,585,111 A | 12/1996 | Peterson | |
| 5,589,480 A | 12/1996 | Elkhoury et al. | |
| 5,633,009 A | 5/1997 | Kenealy et al. | |
| 5,703,169 A | 12/1997 | Zajaczkowski et al. | |
| 5,703,170 A | 12/1997 | Zajaczkowski et al. | |
| 5,705,185 A | 1/1998 | Stefano et al. | |
| 5,733,571 A | 3/1998 | Sackler | |
| 5,741,510 A | 4/1998 | Rolf et al. | |
| 5,750,134 A | 5/1998 | Scholz et al. | |
| 5,750,136 A | 5/1998 | Scholz et al. | |
| 5,756,117 A | 5/1998 | D'Angelo et al. | |
| 5,762,952 A | 6/1998 | Barnhart et al. | |
| 5,783,583 A | 7/1998 | Simon | |
| 5,788,983 A | 8/1998 | Chien et al. | |
| 5,804,215 A | 9/1998 | Cubbage et al. | |
| 5,814,032 A | 9/1998 | Hori et al. | |
| 5,817,331 A | 10/1998 | Kenealy et al. | |
| 5,837,280 A | 11/1998 | Kenealy et al. | |
| 5,840,327 A * | 11/1998 | Gale et al. | 424/448 |
| 4,588,580 B2 | 2/1999 | Gale et al. | |
| 5,866,143 A | 2/1999 | Elkhoury | |
| 5,866,157 A | 2/1999 | Higo et al. | |
| 5,866,164 A | 2/1999 | Kuczynski et al. | |
| 5,912,009 A | 6/1999 | Venkateshwaran et al. | |
| 5,951,999 A | 9/1999 | Therriault et al. | |
| 5,958,446 A | 9/1999 | Miranda et al. | |
| 5,968,547 A | 10/1999 | Reder et al. | |
| 5,972,954 A | 10/1999 | Foss et al. | |
| 5,976,547 A | 11/1999 | Archer et al. | |
| 5,981,666 A | 11/1999 | Zajaczkowski et al. | |
| 5,985,317 A | 11/1999 | Venkateshwaran et al. | |
| 5,993,849 A | 11/1999 | Assmus et al. | |
| 6,004,578 A | 12/1999 | Lee et al. | |
| 6,018,092 A | 1/2000 | Dunshee | |
| 6,063,399 A | 5/2000 | Assmus et al. | |
| 6,063,838 A | 5/2000 | Patnode et al. | |
| 6,093,419 A | 7/2000 | Rolf | |
| 6,103,258 A * | 8/2000 | Simon | 424/449 |
| 6,123,890 A | 9/2000 | Mazurek et al. | |
| 6,129,929 A | 10/2000 | Wick | |
| 6,132,760 A | 10/2000 | Hedenstrom et al. | |
| 6,136,807 A | 10/2000 | Braun | |
| 6,143,278 A | 11/2000 | Elkhoury | |
| 6,159,497 A | 12/2000 | LaPrade et al. | |
| 6,165,499 A | 12/2000 | Kleinsorgen et al. | |
| 6,174,546 B1 | 1/2001 | Therriault et al. | |
| 6,183,770 B1 | 2/2001 | Muchin et al. | |
| 6,193,996 B1 | 2/2001 | Effing et al. | |
| 6,228,863 B1 | 5/2001 | Palermo et al. | |
| 6,231,885 B1 | 5/2001 | Carrara | |
| 6,239,228 B1 | 5/2001 | Zajaczkowski et al. | |
| 6,264,979 B1 * | 7/2001 | Svedman | 424/449 |
| 6,277,384 B1 | 8/2001 | Kaiko et al. | |
| 6,294,038 B1 * | 9/2001 | Majkrzak | 156/238 |
| 6,299,899 B1 | 10/2001 | Von Kleinsorgen | |
| 6,326,027 B1 | 12/2001 | Miller et al. | |
| 6,344,212 B2 | 2/2002 | Reder et al. | |
| 6,348,210 B1 | 2/2002 | Gale | |
| 6,362,194 B1 | 3/2002 | Crain et al. | |
| 6,365,178 B1 * | 4/2002 | Venkateshwaran et al. | 424/449 |
| 6,375,957 B1 | 4/2002 | Kaiko et al. | |
| 6,475,494 B2 | 11/2002 | Kaiko et al. | |
| 6,569,866 B2 | 5/2003 | Simon | |
| 6,627,635 B2 | 9/2003 | Palermo et al. | |
| 6,696,066 B2 | 2/2004 | Kaiko et al. | |
| 6,696,088 B2 | 2/2004 | Oshlack et al. | |
| 6,787,149 B1 | 9/2004 | El Khoury et al. | |
| 6,796,429 B2 | 9/2004 | Cameron et al. | |
| 6,806,294 B2 | 10/2004 | Wimmer et al. | |
| 6,867,342 B2 | 3/2005 | Johnston et al. | |
| 6,893,655 B2 | 5/2005 | Flanigan et al. | |
| 7,182,955 B2 | 2/2007 | Hart et al. | |
| 2002/0037313 A1 | 3/2002 | Simon | |
| 2002/0106329 A1 | 8/2002 | Leslie | |
| 2002/0110585 A1 * | 8/2002 | Godbey et al. | 424/449 |
| 2002/0119187 A1 | 8/2002 | Cantor et al. | |
| 2002/0198215 A1 | 12/2002 | Tavares et al. | |
| 2003/0004177 A1 | 1/2003 | Kao et al. | |
| 2003/0026829 A1 | 2/2003 | Venkatraman et al. | |
| 2003/0035828 A1 | 2/2003 | Tavares et al. | |
| 2003/0064122 A1 | 4/2003 | Goldberg et al. | |
| 2003/0065002 A1 | 4/2003 | Caruso et al. | |
| 2003/0069263 A1 | 4/2003 | Breder et al. | |
| 2003/0072791 A1 | 4/2003 | Tavares et al. | |
| 2003/0075470 A1 | 4/2003 | Cameron et al. | |
| 2003/0130314 A1 | 7/2003 | Druzgala | |
| 2003/0181475 A1 | 9/2003 | Kaiko et al. | |
| 2003/0181516 A1 | 9/2003 | Krylov et al. | |
| 2004/0013716 A1 * | 1/2004 | Gale et al. | 424/449 |
| 2004/0033253 A1 | 2/2004 | Shevchuk et al. | |
| 2004/0033255 A1 | 2/2004 | Baker et al. | |
| 2004/0043171 A1 * | 3/2004 | Audett | 428/35.7 |
| 2004/0081685 A1 | 4/2004 | Wright, IV | |
| 2004/0109886 A1 * | 6/2004 | Rigby | 424/449 |
| 2004/0122554 A1 | 6/2004 | Howard | |
| 2004/0126323 A1 * | 7/2004 | Shevchuk et al. | 424/10.1 |
| 2004/0126416 A1 | 7/2004 | Reidenberg et al. | |
| 2004/0126417 A1 | 7/2004 | Reidenberg et al. | |
| 2004/0146547 A1 | 7/2004 | Marcenyac et al. | |
| 2004/0152689 A1 | 8/2004 | Chen | |
| 2004/0202708 A1 | 10/2004 | Roehrig et al. | |
| 2004/0219195 A1 | 11/2004 | Hart et al. | |
| 2004/0219196 A1 | 11/2004 | Hart et al. | |
| 2004/0219198 A1 | 11/2004 | Johnson et al. | |
| 2004/0228917 A1 | 11/2004 | Oshlack et al. | |
| 2004/0241218 A1 * | 12/2004 | Tavares et al. | 424/449 |
| 2005/0025794 A1 | 2/2005 | Wang et al. | |
| 2005/0031678 A1 | 2/2005 | Tavares et al. | |
| 2005/0063909 A1 | 3/2005 | Wright, IV et al. | |
| 2005/0191340 A1 | 9/2005 | Bartholomaeus et al. | |
| 2006/0198881 A1 | 9/2006 | Howard et al. | |
| 2010/0068249 A1 | 3/2010 | Hart et al. | |

FOREIGN PATENT DOCUMENTS

| | | |
|---|---|---|
| EP | 0 441 833 | 8/1991 |
| EP | 1 64 1441 A2 | 4/2006 |
| GB | 2 165 148 A | 4/1986 |
| JP | 2006-525315 A | 11/2006 |
| JP | 2006-525316 A | 11/2006 |
| WO | WO 97/04835 | 2/1997 |
| WO | WO 99/15156 | 4/1999 |
| WO | WO 99/40903 | 8/1999 |
| WO | WO 00/01377 A2 | 1/2000 |
| WO | WO 00/51575 | 9/2000 |
| WO | WO 01/26705 | 4/2001 |
| WO | WO 02/26217 | 4/2002 |
| WO | WO 02/054996 | 7/2002 |
| WO | WO 02/074286 | 9/2002 |
| WO | WO 02/085268 | 10/2002 |
| WO | WO 02/087482 | 11/2002 |
| WO | WO 02/092059 A1 | 11/2002 |
| WO | WO 02/092060 A1 | 11/2002 |
| WO | WO 02/094172 A1 | 11/2002 |
| WO | WO 02/094173 A2 | 11/2002 |
| WO | WO 02/094174 | 11/2002 |
| WO | WO 03/013433 A2 | 2/2003 |
| WO | WO 03/013525 A1 | 2/2003 |
| WO | WO 03/034961 | 6/2003 |
| WO | WO 03/070191 | 8/2003 |
| WO | WO 03/090729 | 11/2003 |
| WO | WO 03/103673 | 12/2003 |
| WO | WO 2004/014336 | 2/2004 |
| WO | WO 2004/017941 | 3/2004 |

(56) References Cited

FOREIGN PATENT DOCUMENTS

| WO | WO 2004/098567 A2 | 11/2004 |
|---|---|---|
| WO | WO2004/098568 A2 | 11/2004 |
| WO | WO2004/098576 A1 | 11/2004 |

OTHER PUBLICATIONS

Bernstein, K.J., and Klausner, M.A., "Potential Dangers Related to Transdermal Fentanyl (Duragesic®) When Used for Postoperative Pain," *Dis. Colon Rectum*. 37:1339-1340, Springer Verlag (1994).
Bloor, K., et al., "The Costs of Managing Severe Cancer Pain and Potential Savings from Transdermal Administration," *Eur. J. Cancer* 30A:463-468, Elsevier Science Ltd. (1994).
Calis, K.A., et al., "Transdermally Administered Fentanyl for Pain Management," *Clin. Pharm*. 11:22-36, American Society of Hospital Pharmacists (1992).
Cassidy, J.P., "Controlled Buccal Delivery of Buprenorphine," *J. Controlled Release* 25:21-29, Elsevier Science Publishers B. V. (1993).
Cleary, G.W., "Transdermal Drug Delivery," *Cosmetics & Toiletries* 106:97-109, Allured Publishing Corp. (1991).
Collins, J.J., et al., "Transdermal Fentanyl in Children with Cancer Pain: Feasibility, Tolerability, and Pharmacokinetic Correlates," *J. Pediatr*. 134:319-323, Mosby-Year Book (1999).
Coluzzi, P.H., at al., "Breakthrough Cancer Pain: A Randomized Trial Comparing Oral Transmucosal Fentany Citrate (OTFC®) and Morphine Sulfate Immediate Release (MSIR®)," *Pain* 91:123-130, Elsevier Science (2001).
Donner, B., et al., "Long-Term Treatment of Cancer Pain with Transdermal Fentanyl," *J. Pain Symptom Mgmt*. 15:168-175, Elsevier (1998).
Donner, B., et al., "Direct Conversion from Oral Morphine to Transdermal Fentanyl: A Multicenter Study in Patients with Cancer Pain," *Pain* 64:527-534, Elsevier Science B.V. (1996).
Edinboro, L.E., et al., "Fatal Fentanyl Intoxication Following Excessive Transdermal Application," *J. Forensic Sci*. 42:741-743, American Society for Testing and Materials (1997).
Fine, P.G., "Opioid Selection: Plaudits, Pitfalls, and Possibilities," *J. Pain* 2:195-196, Churchill Livingstone (2001).
Flannagan, L.M., et al., Fentanyl Patches Left on Dead Bodies—Potential Source of Drug for Abusers, *J. Forensic Sci*. 41:320-321, American Society for Testing and Materials (1996).
Fudin, J., et al., "Quicker Dosage Adjustment for Transdermal Fentanyl,"*Am. J. Health Syst. Pharm*. 54:87-88, American Society of Health-System Pharmacists (1997).
Gal, T.J., and DiFazio, C.A., "Prolonged Antagonism of Opioid Action with Intravenous Nalmefene in Man," *Anesthesiology* 64:175-180, J.B. Lippincott Co. (1986).
Grond, S., et al., "Clinical Pharmacokinetics of Transdermal Opioids," *Clin. Pharmacokinet*. 38:59-89, Adis International Ltd. (2000).
Grond, S. et al., "Fentanyl Transdermal in Long-Term Treatment of Cancer Pain: A Prospective Study of 50 Patients with Advanced Cancer of GI Tract or Head/Neck," *Pain* 69:191-198, Elsevier Science (1997).
Harvey-Clark, C.J., at al., "Transdermal Fentanyl Compared with Parenteral Buprenorphine in Post-Surgical Pain in Swine: A Case Study," *Lab. Anim*. 34:386-398, Royal Society of Medicine Services Ltd (2000).
Joranson, D.E., et al.,"Trends in Medical Use and Abuse of Opioid Analgesics," *JAMA* 283:1710-1714, American Medical Association (2000).
Korte, W., and Morant, R., "Transdermal Fentanyl in Uncontrolled Cancer Pain: Titration on a Day-to-Day Basis as a Procedure for Safe and Effective Dose Finding—A Pilot Study in 20 Patients," *Supportive Care Cancer* 2:123-127, Springer-Verlag Heidelberg (1994).
Korte, W. et al., "Day to Day Titration to Initiate Fentanyl Transdermal in Patients with Cancer Pain: Short- and Long-term Experiences in a Prospective Study with 39 Patients," *J. Pain & Symptom Mgmt*. 11:139-146, Elsevier (1996).

Lossingol, D., et al., "Fentanyl TTS in Cancer Pain," *J. Pain & Symptom Mgmt*. 15:S16, Elsevier, Abstract No. 47 (1998).
Marquardt, K.A., et al., "Fentanyl Remaining in a Transdermal System Following Three Days of Continuous Use," *Ann. Pharmacother*. 29:969-971, Harvey AK Whitney (1995).
Mason, B.J., at al., "A Double-blind, Placebo-Controlled Study of Oral Nalmefene for Alcohol Dependence," *Arch. Gen. Psychiatry* 56:719-724, American Medical Association (1999).
Medzon, R., "Naltrexone and Nalmefene," *Clin. Toxicol. Rev*. 19(3) (4 pages) Massachusetts Poison Control System (Dec. 1996), available at http://www.maripoisoncenter.com/ctr/9612naltrexone.html.
Miligan, K., et al., "Evaluation of Long-term Efficacy and Safety of Transdermal Fentanyl in the Treatment of Chronic Noncancer Pain," *J. Pain* 2:197-204, Churchill Livingstone (2001).
Mystakidou, K., et al., "From Codeine to Transdermal Fentanyl for Cancer Pain Control: A Safety and Efficacy Clinical Trial," *Anticancer Res*. 21:2225-2230, John Delinassios (2001).
Olmedo, R.E; et al., "Death as a Complication of Ultrarapid Opioid Detoxification," *J. Toxicol. Clin. Toxicol.*, 41:536-537, Dekkar, Abstract No. 81 (2000).
Payne, R., "Factors Influencing the Quality of Life in Cancer Patients: The Role of Transdermal Fentanyl in the Management of Pain," *Semin. Oncol*. 25 (suppl 7): 47-53, W. B. Sanders Co. (1998).
Payne, R., et al., "Quality of Life and Cancer Pain: Satisfaction and Side Effects with Transdermal Fentanyl versus Oral Morphine," *J. Clin. Oncol*. 16:1588-1593, American Society of Clinical Oncology (1998).
Portenoy, R.K., et al., "Transdermal Fentanyl for Cancer Pain," *Anesthesiology* 78:36-43, J.B. Lippincott Co. (1993).
Radvanyi, T., et al., "Antagonism of the Postoperative Respiratory Depression Caused by Large Doses of Morphine," *Anesthesiology* (Suppl.) 73 (3A), J.B. Lippincott Co., Abstract No. A1173 (1990).
Roberge, R.J., et al., "Transdermal Drug Delivery System Exposure Outcomes," *J. Emerg. Med*. 18:147-151, Elsevier Science Inc. (2000).
Roberts, M.S., et al., "Epidermal Permeability: Penetrant Structure Relationships. 2. The Effect of H-bonding Groups in Penetrants on their Diffusion Through Stratum Corneum," *Int. J. Pharm*. 132:23-32, Elsevier Science B.V. (1996).
Roy, S.D. at al., "Controlled Transdermal Delivery of Fentanyl: Characterizations of Pressure Sensitive Adhesives for Matrix Patch Design," *J. Pharm. Sci*. 85:491-495, American Chemical Society (1996).
Roy, S.D., et al., "Transdermal Delivery of Narcotic Analgesics: Comparative Metabolism and Permeability of Human Cadaver Skin and Hairless Mouse Skin," *J. Pharm. Sci*. 83:17231728, American Chemical Society (1994).
Sevarino, F.B., et al., "Post-Operative Analgesia with Parenteral Opioids: Does Continuous Delivery Utilizing a Transdermal Opioid Preparation Affect Analgesic Efficacy or Patient Safety?," *J. Clin. Anesth*. 9:173-178, Elsevier Science Inc. (1997).
Shah, V.P., et al., "In Vitro Dissolution Profile of Transdermal Nitroglycerin Patches Using Paddle Method,"*Int. J. Pharm*. 32:243-250, Elsevier Science Publishers B.V. (1986).
Simpson, R,K., et al., "Transdermal Fentanyl as Treatment for Chronic Low Back Pain," *J. Pain Symptom Mgmt*. 14:218-224, Elsevier (1997).
Sloan, P.A., et al., "A Clinical Evaluation of Transdermal Therapeutic System Fentanyl for the Treatment of Cancer Pain," *J. Pain Symptom Mgmt*. 16:102-111, Elsevier (1998).
Souders, C., et al., "Apnea from Fentanyl Patch Smoking," *J. Toxicol. Clin. Toxicol.*, 41: 536, Dekkar, Abstract No. 79 (2000).
Thompson, J.P., et al., "Perioperative Pharmacokinetics of Transdermal Fentanyl in Elderly and Young Adult Patients," *Br. J. Anaesth*. 81:152-154, Oxford University Press (1998).
Varvel, J.R., et al., "Absorption Characteristics of Transdermally Administered Fentanyl," *Anesthesiology* 70:928-934, Lippincott Williams & Williams (1989).
Wakefield, B., et al., "A Research-Based Guideline for Appropriate Use of Transdermal Fentanyl to Treat Chronic Pain," *Oncol. Nurs. Forum* 25:1505-1513, Oncology Nursing Society (1998).

(56) References Cited

OTHER PUBLICATIONS

Watanabe, S., et al., "Fentanyl by Continuous Subcutaneous Infusion for the Management of Cancer Pain: a Retrospective Study," *J. Pain Symptom Mgmt.* 16:323-326, Elsevier (1998).

Yeo, W., et al., "Transdermal Fentanyl for Severe Cancer-Related Pain," *Palliat. Med.* 11:233-239, Arnold (1997).

Dialog File 351, Accession No. 16056581, Derwent WPI English language abstract for WO 2004/014336.

Office Action for U.S. Appl. No. 11/281,884, Howard et al., mailed Apr. 9, 2009.

European Search Report for EP Application No. 04751 268.6, Munich, Germany, completed on Jun. 12, 2009 (4 pages).

Office Action for U.S. Appl. No. 11/281,884, Stephen A. Howard et al., mailed May 20, 2010.

Office Action for U.S. Appl. No. 12/621,595, Hart et al., mailed Apr. 18, 2012 (24 pages).

Office Action for U.S. Appl. No. 11/281,884, Howard et al., mailed Dec. 5, 2012 (21 pages).

Defective Notice of Appeal for U.S. Appl. No. 12/621,595, Hart et al., mailed Mar. 7, 2013 (2 pages).

Dialog File 351, Accession No. 4469393, WPI English language abstract for DE 35 26 339 A1 (Document FP1 on accompanying Form PTO/SB/08A) and DE 35 46 830 C2 (Document FP2 on accompanying Form PTO/SB/08A), 2005.

International Search Report for International Application No. PCT/US2004/013810, European Patent Office, Netherlands, mailed on Nov. 22, 2004.

Written Opinion of the International Searching Authority for International Application No. PCT/US2004/013810, European Patent Office, Munich, Germany, 2004.

European Examination Report for European Application No. 04 751 268, European Patent Office, Munich, Germany, 2007.

Alan S. Nies & Stephen P. Spielberg, in Goodman & Gilman's Pharmacological Basis of Therapeutics, Chapter 3, pp. 43-62 ($9^{th}$ ed., Interamericana, Mexico 1996).

3M Drug Delivery Systems, "Transdermal Drug Delivery: Get the edge in a competitive environment," (Sep. 2001), 11 pages.

"3M Drug Delivery Systems and Purdue Pharma to Develop Seven-Day Analgesic Using Novel Transdermal Delivery System," PR Newswire Association LLC (Jan. 9, 2001), downloaded from http://www.thefreelibrary.com/_/print/PrintArticle.aspx?id=68911600, 2 pages.

Office Action for U.S. Appl. No. 11/281,884, Howard et al., mailed Feb. 1, 2011 (29 pages).

Office Action for U.S. Appl. No. 12/621,595, Hart et al., mailed Jul. 20, 2011 (21 pages).

\* cited by examiner

TAMPER RESISTANT TRANSDERMAL DOSAGE FORM

BACKGROUND OF THE INVENTION

1. Field of the Invention

The present invention relates to transdermal dosage forms which are useful for preventing or discouraging tampering, abuse, misuse or diversion of a dosage form containing an active pharmaceutical agent, such as an opioid. The present invention also relates to methods of treating a patient with such a dosage form. The application claims the benefit of U.S. Provisional Application No. 60/467,235, filed Apr. 30, 2003, and U.S. Provisional Application No. 60/467,243, filed Apr. 30, 2003, both of which are herein incorporated by reference in their entireties.

2. Background of the Invention

Transdermal drug delivery is a well known method for administering pharmaceuticals. Although a transdermal dosage form is intended to deliver drug across the skin, misuse or abuse of such a dosage form can take place by other modes, including oral, buccal, and intravenous. Such misuse may take place following an extraction procedure comprising immersing the transdermal dosage form in a solvent, such as water, alcohol, ethanol, or ether.

Transdermal dosage forms comprising both a drug and an antagonist for the drug have been previously proposed. U.S. Pat. No. 5,236,714 (Lee et al.) describes a transdermal dosage form which comprises a mixture of a drug and an antagonist for the drug. U.S. Pat. No. 5,149,538 (Granger, et al.) describes a transdermal dosage form comprising an opioid, an antagonist for the opioid releasable upon ingestion or solvent immersion of the dosage form, and a barrier means and an impermeable barrier means separating the opioid and the antagonist.

There exists a need in the art for improved designs for transdermal dosage forms which provide for the enhanced release of the adverse agent upon exposure of the dosage form to solvents, such as water, alcohol or ether.

SUMMARY OF THE INVENTION

In one embodiment, the present invention relates to a transdermal dosage form comprising an active agent-containing component (an "active agent component") having a proximal surface and a distal surface, and an adverse agent-containing component (an "adverse agent component") disposed distally of the active agent component, wherein the active agent component defines at least one channel extending substantially from the proximal surface to the distal surface.

In one embodiment, the present invention comprises a transdermal dosage form comprising an active agent component comprising a polymeric material and an active agent, an adverse agent component comprising an adverse agent, and a barrier disposed between the active agent component and the adverse agent component. The active agent component has a proximal surface, a distal surface, and at least one active agent component channel passing between the proximal and distal surfaces. The barrier is disposed between the distal surface of the active agent component and the adverse agent component. The barrier at least partially dissolves in the presence of and/or is permeable to many solvents, such as water, ethanol, ether, and mixtures thereof, and the barrier is impermeable to diffusion of the active agent and the adverse agent in the absence of a suitable solvent. In one embodiment, the transdermal dosage form further comprises an adhesive component connecting the adverse agent component and the barrier.

In another embodiment, the present invention comprises a transdermal dosage form comprising an active agent component comprising a polymeric material and an active agent, an adverse agent component comprising an adverse agent, and a discontinuous barrier. The active agent component defines at least one active agent component channel passing substantially through the active agent component. The discontinuous barrier is interposed between the active agent component and the adverse agent component. The barrier material is impermeable to diffusion of the active agent and the adverse agent.

In still another embodiment, the present invention comprises a transdermal dosage form comprising a skin-contacting component comprising a polymeric material and an active agent, a backing, and a reservoir component comprising an adverse agent. The skin-contacting component has a first skin-contacting surface and a second surface opposed to the skin-contacting surface. The reservoir component is interposed between the skin-contacting component and the backing. The adverse agent in the reservoir component is not in diffusional communication with the skin-contacting component. The active agent in the skin-contacting component is not in diffusional communication with the reservoir component. The dosage form comprises at least one channel passing between the skin-contacting surface and the reservoir component.

In certain embodiments, the present invention relates to a transdermal dosage form comprising an active agent component comprising an active agent and having a proximal surface and a distal surface, an adverse agent component comprising an adverse agent, wherein the adverse agent component is disposed distally of the distal surface of the active agent component, and at least one means for providing fluid communication between the proximal surface of the active agent component and the adverse agent component.

In one embodiment, the present invention relates to a transdermal dosage form comprising an active agent component comprising a plurality of structured active agent elements comprising a polymeric material and an active agent, wherein the structured active agent elements have a first, skin-contacting surface and a second surface opposed thereto, and adverse agent component comprising an adverse agent, and, a barrier disposed between the active agent component and the adverse agent component, wherein the barrier is impermeable to diffusion of active agent and adverse agent, and wherein the barrier extends to and abuts the first, skin-contacting surface of the structured active agent elements at points in between neighboring structure active agent elements.

In certain embodiments, the present invention relates to a transdermal dosage form comprising an active agent-containing component (an "active agent component"), an adverse agent-containing component (an "adverse agent component"), and a porous material adjacent to a portion of the adverse agent component.

In one embodiment, the present invention relates to a transdermal dosage form comprising an active agent component comprising an active agent, wherein the active agent component has a proximal surface and a distal surface opposed to the proximal surface, an overlay backing, an adverse agent component comprising an adverse agent, wherein the adverse agent component is interposed between the distal surface of the active agent component and the overlay backing, and a porous material adjacent to the adverse agent component, wherein the porous material is in fluid communication with the proximal surface of the active agent component.

In one embodiment, the invention relates to a transdermal dosage form comprising a release liner, an overlay backing, an active agent component interposed between the release liner and the overlay backing, wherein the active agent is in diffusional communication with the release liner, a barrier interposed between the active agent component and the overlay backing, an adverse agent component comprising an adverse agent, wherein the adverse agent component is interposed between the barrier and the overlay backing, and a porous material adjacent to the adverse agent component, wherein the porous material is in fluid communication with the release liner.

In certain embodiments, the present invention comprises a transdermal dosage form comprising an active agent component comprising a polymeric material and an active agent, an adverse agent component or reservoir comprising an adverse agent and a porous material or medium adjacent to the adverse agent component. In one embodiment, the porous medium is in fluid communication with a portion of the active agent component. In one embodiment, the adverse agent component is interposed between the active agent component and the backing.

In one embodiment, at least a portion of the adverse agent is contained within a porous medium. In another embodiment, the invention further comprises a barrier component adjacent to the distal surface of the active agent component. In still another embodiment, the porous medium comprises a polymeric film.

In certain embodiments, the present invention relates to a transdermal dosage form comprising an active agent component comprising an active agent, an adverse agent component comprising an adverse agent and disposed distally of the active agent component, and means for providing capillary force to a surface of the adverse agent layer in the presence of a liquid In certain embodiments, the present invention provides a transdermal dosage form that is resistant to tampering through extraction of the active agent from the dosage form by the incorporation of an adverse agent which is also extracted during such tampering. Such extraction may be performed, for example, in vitro, such as in a laboratory type setting (e.g., by complete immersion of the dosage form in a solvent or by surface extraction of an abusable substance from the active agent component), it should also be understood that extraction of adverse agent and active agent may also take place in vivo, such as in the saliva present in the oral cavity or the gastric fluid present in the stomach after ingestion.

In certain embodiments, the present invention provides a tamper-resistant transdermal dosage form that comprises an adverse agent for an active agent, wherein a significant amount of the adverse agent is not delivered to the skin mucosa surface during intended use, but wherein a sufficient amount of the adverse agent will be released from the dosage form along with the active agent during attempted tampering to blunt or block at least one biological effect of the active agent, such as euphoric effect of an opioid active agent, or to produce one or more unpleasant physiological reactions, such as nausea.

The present invention further relates to methods of treating a patient, comprising applying a dosage form of the invention to the skin or mucosa of a patient. In one embodiment of the invention, the patient is treated for pain.

The present invention also includes a method of reducing abuse, misuse or diversion of a dosage form for treating pain, comprising applying a dosage form of the invention to the skin or mucosa of a patient in need thereof.

In still another embodiment, the invention relates to a kit for treating pain in a patient, comprising at least one dosage form of the invention and a set of instructions describing the use of the dosage form to treat the patient. In one embodiment of the invention, the kit is for treating a patient's pain.

The present invention may be understood more fully by reference to the following detailed description and examples, which are intended to exemplify non-limiting embodiments of the invention. The above summary of the present invention is not intended to describe each disclosed embodiment or every implementation of the present invention.

BRIEF DESCRIPTION OF THE DRAWINGS

Certain embodiments of the invention will now be described in greater detail below with reference to the attached drawings, wherein.

DETAILED DESCRIPTION OF THE INVENTION

Definitions

Figure 1:
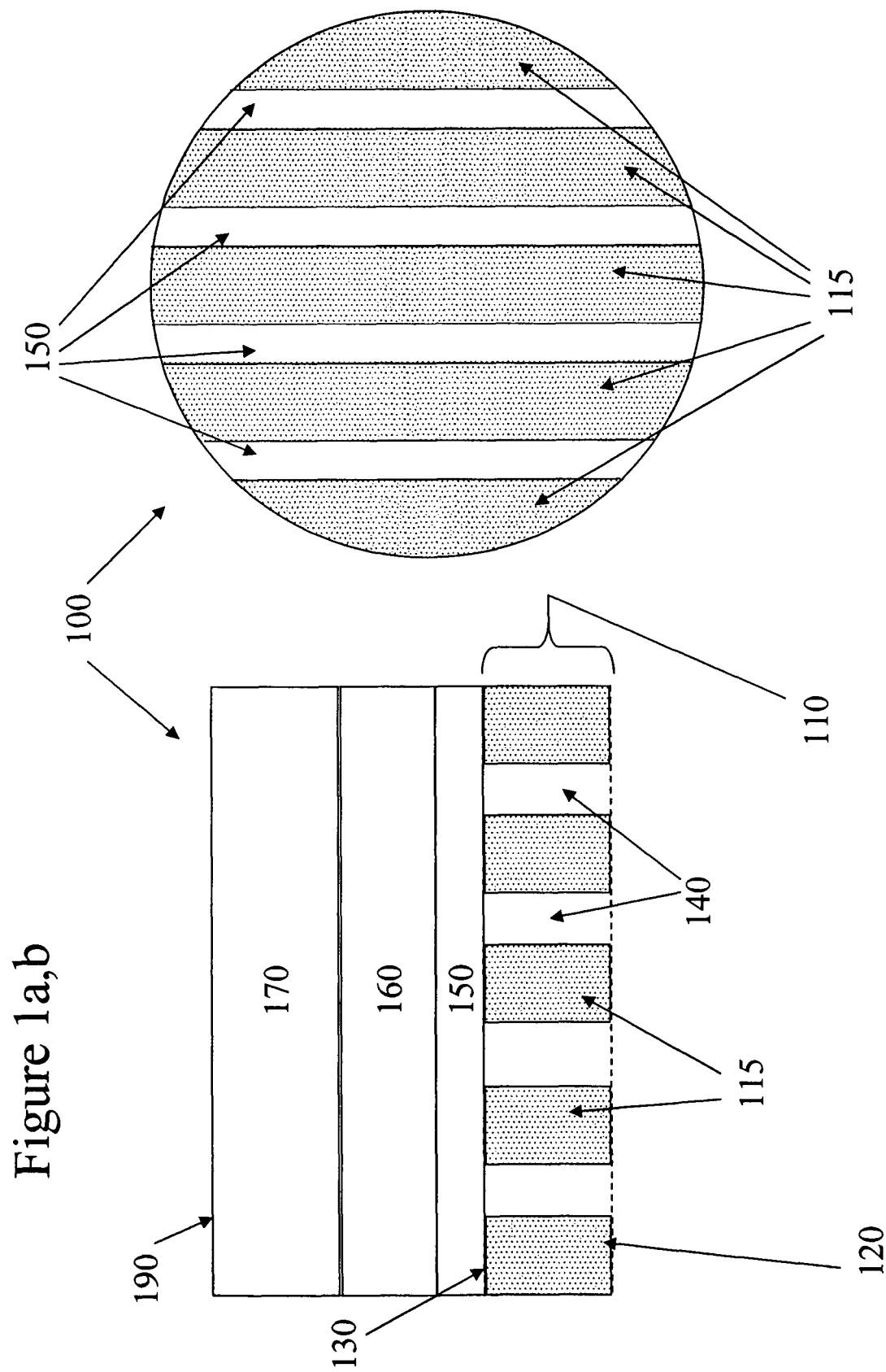
FIGS. 1a, b show a schematic cross-section (1a) and a plan view (1b) of an embodiment of the present invention where the skin-contacting component comprises strips separated by air channels.

The phrases "transdermal dosage form" and "dosage form", as used herein, refer to any dosage form that, when contacted with a patient's skin or mucosa for a sufficient period of time, can transdermally deliver an effective amount of any biologically active agent, such as a pharmaceutical agent, e.g., an opioid, through the patient's skin or mucosa. As used herein, the term "transdermal" refers to transdermal, transmucosal, buccal, sublingual, topical, rectal, and/or vaginal.

Any reference herein to any pharmaceutical agent, including but not limited to an active agent, an adverse agent, an opioid agonist or an opioid antagonist, shall, unless otherwise stated, include any pharmaceutically acceptable form of such pharmaceutical agent, such as the free form, any pharmaceutically acceptable salt form, any pharmaceutically acceptable base form, any pharmaceutically acceptable hydrate, any pharmaceutically acceptable solvate, any stereoisomer, any optical isomer, as well as any prodrug of such pharmaceutical agent and any pharmaceutically active analog of such pharmaceutical agent, and mixtures of any of the foregoing.

The phrase "pharmaceutically acceptable salt," as used herein, can be a salt formed from an acid and the basic group, such as a nitrogen group, of an active agent or an adverse agent. Generally, examples of such salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, glubionate and pamoate (i.e., 1,1'-methylene-bis-(2-hydroxy-3-naphthoate)) salts. The term "pharmaceutically acceptable salt" can alternatively be a salt prepared from an active agent or an adverse agent having an acidic functional group, such as a carboxylic acid or sulfonic acid functional group, and a pharmaceutically acceptable inorganic or organic base. Generally, examples of such bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

A "patient" or "animal" is preferably a mammal, and includes, but is not limited to, a cow, monkey, horse, sheep, pig, chicken, turkey, quail, cat, dog, mouse, rat, rabbit, and guinea pig, and most preferably a human.

The phrase "treatment of pain" or "treating pain" includes amelioration of pain or the cessation of pain or the avoidance of the onset of pain in a patient or animal.

As used herein, the phrase "active agent" refers to a pharmaceutical agent, drug, and/or agonist that causes a biological effect when absorbed into the blood stream of a patient.

As used herein, the phrase "adverse agent" refers to a pharmaceutical agent, drug, and/or antagonist that partially or completely prevents, negates, diminishes, delays or reverses at least one biological effect of the active agent present in the dosage form, e.g., euphoric effect, or produces one or more unpleasant physiological reactions, e.g., vomiting, nausea, diarrhea, bad taste, when absorbed in sufficient amount into the blood stream of a patient or animal.

As used herein, the phrase "opioid agonist" or "opioid" refers to an active agent which exhibits opium- or morphine-like properties when absorbed in sufficient amount into the blood stream of a patient. Opioid agonists bind, optionally stereospecifically, to any one or more of several subspecies of opioid receptors and produce agonist activity.

As used herein, the phrase "opioid antagonist" refers to an adverse agent that either partially or completely prevents, negates, diminishes, delays or reverses at least one biological effect of an opioid agonist, e.g., euphoric effect, when absorbed in sufficient amounts into the blood stream of a patient or animal.

As used herein, the phrase "channel" refers to a channel, conduit, aperture, pore, orifice, opening, space, void, gap, hole, crack, and/or slit.

As used herein, a "copolymer" includes a polymer comprising at least two different monomeric subunits. Thus, a polymeric chain made up of three different monomers (also known as a terpolymer) is included within the term "copolymer," as are polymer chains containing more than three different monomeric units.

As used herein, the phrase "dispersed" refers to dispersed, mixed, and/or dissolved either homogenously and/or heterogeneously.

As used herein, the phrase "component" refers to a layer, a stratum, a coating, a sheet, a film, a deposit, a sediment, a residue, and/or a cover.

As used herein, the term "proximal" refers to the location of a component, when considered as a whole, at a position which is relatively near to a site for application of the transdermal dosage form. The term "proximal surface" refers to the surface of a component which, when considered as a whole, is relatively near to a site for application of the transdermal dosage form, as compared to other surfaces of the component. In certain embodiments, the proximal surface of a component can be either continuous or discontinuous.

As used herein, the term "distal" refers to the location of a component, when considered as a whole, at a position which is relatively distant from a site for application of the transdermal dosage form. The term "distal surface" refers to the surface of a component which, when considered as a whole, is relatively distant from a site for application of the transdermal dosage form, as compared to other surfaces of the component. In certain embodiments, the proximal surface of a component can be either continuous or discontinuous.

As used herein, the term "opposed" as used with reference to two surfaces of a component refers to two surfaces which are generally facing in opposite directions regardless of whether one or both of the two surfaces are planar and/or parallel to each other.

As used herein, the terms "porous medium" and "porous material" are used interchangeably.

As used herein, the term skin-contacting" includes both "skin-contacting" and "mucosa-contacting".

Dosage Form

In one embodiment, shown in FIGS. 1a and 1b, the present invention comprises a transdermal dosage form 100 comprising an active agent-containing component 110 ("active agent component") comprising a polymeric material 115 and an active agent, an adverse-containing component 160 ("adverse agent component") comprising an adverse agent, and a barrier 150. The active agent component has a proximal surface 120, which may be a skin-contacting surface, a distal surface opposed to, i.e., opposite to or in contraposition to, the proximal surface 130, and channels 140 passing between the proximal and distal surfaces. The barrier 150 is disposed between the distal surface of the active agent component 130 and the adverse agent component 160. A backing 170 is disposed adjacent to the adverse agent component 160 at a location which provides an outer surface 190 of the dosage form 100.

As shown in FIGS. 1a and 1b, the active agent component 110 comprises a plurality of active agent strips 115 comprising a polymeric material and an active agent, wherein the active agent strips are separated to define channels 140 adjacent to the strips. In this embodiment, the channels 140 are filled with air or any inert gas. In one embodiment, the width of the active agent strips 115 is greater than about 0.1 cm. In another embodiment, the width of the active agent strips 115 is greater than about 0.2 cm. In another embodiment, the width of the active agent strips 115 is greater than about 0.4 cm. In another embodiment, the width of the strips comprising the skin-contacting polymeric matrix 115 and the active agent is less than about 2.0 cm. In another embodiment, the width of the strips comprising the skin-contacting polymeric matrix 115 and the active agent is less than 1.0 cm. In another embodiment, the width of the strips comprising the skin-contacting polymeric matrix 115 and the active agent is less than 0.6 cm.

In another aspect, as shown in FIGS. 2a and 2b, the active agent component 110, which may be a skin-contacting surface, consists of an annular disk comprising a polymeric material and an active agent which is configured to define a central channel 140 filled with air or any inert gas.

In still another aspect, as shown in FIGS. 3a and 3b, the active agent component 110 comprises a polymeric disk configured to define a plurality of cylindrical air channels 140. In one embodiment, the diameter of the cylindrical air channels 140 is greater than about 0.015 cm. In another embodiment, the diameter of the cylindrical air channels 140 is greater than about 0.05 cm. In another embodiment, the diameter of the cylindrical air channels 140 is greater than about 0.1 cm. In another embodiment, the diameter of the cylindrical air channels 140 is less than about 1.0 cm. In another embodiment, the diameter of the cylindrical air channels 140 is less than about 0.5 cm. In another embodiment, the diameter of the cylindrical air channels 140 is less than about 0.2 cm.

In one embodiment, the total surface area of the channels exposed on the proximal surface of the active agent component is greater than about 0.5% of the total surface area of the proximal surface of the active agent component. In another embodiment, the total surface area of the channels exposed on the proximal surface of the active agent component is greater than about 1% of the total surface area of the proximal surface of the active agent component. In another embodiment, the total surface area of the channels exposed on the proximal surface of the active agent component is greater than about 2% of the total surface area of the proximal surface of the active agent component. In another embodiment, the total surface area of the channels exposed on the proximal surface of the active agent component is less than about 40% of the total surface area of the proximal surface of the active agent component. In another embodiment, the total surface area of the channels exposed on the proximal surface of the active agent component is less than about 20% of the total surface area of the proximal surface of the active agent component. In another embodiment, the total surface area of the channels exposed on the proximal surface of the active agent component is less than about 10% of the total surface area of the proximal surface of the active agent component.

The total surface area of the channels exposed on the distal surface of the active agent component is preferably within the same ranges.

Although several specific configurations are described above, it should be understood that the channels may be of any shape such as but not limited to squares, diamonds, ovals, triangles, pentagons, or hexagons. The channels may also be non-linear and/or interconnected leaving peninsulas of skin-contacting polymeric matrix within the skin-contacting component.

The active agent component comprises a polymeric material and an active agent. The active agent is preferably dispersed homogeneously throughout the polymeric material, and more preferably dissolved within the polymeric material.

The proximal surface of the active agent component can be a skin-contacting surface which should be sufficiently conformable when placed on a skin surface so as to make intimate contact with at least a portion of the skin surface. In one embodiment, substantially all of the polymeric material of the proximal surface of the active agent component will make intimate contact with the skin surface of a patient.

In one embodiment, the active agent component has a thickness of no less than about 10 µm. In another embodiment, the active agent component has a thickness of no less than about 20 µm. In another embodiment, the active agent component has a thickness of no less than about 50 µm. In another embodiment, the active agent component has a thickness of no greater than about 250 µm. In another embodiment, the active agent component has a thickness of no greater than about 200 µm. In another embodiment, the active agent component has a thickness of no greater than about 150 µm.

The polymeric material of the active agent component preferably comprises a polymer selected from the group consisting of acrylates, natural rubbers, polyisobutylenes, polyisoprenes, styrenic block copolymers, polyvinylethers, silicone polymers, polyurethanes, and polyurethane-ureas, or mixtures thereof. The polymeric material may optionally contain other additives well known to those in the art, for example, penetration enhancers, tackifiers, plasticizers, antioxidants, colorants, crystallization inhibitors, and the like.

In one embodiment, the polymeric material may comprise a pressure-sensitive adhesive. Preferred pressure-sensitive adhesives for use in the dosage forms of the invention include acrylates, polyisobutylenes, silicone polymers, and mixtures thereof. Examples of useful polyisobutylene pressure-sensitive adhesives are described in U.S. Pat. No. 5,985,317 (Venkateshwaran et al.), the disclosure of which is incorporated herein by reference in its entirety for all purposes. Examples of useful acrylate and silicone polymer pressure-sensitive adhesives, and mixtures thereof, are described in U.S. Pat. No. 5,474,783 (Miranda et al.), the disclosure of which is incorporated herein by reference in its entirety for all purposes.

Acrylate polymers and copolymers are particularly preferred pressure-sensitive adhesives. Examples of suitable monomers for use in acrylate copolymers include alkyl acrylates, such as isooctyl, 2-ethylhexyl, n-butyl, ethyl, methyl, and dimethylhexyl, and alkyl methacrylates, such as lauryl, isodecyl, and tridecyl. Monomers containing functional groups, such as carboxylic acid, hydroxy, amide, and amino may also be incorporated into an acrylate copolymer. Examples of suitable monomers containing functional groups include acrylic acid, hydroxyalkyl acrylates containing 2 to 4 carbon atoms in the hydroxyalkyl group, acrylamide, N-vinyl-2-pyrrolidone, vinyl acetate, and alkoxyethyl acrylates.

Acrylate copolymers may optionally further comprise a substantially linear macromonomer copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference in its entirety for all purposes.

Other polymer materials of the active agent component may include but are not limited to polyethylene; polypropylene; ethylene/propylene copolymers; ethylene/ethylacrylate copolymers; ethylene/vinyl acetate copolymers; silicone elastomers, especially the medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly(ethylene terephthalate); butyl rubber; epichlorohydrin rubber; ethylene-vinyl alcohol copolymer; ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methylcellulose, and cellulose esters; polycarbonates; polytetrafluoroethylene; and combinations thereof. In one embodiment, the polymer matrix has a glass-transition temperature below room temperature. The polymer can, but need not necessarily, have a degree of crystallinity at room temperature. Cross-linking monomeric units or sites can be incorporated into the polymers. For example, cross-linking monomers can be incorporated into polyacrylate polymers. The cross-linking monomers provide sites for cross-linking the polymer matrix after microdispersing the active agent into the polymer. Known cross-linking monomers for polyacrylate polymers include, but are not limited to, polymethacrylic esters of polyols such as butylene diacrylate and dimethacrylate, trimethylol propane trimethacrylate, and the like. Other monomers that provide cross-linking sites include allyl acrylate, allyl methacrylate, diallyl maleate, and the like.

The active agent will be present in an amount such that the composition delivers a therapeutically effective amount for the condition being treated. This amount will vary according to the type of active agent used, the condition to be treated, the amount of time the composition is allowed to remain in contact with the skin of the subject, and other factors known to those of skill in the art. For example, information on dosing and the amount of opioid agonist active agent present in a transdermal dosage form is set forth in U.S. Published Patent Application No. 2002/0119187 A1, filed Sep. 26, 2001, entitled "Composition for the Transdermal Delivery of Fentanyl" by Cantor et al. and U.S. Published Patent Application No. 2003/0026829 A1, filed Mar. 15, 2002, entitled "Transdermal Administration of Fentanyl and Analogs Thereof" by Venkatraman et al. each of which are incorporated by reference herein in their entirety for all purposes. In one embodiment, the amount of active agent present in the transdermal drug delivery composition of the invention is greater than about 0.01 wt-%, based on the total weight of the composition of the active agent component. In another embodiment, the amount of active agent present in the transdermal drug delivery composition of the invention is greater than about 1.0 wt-%, based on the total weight of the composition of the active agent component. In another embodiment, the amount of active agent present in the transdermal drug delivery composition of the invention is less than about 40 wt-%, based on the total weight of the composition of the active agent component. In another embodiment, the amount of active agent present in the transdermal drug delivery composition of the invention is less than about 20.0 wt-%, based on the total weight of the composition of the active agent component.

The analgesically effective amount of an opioid present in the transdermal dosage form, however, typically ranges from about 0.01 to about 50 mg/cm$^2$ in one embodiment, from about 0.05 to about 15 mg/cm$^2$ in another embodiment, and from about 0.05 to about 5.0 mg/cm$^2$ in another embodiment. It is well within the purview of one skilled in the art to readily determine the analgesically effective amount of an opioid needed for a particular indication.

Figure 2:
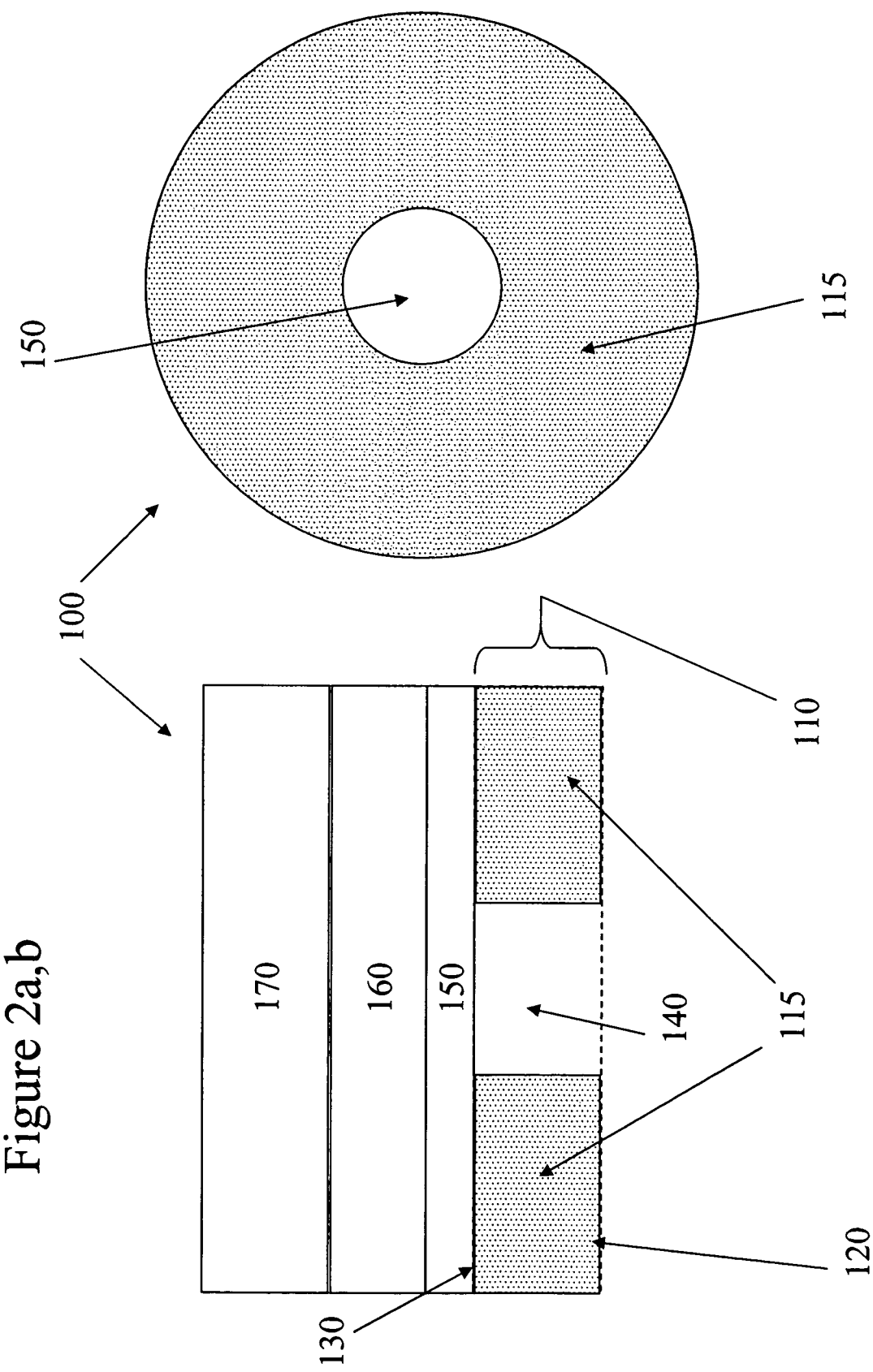
FIGS. 2a, b show a schematic cross-section (2a) and a plan view (2b) of an embodiment of the present invention where the skin-contacting component comprises an annular disk with a central air channel.
Figure 3:
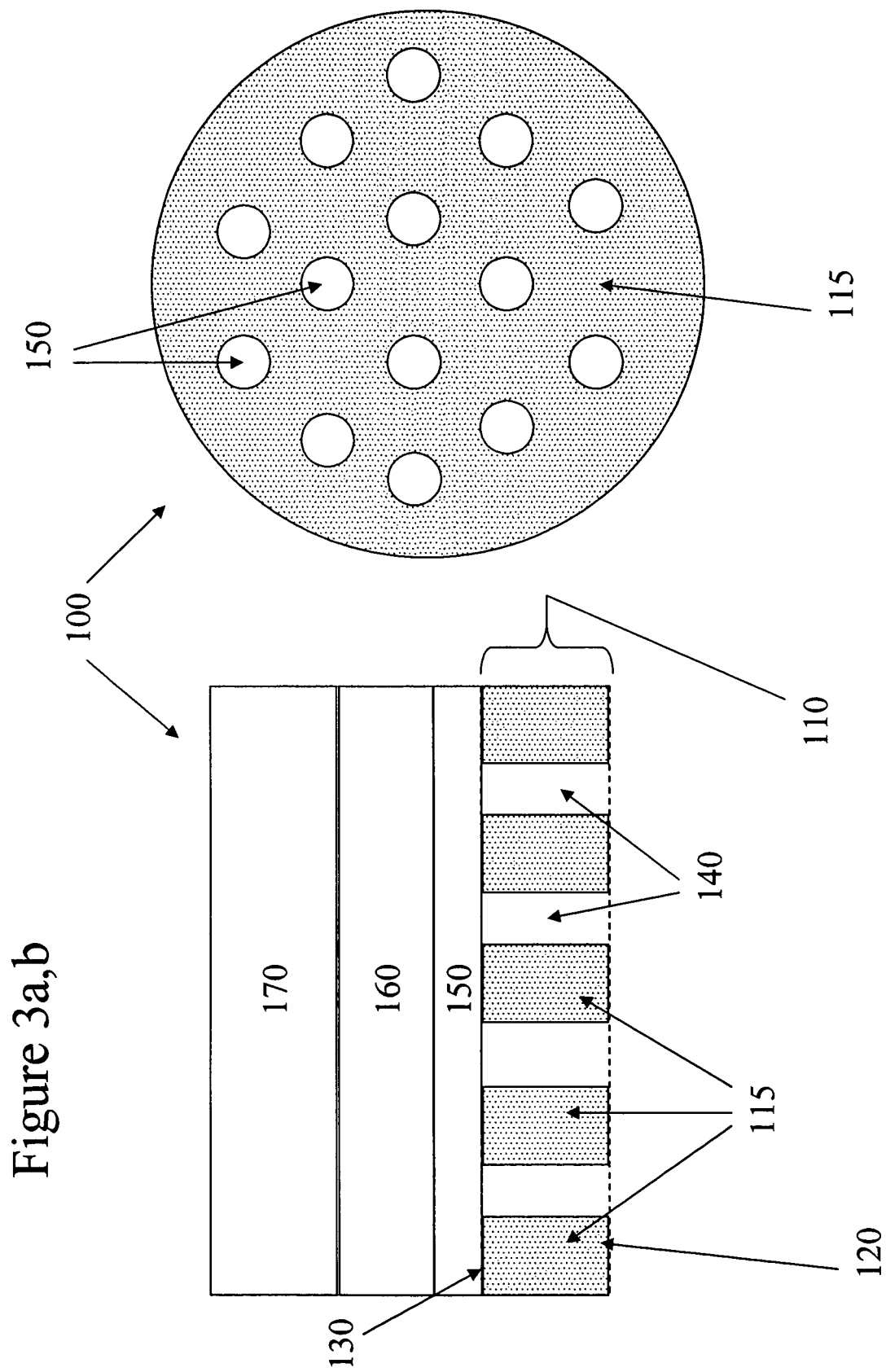
FIGS. 3a, b show a schematic cross-section (3a) and a plan view (3b) of an embodiment of the present invention where the skin-contacting component comprises a disk with a plurality of cylindrical air channels.

In FIGS. 1, 2, and 3, the adverse agent 160 component is connected on one side to a barrier 150 component and on the other side to a backing 170. The adverse agent component 160 can be a polymeric material, porous film, or other material suitable for containing an adverse agent. Preferably, the reservoir component 160 is capable of containing a sufficient amount of adverse agent to blunt or block at least one biological effect of the active agent or to cause at least one unpleasant side effect in a patient or animal which has absorbed the total amount of active agent in the dosage form 100. This amount can vary according to the amount and type of active agent in the dosage form. The adverse agent component comprises an adverse agent in any form or composition or reservoir which allows the adverse agent to be at least partially extracted in the presence of a solvent, including but not limited to, water, ethanol or ether, or mixtures thereof. In certain embodiments, the adverse agent can be dispersed, mixed and/or dissolved in a polymeric material, including but not limited to, the polymeric materials which are suitable for incorporation into the active agent component.

Suitable polymeric materials or matrices for use in the adverse agent component include, but are not limited to, acrylates, natural rubbers, polyisobutylenes, polyisoprenes, styrenic block copolymers, polyvinylethers, silicone polymers, polyurethanes, and polyurethane-ureas. In one embodiment, the adverse agent is preferably dispersed substantially homogeneously throughout a polymeric material. In one embodiment, the adverse agent is dissolved in the polymeric material. In another embodiment, the adverse agent component includes solid crystals of adverse agent dispersed throughout the polymeric material. In certain embodiments, the polymeric matrix is preferably a pressure sensitive adhesive. Suitable pressure-sensitive adhesives include those suitable for use as the polymeric material of the active agent component. Additionally, pressure-sensitive adhesives that are not suitable for direct skin contact can be suitable for use as the polymeric material of the adverse agent.

The adverse agent component can also comprise a porous medium, such as a woven fabric, porous or microporous film, or other open, mesh-like material, wherein at least a portion of the pores contain adverse agent. The adverse agent can be present within the pores in any form, including but not limited to a liquid, a gel or a solid, such as a solid crystalline or powdered material. For example, the adverse agent can be mixed with a carrier, such as a viscous liquid, semi-solid or gel material. Examples of suitable materials for incorporation into the adverse agent component include, but are not limited to, microporous films formed by extruding polyethylene or polypropylene with mineral oil as described in U.S. Pat. No. 4,539,256 (Shipman), the disclosure of which is incorporated herein by reference in its entirety for all purposes.

Other polymer materials of the adverse agent component may include but are not limited to polyethylene; polypropylene; ethylene/propylene copolymers; ethylene/ethylacrylate copolymers; ethylene/vinyl acetate copolymers; silicone elastomers, especially the medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly(ethylene terephthalate); butyl rubber; epichlorohydrin rubber; ethylene-vinyl alcohol copolymer; ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methylcellulose, and cellulose esters; polycarbonates; polytetrafluoroethylene; and combinations thereof. In one embodiment, the polymer matrix has a glass-transition temperature below room temperature. The polymer can, but need not necessarily, have a degree of crystallinity at room temperature. Cross-linking monomeric units or sites can be incorporated into the polymers. For example, cross-linking monomers can be incorporated into polyacrylate polymers. The cross-linking monomers provide sites for cross-linking the polymer matrix after microdispersing the adverse agent into the polymer. Known cross-linking monomers for polyacrylate polymers include, but are not limited to, polymethacrylic esters of polyols such as butylene diacrylate and dimethacrylate, trimethylol propane trimethacrylate, and the like. Other monomers that provide cross-linking sites include allyl acrylate, allyl methacrylate, diallyl maleate, and the like. In one embodiment the polymer matrix does not allow any, or any detectable amount, of an adverse agent to diffuse out of it, particularly in those instances in which the adverse agent can penetrate a patient's skin.

In one embodiment, the adverse agent component has a thickness of no less than about 10 μm. In another embodiment, the adverse agent component has a thickness of no less than about 20 μm. In another embodiment, the adverse agent component has a thickness of no less than about 50 μm. In another embodiment, the adverse agent component has a thickness of no greater than about 250 μm. In another embodiment, the adverse agent component has a thickness of no greater than about 200 μm. In another embodiment, the adverse agent component has a thickness of no greater than about 150 μm.

The barrier 150, as shown in FIGS. 1, 2, and 3, is a substantially continuous component adjacent to the distal surface of the active agent component 130 on one side and the adverse agent component 160 on the other side.

The permeability of the barrier to such a solvent is such that solvent can pass through the barrier or that the solvent may dissolve or erode at least a portion of the barrier, such that at least a portion of the active agent and/or adverse agent can pass through the barrier or an channel formed in the barrier in the presence of solvent. Movement of active agent and/or adverse agent across the barrier and/or a channel formed by dissolution of the barrier in the presence of a solvent will occur in amounts and at a rate that will vary depending on the particular composition and configuration of the dosage form, such as the relative amounts and types of active agent and adverse agent. However, preferably a sufficient amount of adverse agent, including the amount which passes through the barrier, will be extracted from the dosage form to cause an unpleasant biological effect or to blunt or block at least one biological effect of the amount of active agent that is also extracted by the solvent, when both the active agent and the adverse agent are absorbed into the blood stream of an animal. It is preferred that at least a portion of the adverse agent will pass through the barrier after the barrier has been exposed to solvent for a time period of less than 30 minutes, more preferably less than 15 minutes, and most preferably less than 5 minutes. The amount of adverse agent that will pass through the barrier in the presence of a solvent is preferably more than 10 μg, more preferably more than 50 μg, and most preferably more than 200 μg.

Although extraction may be performed in vitro, such as in a laboratory type setting (e.g., by immersion of a dosage form in a beaker of solvent), it should also be understood that extraction of adverse agent and active agent may also take place in vivo, such as in the saliva present in the oral cavity or the gastric fluid present in the stomach.

The impermeability of the barrier to diffusion of active agent and adverse agent in the absence of a solvent is such that less than a significant amount, and preferably none, of active agent or adverse agent diffuse across the barrier during normal storage or use of the dosage form. The precise amounts which are less than significant will vary depending on the particular composition and intended therapeutic purpose of the dosage form, but it will be understood to include any amounts of active agent or adverse agent that do not significantly alter the therapeutic effect of the dosage form (e.g., the active agent concentration in the skin-contacting component does not change significantly due to diffusion of active agent across the barrier and a pharmacologically effective amount of adverse agent does not diffuse across the barrier and into the skin-contacting component). Any insignificant amounts of active agent that may diffuse across the barrier are preferably less than 5%, more preferably less than 1%, and most preferably less than 0.1% by weight of the total active agent in the dosage form. Any insignificant amounts of active agent that may diffuse across the barrier will preferably do so over a time period greater than 1 month, more preferably greater than 6 months, and most preferably greater than 2 years.

In a preferred embodiment, the active agent is not in diffusional communication with the reservoir component during normal usage. Diffusional communication is understood to mean that a substance, such as an active agent, is able to diffuse from one area to another by passing through or across one or more solid or liquid media.

Suitable barriers can comprise, for example, dissolvable films, such as polyvinyl alcohol or modified polyvinyl alcohols. Suitable barriers may also comprise porous or microporous films.

Suitable barriers can be films comprised of, but not limited to, polyesters, such as polyethylene terephthalate, polypropylenes, and polyethylenes such as high density polyethylene. Suitable barriers can also be multi-component films comprised of but not limited to polyethylene terephthalate-aluminum-polyethylene composites or polyethylene terephthalate-ethylene vinyl acetate composites. Also, barriers can be comprised of a polyperfluorocarbon. Suitable barriers may also be comprised of a polymer based material including but not limited to a cellulose polymer, such as hydroxypropyl methylcellulose, hydroxypropyl cellulose or hydroxyethyl cellulose, and/or polyvinylpyrolidine. The hydroxyethyl cellulose may be NATROSOL® 250 HNF (available from the Aqualon Division of Hercules Inc., Wilmington, Del.). The hydroxypropyl cellulose may be KLUCEL® HXAF (available from the Aqualon Division of Hercules Inc.). A suitable plasticizer may be incorporated into the barrier, such as but not limited to triethanolamine, triacetin, glycerol monooleate, polyethyleneglycol 600, levulinic acid, and mixtures of any two or more of the foregoing.

Barriers of the present invention may be formed having a discontinuous structure that can be subsequently laminated or otherwise attached to the discontinuous structure of the skin-contacting component. It is preferred that the barrier and the polymeric material or matrix of the active agent component are fully aligned. It is not necessary for the two components to be completely registered, however, as long as the barrier serves to deter diffusion of the active agent and adverse agent through the barrier component. Discontinuous barriers of the present invention may also be formed at the same time that the discontinuities in the polymeric material or matrix of the active agent component are formed. For example, a continuous barrier film may be coated with a continuous skin-contacting polymeric matrix or laminated to a continuous skin-contacting polymeric matrix. Channels or holes may be created in the laminate using any suitable hole-forming process, such as punching, so that aligned channels are simultaneously created in both the barrier and the skin-contacting polymeric matrix.

Barriers of the present invention can also comprise an impermeable surface coating applied to one of the other surfaces present in the dosage form, such as the distal surface of the active agent or skin-contacting component opposed to the skin-contacting surface or the adverse agent or surface of the reservoir component facing the skin-contacting component. Examples of suitable coatings include fluoropolymers, such as polymers or copolymers of tetrafluoroethylene, hexafluoropropylene, and/or vinylidene fluoride. Terpolymers of tetrafluoroethylene, hexafluoropropylene, and vinylidene fluoride, such as Dyneon™ fluorothermoplastic THV are preferred coatings. In one embodiment, the thickness of impermeable surface coating is from about 0.5 to about 10 µm. In another embodiment, the thickness of impermeable surface coating is from about 1 to about 5 µm. In another embodiment, the thickness of impermeable surface coating is from about 2 to about 4 µm. In another embodiment, the barrier is a thin coating on the surface of a microporous film reservoir or adverse agent component.

In one embodiment, the barrier thickness is greater than about 1 µm.

In another embodiment, the barrier thickness is greater than about 10 µm.

In another embodiment, the barrier thickness is greater than about 20 µm.

In another embodiment, the barrier thickness is less than about 100 µm.

In another embodiment, the barrier thickness is less than about 80 µm.

In another embodiment, the barrier thickness is less than about 75 µm.

In another embodiment, the barrier thickness is less than about 60 µm. In another embodiment, the barrier thickness is less than about 50 µm.

In another embodiment, shown in FIGS. 4a and 4b, the present invention comprises a transdermal dosage form 200 comprising an active agent component which is a skin-contacting component 210 comprising a skin-contacting polymeric matrix 215 and an active agent, a reservoir or adverse agent component 260 comprising an adverse agent to the active agent, and a barrier 250. The skin-contacting component has a proximal, skin-contacting surface 220, a distal surface opposed to the skin-contacting surface 230, and channels 240 passing between the proximal and distal surfaces. The barrier 250 is present as a discontinuous component that is adjacent to the distal surface of the skin-contacting component 230 and the reservoir component 260. A backing 270 is adjacent to a surface of the reservoir 260 and provides an outer surface 290 of the dosage form 200. In one embodiment, the surface of the reservoir component which is adjacent to the backing is opposed to the surface of the reservoir component which is adjacent.

As shown in FIGS. 4a and 4b, the skin-contacting component 210 comprises a plurality of strips comprising a skin-contacting polymeric matrix 215 and an active agent, wherein the strips are separated by channels 240. In this embodiment the channels 240 are filled with air. The discontinuous barrier is aligned with the skin-contacting polymeric matrix 215 so that at least one continuous air channel 240 passes from a plane defined by the adjacent proximal, skin-contacting surface 220 to the reservoir component 260. In one embodiment, the width of the strips comprising the skin-contacting polymeric matrix 215 and the active agent is greater than about 0.1 cm. In another embodiment, the width of the strips comprising the skin-contacting polymeric matrix 215 and the active agent is greater than about 0.2 cm. In another embodiment, the width of the strips comprising the skin-contacting polymeric matrix 215 and the active agent is greater than about 0.4 cm. In another embodiment, the width of the strips comprising the skin-contacting polymeric matrix 215 and the active agent is less than about 2.0 cm. In another embodiment, the width of the strips comprising the skin-contacting polymeric matrix 215 and the active agent is less than about 1.0 cm. In another embodiment, the width of the strips comprising the skin-contacting polymeric matrix 215 and the active agent is less than about 0.6 cm.

In another embodiment, as shown in FIGS. 5a and 5b, the active agent or skin-contacting component 210 consists of an annular disk comprising a skin-contacting polymeric matrix 215 and an active agent with a central channel 240 filled with air.

In still another embodiment, as shown in FIGS. 6a and 6b, the active agent or skin-contacting component 210 consists of a disk with a plurality of cylindrical air channels 240. In one embodiment, the diameter of the cylindrical air channels 240 is greater than about 0.015 cm. In another embodiment, the diameter of the cylindrical air channels 240 is greater than about 0.05 cm. In another embodiment, the diameter of the cylindrical air channels 240 is greater than about 0.1 cm. In another embodiment, the diameter of the cylindrical air channels 240 is less than about 1.0 cm. In another embodiment, the diameter of the cylindrical air channels 240 is less than about 0.5 cm. In another embodiment, the diameter of the cylindrical air channels 240 is less than about 0.2 cm.

In one embodiment, the total surface area of the channels 240 is greater than about 0.5% of the total surface area of the skin-contacting surface 220. In another embodiment, the total surface area of the channels 240 is greater than about 1% of the total surface area of the skin-contacting surface 220. In another embodiment, the total surface area of the channels 240 is greater than about 2% of the total surface area of the skin-contacting surface 220. In another embodiment, the total surface area of the channels 240 is less than about 40% of the total surface area of the skin-contacting surface 220. In another embodiment, the total surface area of the channels 240 is less than about 20% of the total surface area of the skin-contacting surface 220. In another embodiment, the total surface area of the channels 240 is less than about 10% of the total surface area of the skin-contacting surface 220.

Figure 4:
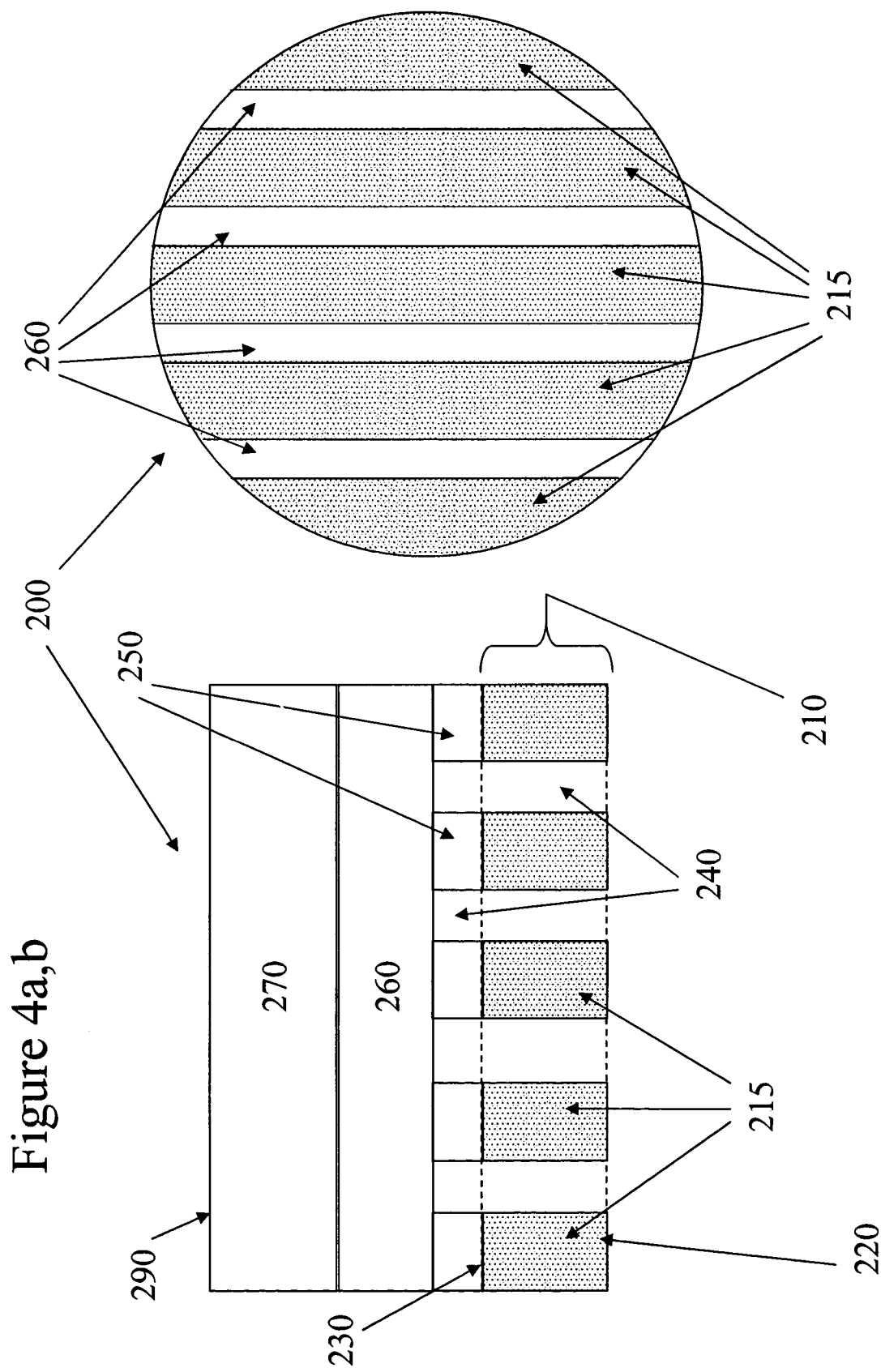
FIGS. 4a, b show a schematic cross-section (4a) and a plan view (4b) of an embodiment of the present invention where the skin-contacting component comprises strips separated by air channels. In this embodiment the barrier comprises strips separated by air channels and the barrier is aligned with the skin-contacting component.
Figure 5:
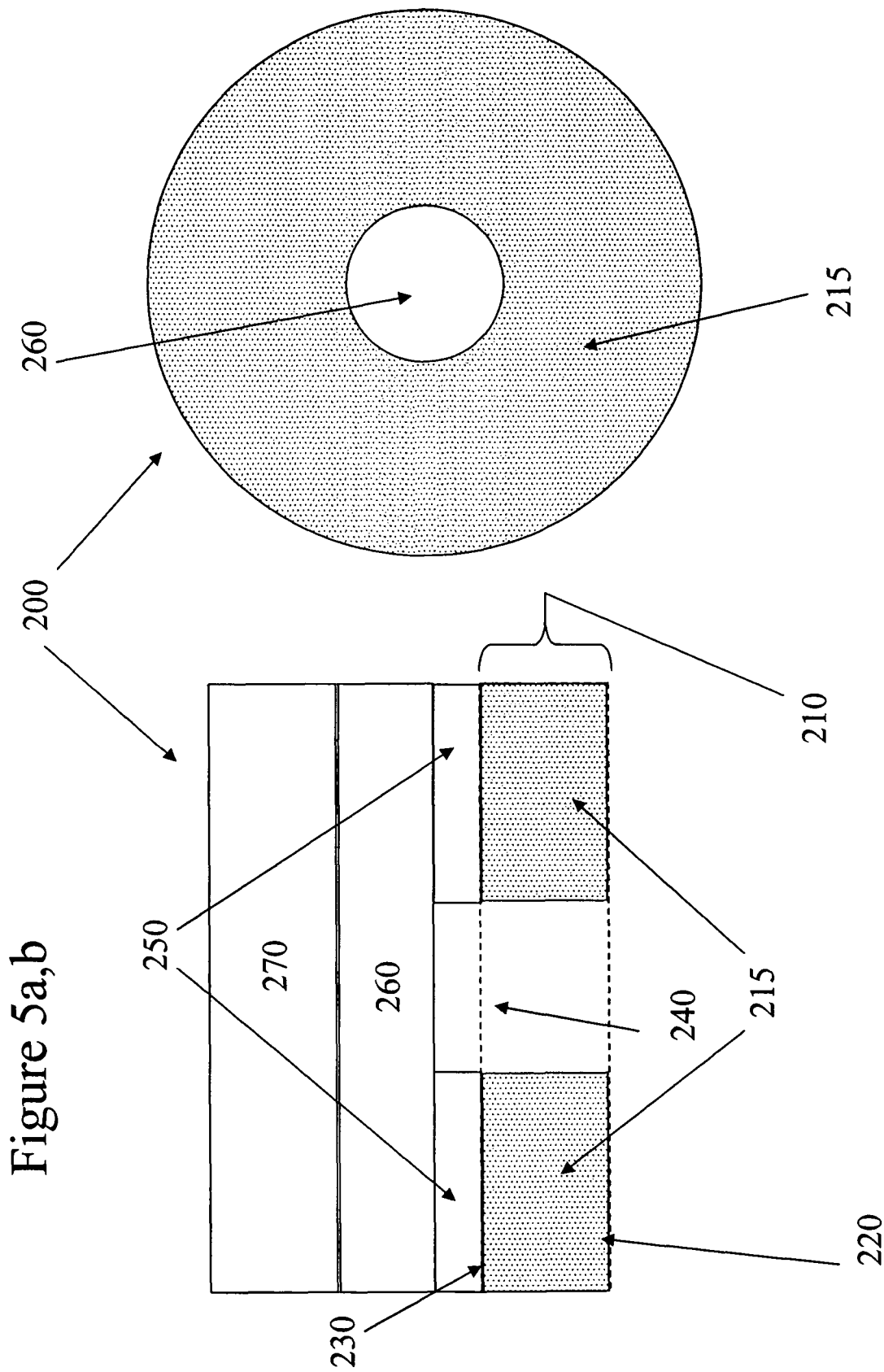
FIGS. 5a, b show a schematic cross-section (5a) and a plan view (5b) of an embodiment of the present invention where the skin-contacting component comprises an annular disk with a central air channel. In this embodiment the barrier comprises an annular disk with a central air channel and the barrier is aligned with the skin-contacting component.
Figure 6:
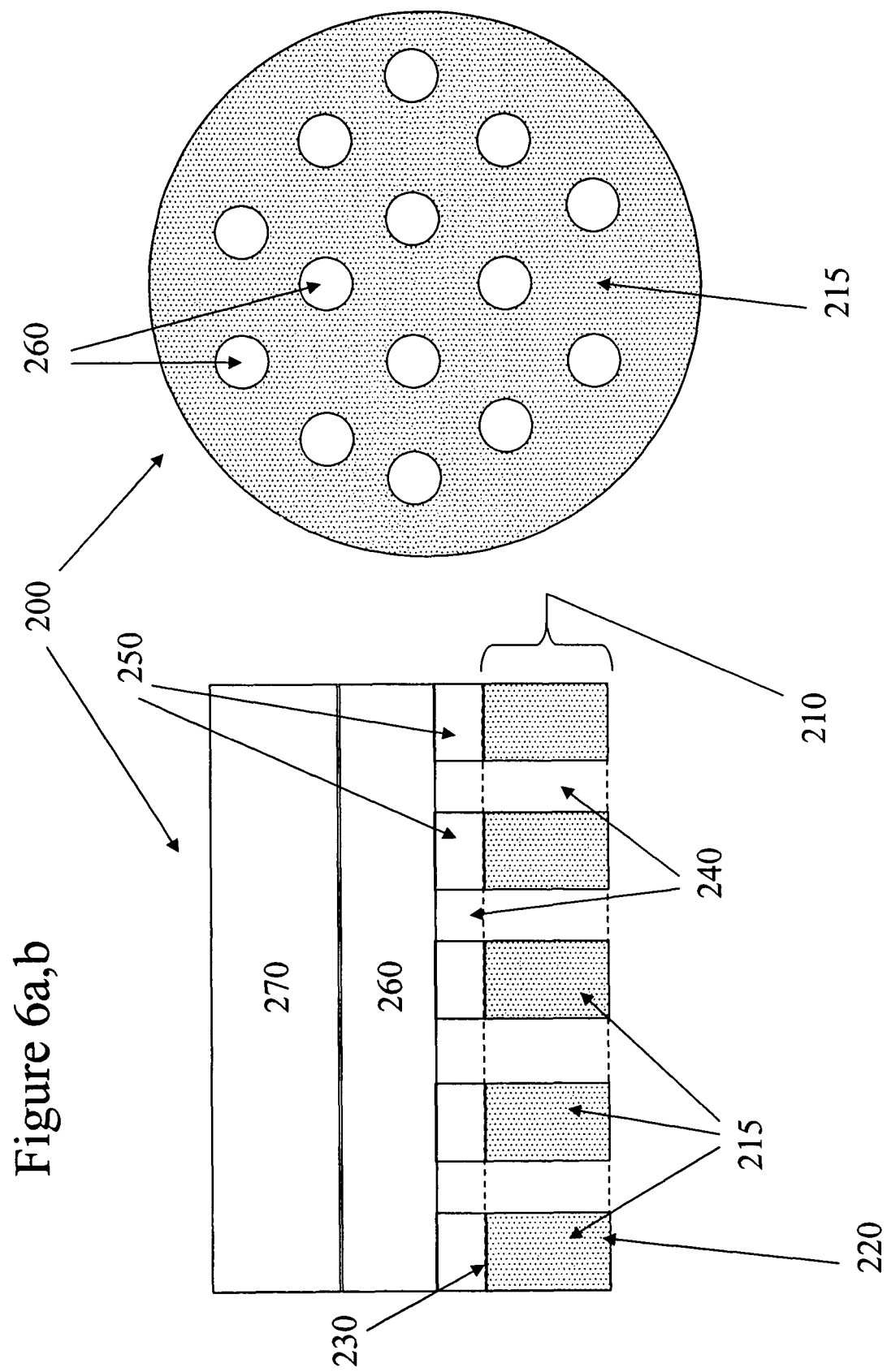
FIGS. 6a, b show a schematic cross-section (6a) and a plan view (6b) of an embodiment of the present invention where the skin-contacting component comprises a disk with a plurality of cylindrical air channels. In this embodiment the barrier comprises a disk with a plurality of cylindrical air channels and the barrier is aligned with the skin-contacting component.

The barrier 250, as shown in FIGS. 4, 5, and 6, is a discontinuous component adjacent to the distal surface of the active agent or skin-contacting component 230 on one side and the adverse agent or reservoir component 260 on the other side. The barrier is impermeable to diffusion of active agent and adverse agent in the absence of a suitable solvent.

Dissolvable films, such as the films described in the embodiments shown in FIGS. 1, 2, and 3 may be optionally used.

Figure 7:
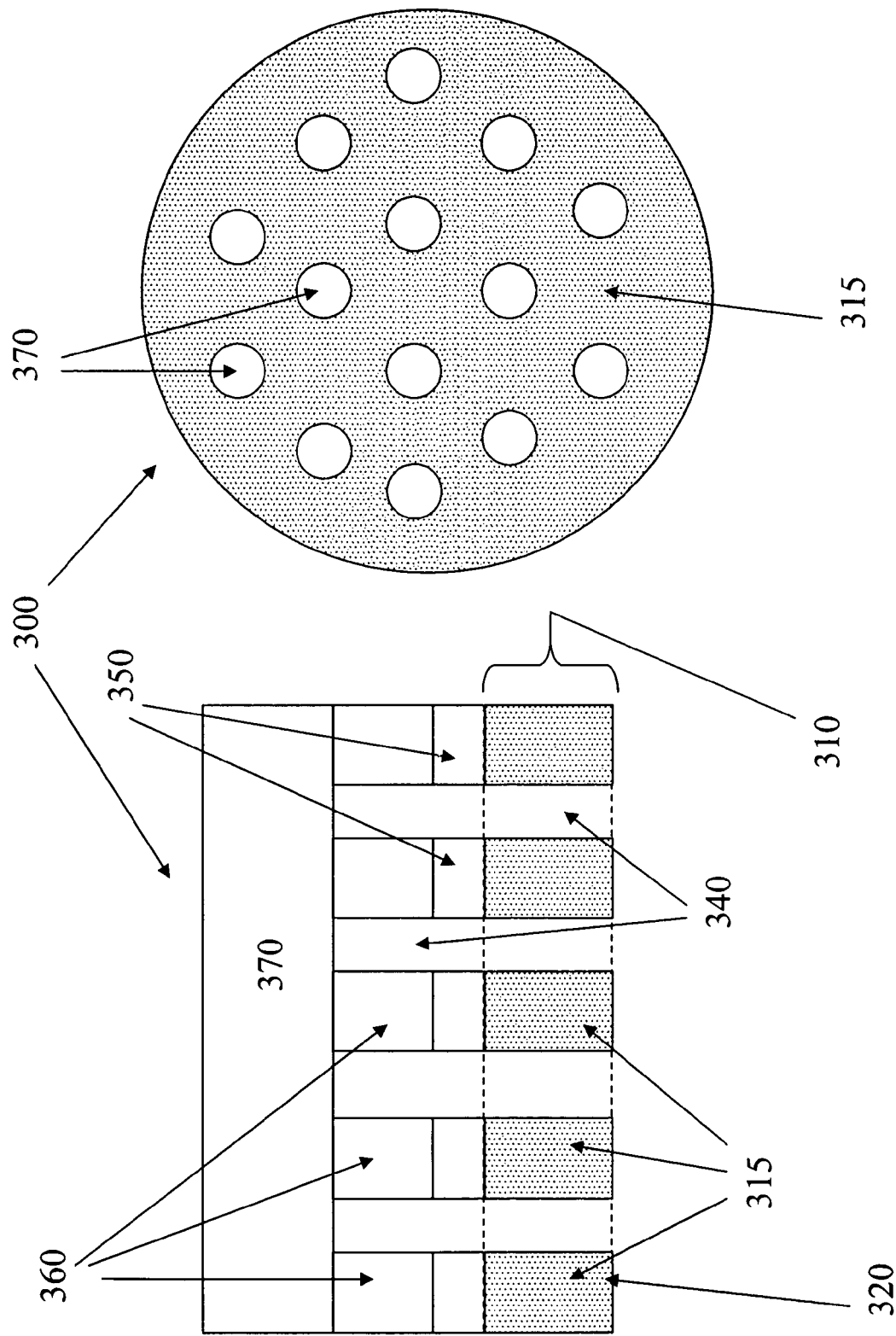
FIGS. 7a, b show a schematic cross-section (7a) and a plan view (7b) of an embodiment of the present invention where the skin-contacting component comprises a disk with a plurality of cylindrical air channels. In this embodiment the barrier and reservoir comprise disks with a plurality of cylindrical air channels. The barrier and reservoir are aligned with the skin-contacting component.

Channels 340 may also be present in the adverse agent or reservoir component 360. As shown in FIGS. 7a, and 7b the channels 340 are a plurality of channels that are substantially aligned with the channels in the barrier 350 and skin-contacting polymeric matrix 315. Channels in the reservoir component 360 may be formed in the same manner as channels in the other components, that is, independently with a subsequent lamination/alignment step or simultaneously following lamination of continuous components.

In the embodiments shown in FIGS. 4, 5, 6, and 7 suitable skin-contacting components, skin-contacting polymeric matrices, active agents, reservoir components, and adverse agents are as described in the embodiments shown in FIGS. 1, 2, and 3.

In another embodiment, shown in FIGS. 8a and 8b, the present invention comprises a transdermal dosage form 400 comprising an active agent component which is a skin-contacting component 410 comprising a skin-contacting polymeric matrix 415 and an active agent, an adverse agent or reservoir component 460 comprising an adverse agent to the active agent, and a barrier 450. The skin-contacting component has a proximal, skin-contacting surface 420, a distal surface opposed to the skin-contacting surface 430, and channels 440 passing between the proximal and distal surfaces. The barrier 450 is present as a component that is adjacent to the distal surface of the skin-contacting component 430 and the reservoir component 460. A backing 470 is adjacent to the reservoir 460 and provides an outer surface 490 of the dosage form 400.

As shown in FIGS. 8a and 8b, the skin-contacting component 410 consists of a disk with a plurality of cylindrical channels 440. The channels 440 are filled with a dissolvable, erodible, or porous material, such that the channels 440 are permeable to a solvent selected from the group consisting of water, ethanol, ether, and mixtures thereof, and the channels 440 are impermeable to diffusion of active agent and adverse agent in the absence of said solvent. Suitable materials for use as channels 440 may include, for example, dissolvable films, such as polyvinyl alcohol or modified polyvinyl alcohols. Suitable materials may also include porous or microporous films.

In one embodiment, the diameter of the cylindrical air channels 440 is greater than about 0.015 cm. In another embodiment, the diameter of the cylindrical air channels 440 is greater than about 0.05 cm. In another embodiment, the diameter of the cylindrical air channels 440 is greater than about 0.1 cm. In another embodiment, the diameter of the cylindrical air channels 440 is less than about 1.0 cm. In another embodiment, the diameter of the cylindrical air channels 440 is less than about 0.5 cm. In another embodiment, the diameter of the cylindrical air channels 440 is less than about 0.2 cm.

In one embodiment, the total surface area of the channels 440 is greater than about 0.5% of the total surface area of the skin-contacting surface 420. In another embodiment, the total surface area of the channels 440 is greater than about 1% of the total surface area of the skin-contacting surface 420. In another embodiment, the total surface area of the channels 440 is greater than about 2% of the total surface area of the skin-contacting surface 420. In another embodiment, the total surface area of the channels 440 is less than about 40% of the total surface area of the skin-contacting surface 420. In another embodiment, the total surface area of the channels 440 is less than about 20% of the total surface area of the skin-contacting surface 420. In another embodiment, the total surface area of the channels 440 is less than about 10% of the total surface area of the skin-contacting surface 420.

Figure 8:
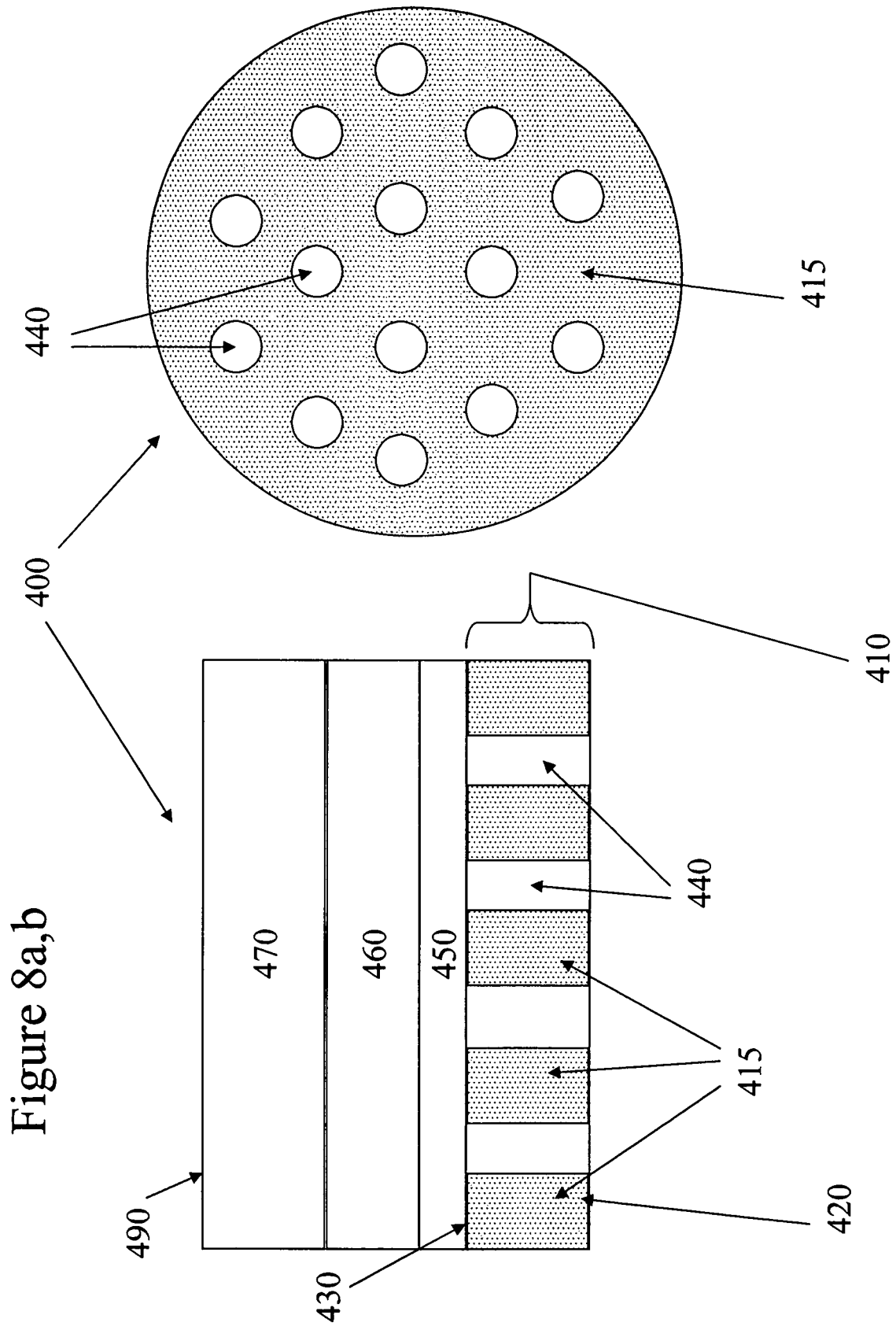
FIGS. 8a, b show a schematic cross-section (8a) and a plan view (8b) of an embodiment of the present invention where the skin-contacting component comprises a disk with a plurality of cylindrical channels, wherein the channels comprise a dissolvable material.

In the embodiment shown in FIG. 8, suitable skin-contacting components, skin-contacting polymeric matrices, active agents, reservoir components, barriers, and adverse agents are as described in the embodiments shown in FIGS. 1, 2, and 3.

Figure 9:
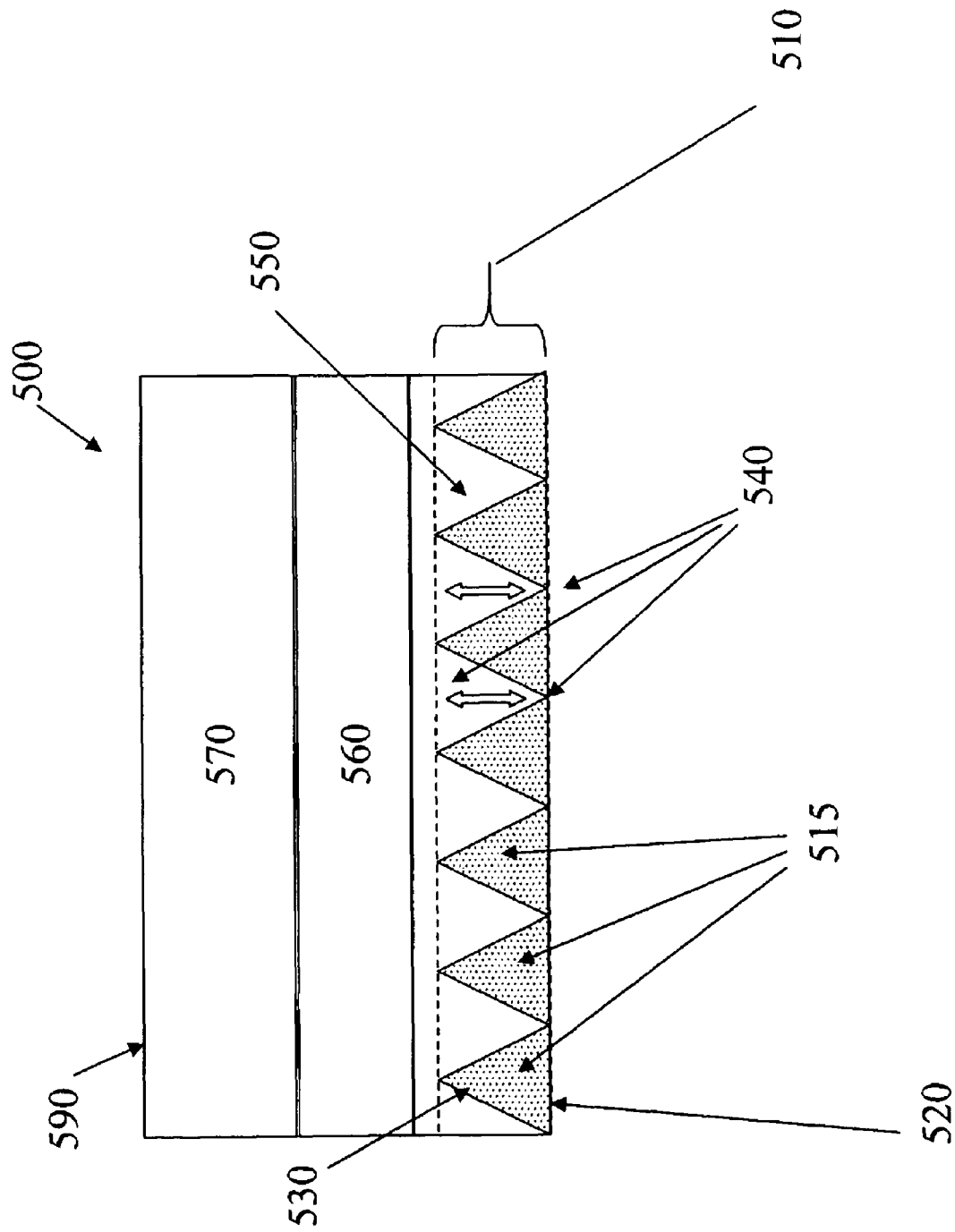
FIG. 9 shows a schematic cross-section of an embodiment of the present invention where the skin-contacting component has a structured surface facing the barrier.

In another embodiment, shown in FIG. 9, the present invention comprises a transdermal dosage form 500 comprising an active agent component which is a skin-contacting component 510 comprising a skin-contacting polymeric matrix 515 and an active agent, an adverse agent or reservoir component 560 comprising an adverse agent to the active agent, and a barrier 550.

The skin-contacting component has a proximal, skin-contacting surface 520 and a distal surface opposed to the skin-contacting surface 530. As shown in FIG. 9, the distal surface opposed to the skin-contacting surface 530 is a structured surface composed of a series of ridges or pyramids. The barrier 550 is present as a component that is adjacent to the distal surface of the skin-contacting component 530, and as such has an interlocking pattern of ridges or pyramids. The non-patterned side of the barrier is adjacent to the reservoir component 560. A backing 570 is adjacent to the reservoir 560 and provides an outer surface 590 of the dosage form 500.

The ridges or pyramids may be formed by any well known techniques for preparing embossed or microreplicated polymeric components, such as those in U.S. Pat. No. 6,123,890 (Mazurek et al.), the disclosure of which is incorporated herein by reference in its entirety for all purposes.

Suitable barriers include barrier materials of the embodiments described in FIGS. 1, 2, and 3.

The channels 540 are formed connecting the skin-contacting surface 520 to the reservoir component 560. As shown in FIG. 9, the channels 540 are filled with the barrier 550. The barrier is permeable to and/or at least partially soluble in a solvent selected from the group consisting of water, ethanol, ether, and mixtures thereof, and the barrier is substantially impermeable to diffusion of active agent and adverse agent in the absence of said solvent. The ridges or pyramids of the skin-contacting polymeric matrix 515 are preferably formed such that a small opening exists between neighboring ridges or pyramids. As shown in FIG. 9, the ridges or pyramids abut each other at a point contact. It should be understood that a point contact between neighboring ridges can effectively allow for fluid communication of solvent between the skin-contacting surface 520 and the reservoir component 560. It should be further understood that the channel may contain an insubstantial amount of the skin-contacting polymeric matrix, but can still substantially provide an open passage to solvent. In one embodiment, the connection between neighboring ridges or pyramids is of an insubstantial amount with a thickness of less than about 5 µm. In another embodiment, the connection between neighboring ridges or pyramids has a thickness of less than about 1 µm.

In this embodiment, suitable skin-contacting components, skin-contacting polymeric matrices, active agents, reservoir components, and adverse agents are as described in the embodiments shown in FIGS. 1, 2, and 3.

Figure 10:
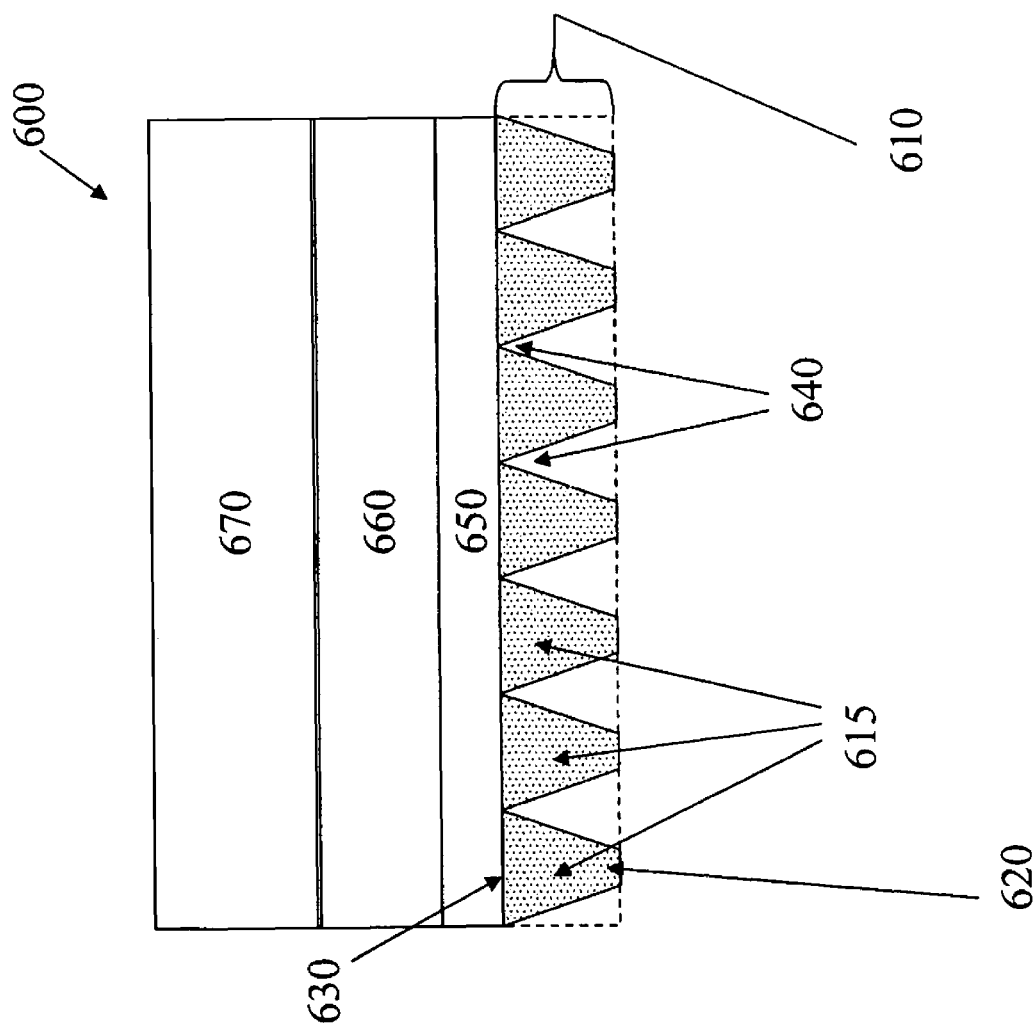
FIG. 10 shows a schematic cross-section of an embodiment of the present invention where the skin-contacting component has a structured surface facing away from the barrier.

In another embodiment, shown in FIG. 10, the present invention comprises a transdermal dosage form 600 comprising an active agent component which is a skin-contacting component 610 comprising a skin-contacting polymeric matrix 615 and an active agent, an adverse agent or reservoir component 660 comprising an adverse agent to the active agent, and a barrier 650. The skin-contacting component has a proximal, skin-contacting surface 620, a distal surface opposed to the skin-contacting surface 630, and channels 640 passing between the proximal and distal surfaces. As shown in FIG. 10, the skin-contacting polymeric matrix 615 is a structured component comprising ridges or truncated pyramids.

The channels 640 provide open fluid communication between the skin-contacting surface 620 to the barrier 650. The ridges or pyramids of the skin-contacting component 610 are preferably formed such that a small opening exists between neighboring ridges or pyramids. As shown in FIG. 10, the ridges or pyramids abut each other at a point contact.

It should be understood that a point contact between neighboring ridges can effectively allow for fluid communication of solvent between the skin-contacting surface 620 and the barrier 650. It should be further understood that the channel may contain an insubstantial amount of the skin-contacting polymeric matrix, but can still substantially provide an open passage to solvent. In one embodiment, the connection between neighboring ridges or pyramids is of an insubstantial amount with a thickness of less than about 5 µm. In another embodiment, the connection between neighboring ridges or pyramids has a thickness of less than about 1 µm.

Figure 11:
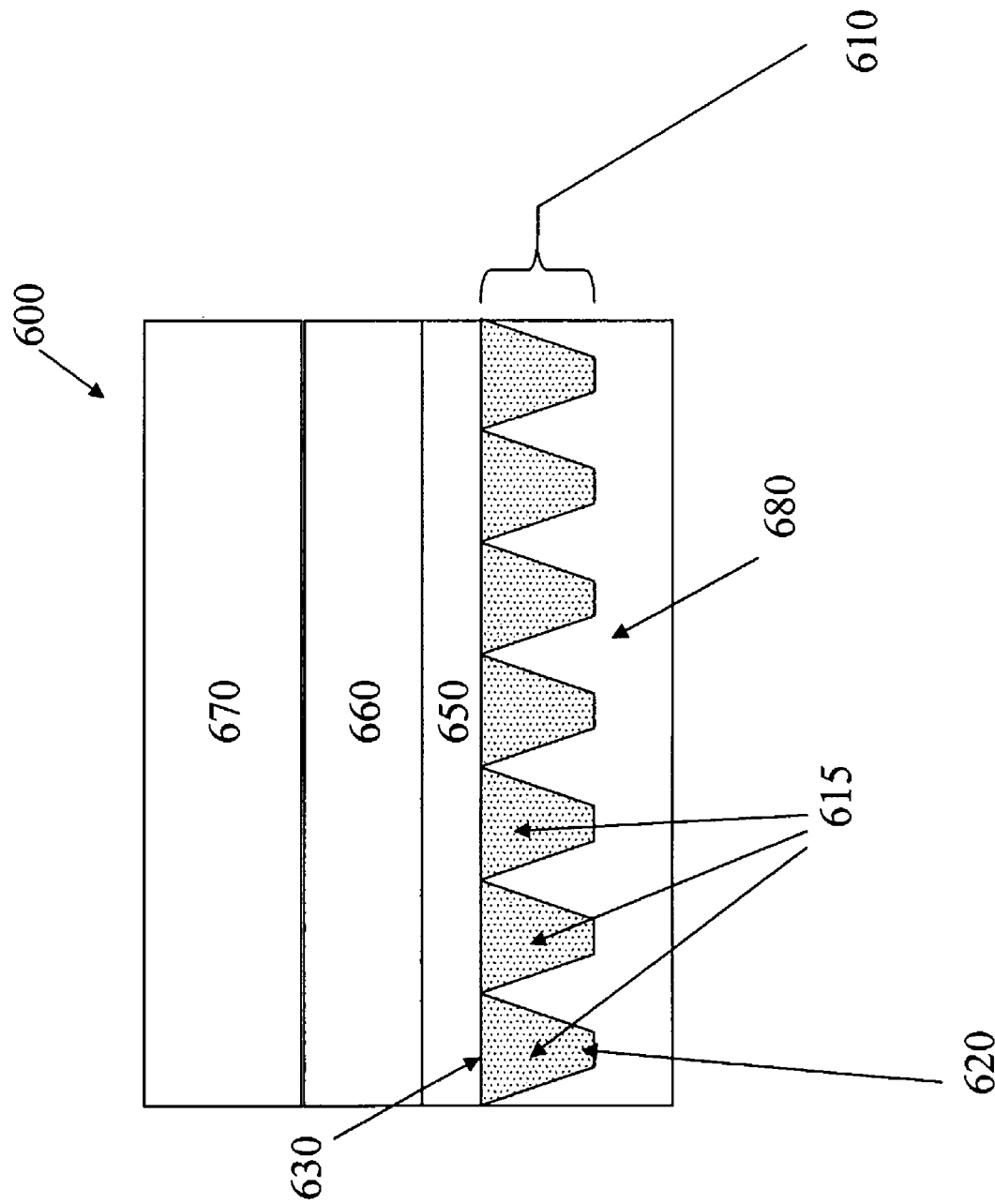
FIG. 11 shows a schematic cross-section of an embodiment of the present invention similar as shown in FIG. 10, further comprising a structured release liner.

As shown in FIG. 11, the dosage form of FIG. 10 may further comprise a structured release liner 680 which serves to protect the structured surface of the skin-contacting polymeric matrix 615 prior to use of the dosage form.

In this embodiment, suitable skin-contacting components, skin-contacting polymeric matrices, active agents, reservoir components, barriers, and adverse agents are as described in the embodiments shown in FIGS. 1, 2, and 3.

Figure 12:
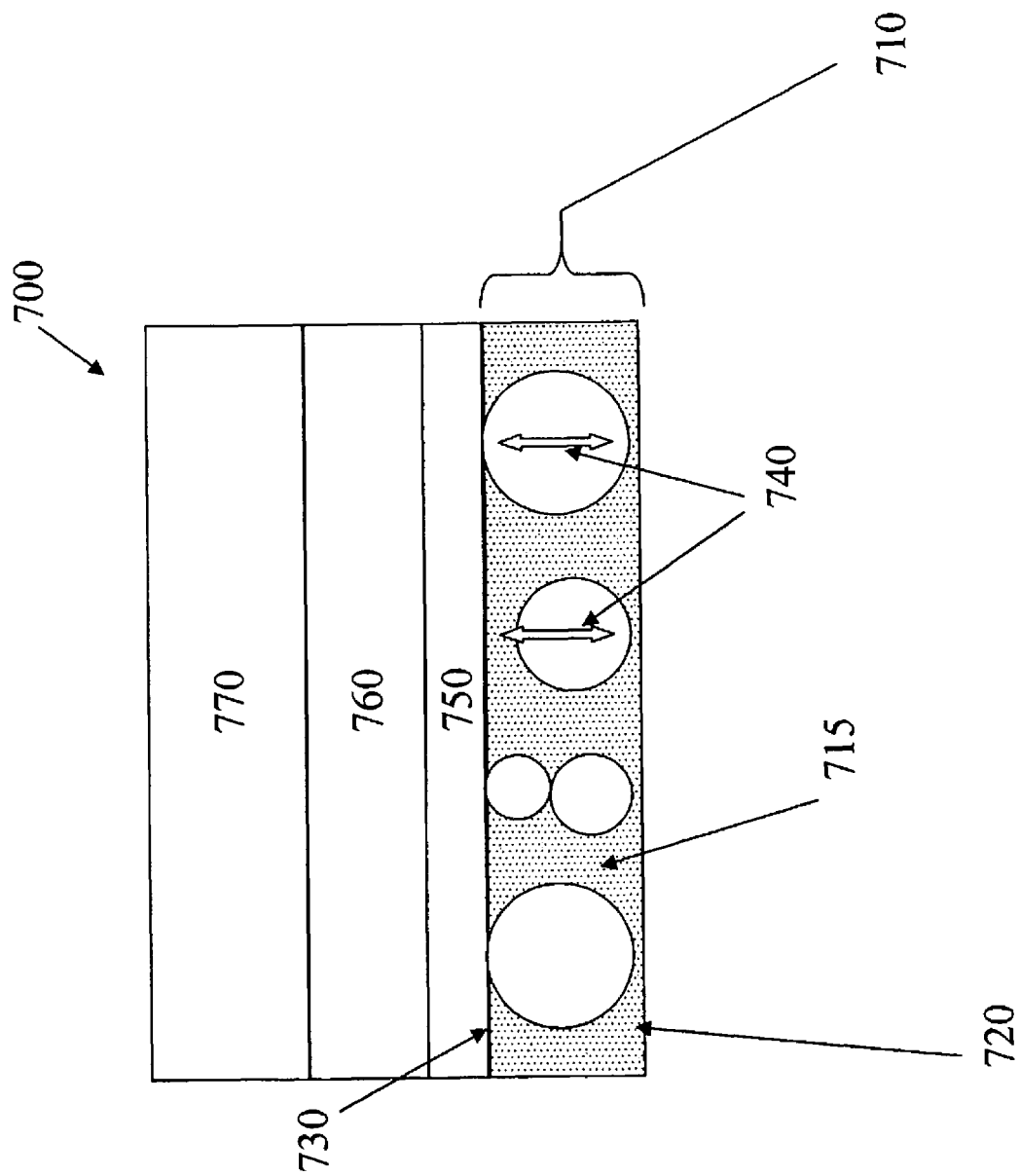
FIG. 12 shows a schematic cross-section of an embodiment of the present invention where the skin-contacting component comprises dissolvable beads that provide channels between the skin-contacting surface and the barrier.

In another embodiment, shown in FIG. 12, the present invention comprises a transdermal dosage form 700 comprising an active agent component which is a skin-contacting component 710 comprising a skin-contacting polymeric matrix 715 and an active agent, an adverse agent or reservoir component 760 comprising an adverse agent to the active agent, and a barrier 750. The skin-contacting component has a proximal, skin-contacting surface 720, a distal surface opposed to the skin-contacting surface 730, and channels 740 passing substantially entirely between the proximal and distal surfaces. The channels 740 connecting the skin-contacting surface 720 to the reservoir component 760 may be formed from one or more dissolvable, erodible, or porous beads imbedded within the skin-contacting polymeric matrix 715. One or more such beads may extend completely through the skin-contacting component 710. Alternatively, one or more beads may be adjacent to each other so as to effectively provide a channel through the skin-contacting component 710 in the presence of a solvent. The beads preferably extend from the proximal, skin-contacting surface 720 to the distal surface opposed to the skin-contacting surface 730, but it should be understood that insubstantial amounts of the skin-contacting polymeric matrix may be present on one or both sides of the bead(s). Thus, the channel may contain a small amount of the skin-contacting polymeric matrix 715, but will still provide substantially open passage to solvent. In one embodiment, the amount of skin-contacting polymeric matrix 715 within the channel 740 is of an insubstantial amount with a thickness of less than 5 µm. In another embodiment, the amount of skin-contacting polymeric matrix 715 within the channel 740 is less than about 1 µm.

A number of optional features may be included with any one of the embodiments described herein such as but not limited to an overlay backing, a porous medium, a release rate controlling membrane, additional components, and/or additional channels.

Figure 13A:
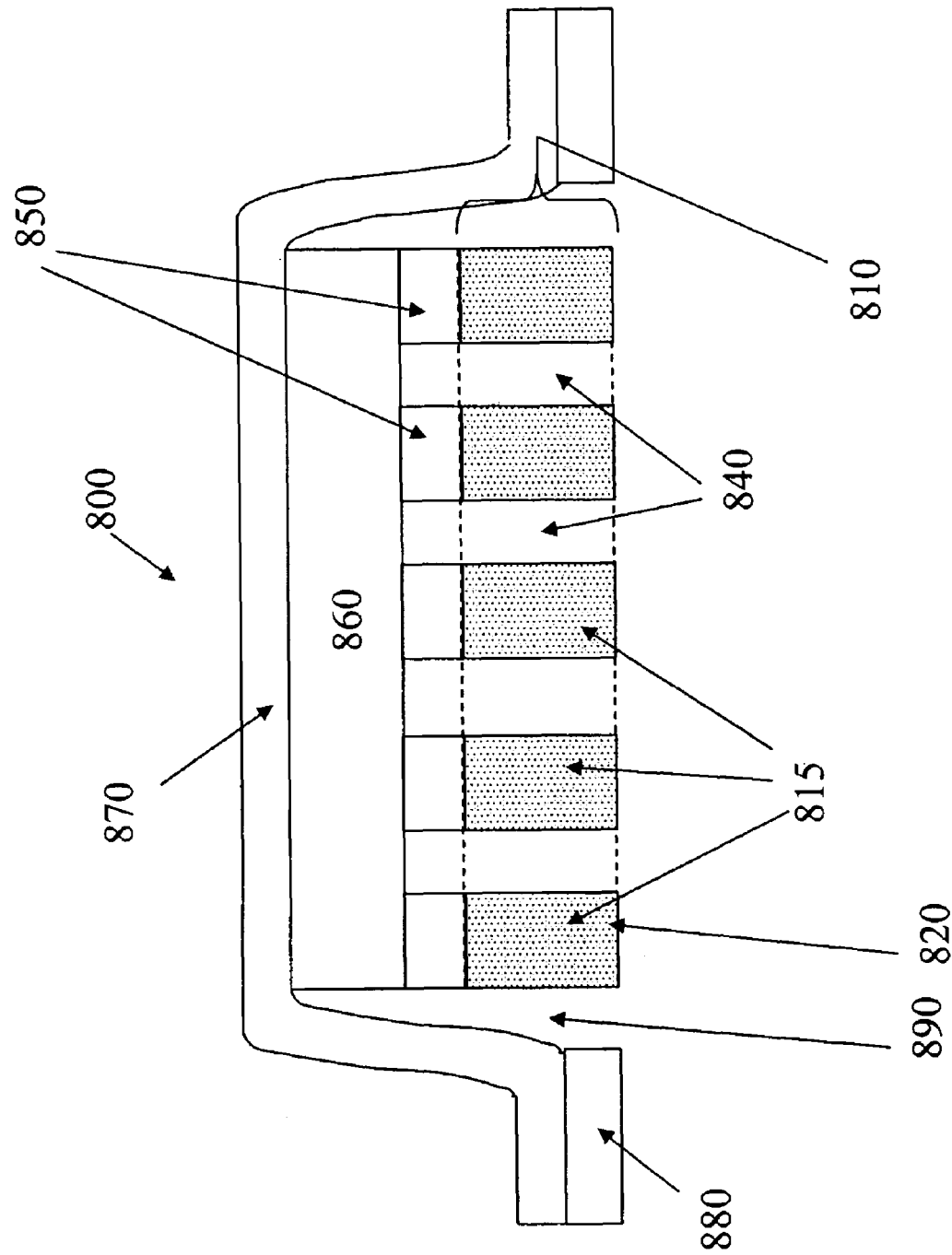
FIGS. 13a, b show a schematic cross-section (13a) and a plan view (13b) of an embodiment of the present invention where the skin-contacting component comprises a disk with a plurality of cylindrical air channels, the barrier comprises a disk with a plurality of cylindrical air channels, and the barrier is aligned with the skin-contacting component (as in FIG. 6a,b). In this embodiment the backing and an overlay PSA extend beyond the reservoir, barrier, and skin-contacting components.
Figure 13B:
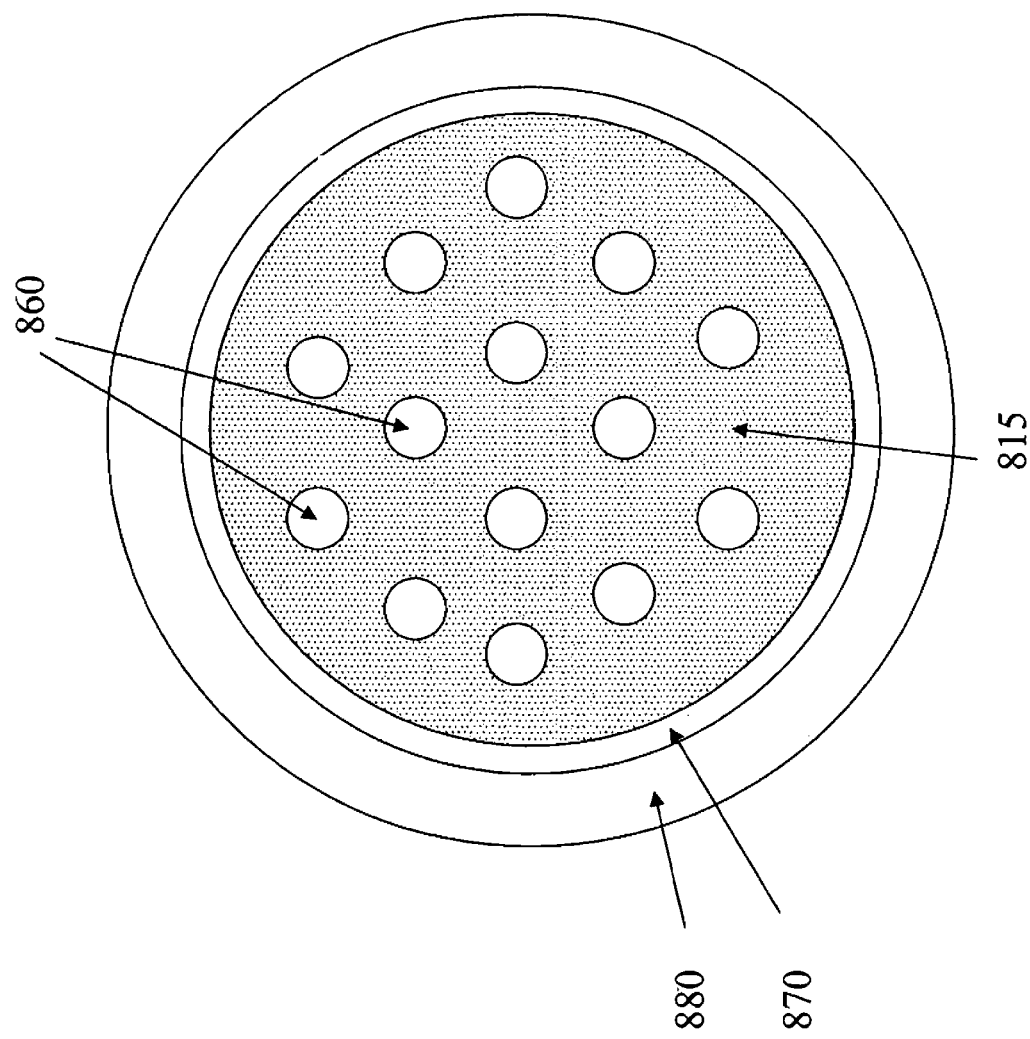

As shown in FIGS. 13a and 13b, an overlay backing 870 extends beyond the area of the adverse agent or reservoir component 860, barrier 850, and active agent or skin-contacting component 810 to a sufficient extent to allow the peripheral edge of overlay backing 870 to contact the skin surface of a patient. An additional channel or channels may also be present in the area between the overlay backing 870 and the adverse agent or reservoir component 860, barrier 850, and/or active agent or skin-contacting component 810.

The edges of the overlay backing 870 are coated with an overlay pressure sensitive adhesive (PSA) 880 that is used to secure the edges of the overlay backing 870 to a skin surface.

Any pressure sensitive adhesive suitable for use in skin-contacting applications, as previously described, can be used as the overlay PSA 880. Typical examples of flexible backing materials employed as conventional tape backings which may be useful for the present invention include those made of polymer films such as polypropylene; polyethylene, particularly low density polyethylene, linear low density polyethylene, metallocene polyethylenes, and high density polyethylene; polyvinyl chloride; polyester (e.g., polyethylene terephthalate); ethylene-vinyl acetate copolymer; polyurethane; cellulose acetate; and ethyl cellulose. Backings that are componented, such as polyethylene terephthalate-aluminum-polyethylene composites, are also suitable. Fabrics and nonwovens are also suitable. In a preferred embodiment, the overlay backing is a continuous polymeric film that prevents ingress of external moisture into the reservoir component from activities such as showering and bathing. Examples of such continuous films include polyurethane, polyethylene, and polyester.

In certain embodiments, the overlay backing 870 is large enough to define an air channel 890 between the periphery of the adverse agent component, the barrier and the active agent component and the inner periphery of the overlay PSA 880.

Figure 14:
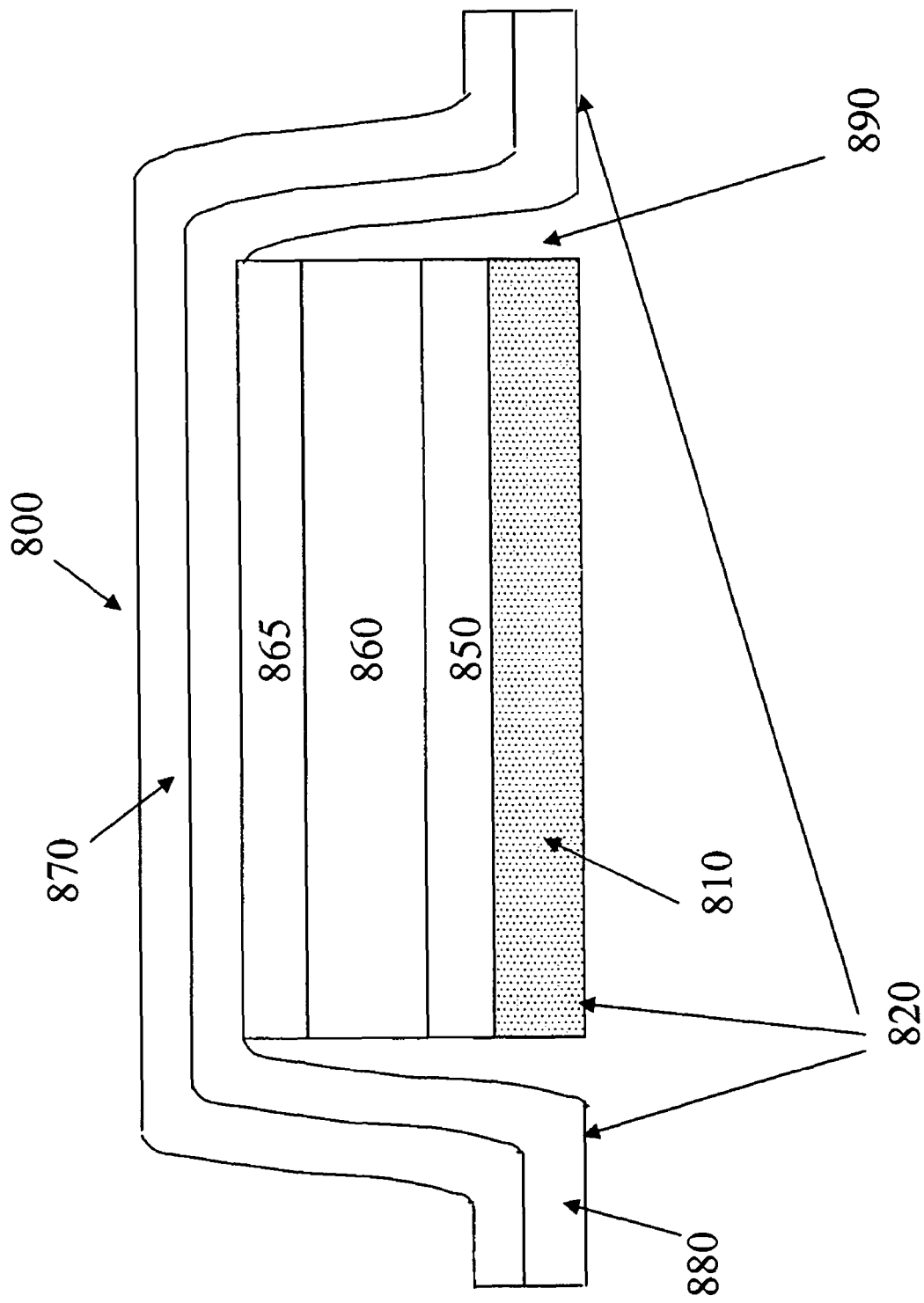
FIG. 14 shows a schematic cross-section of an embodiment of the present invention similar to that shown in FIG. 13a, except that the overlay PSA is coated uniformly across the backing, instead of being present only at the outer edges of the backing.

As shown in FIG. 14, the overlay backing 870 is continuously coated with an overlay pressure sensitive adhesive (PSA) 880 that is used to secure the edges of the overlay backing 870 to a skin surface. An additional, optional feature is a porous medium 865 included between the reservoir 860 and the overlay PSA 880. In this embodiment, the overlay PSA 880 serves a dual purpose. The area of the overlay PSA 880 extending beyond the area of the reservoir component 860, barrier 850, and active agent or skin-contacting component 810 serves to secure the dosage form to a skin surface and defines air channel 890. The area of the overlay PSA 880 that does not extend beyond the reservoir component 860 provides secure lamination of the overlay backing 870 to the porous medium 865 (or alternatively to the reservoir component 860 in dosage forms that do not have a porous component). Also, an additional channel or channels may be present in the area between the overlay backing 870 and the adverse agent or reservoir component 860, barrier 850, active agent or skin-contacting component 810, and/or porous medium 865.

The porous medium 865 can be any porous medium, such as a woven fabric, microporous film, or other open, mesh-like material. If the dosage form 800 is immersed in a solvent bath, then the porous medium 865 allows for fluid communication of the solvent with the top surface of the reservoir 860.

Figure 15:
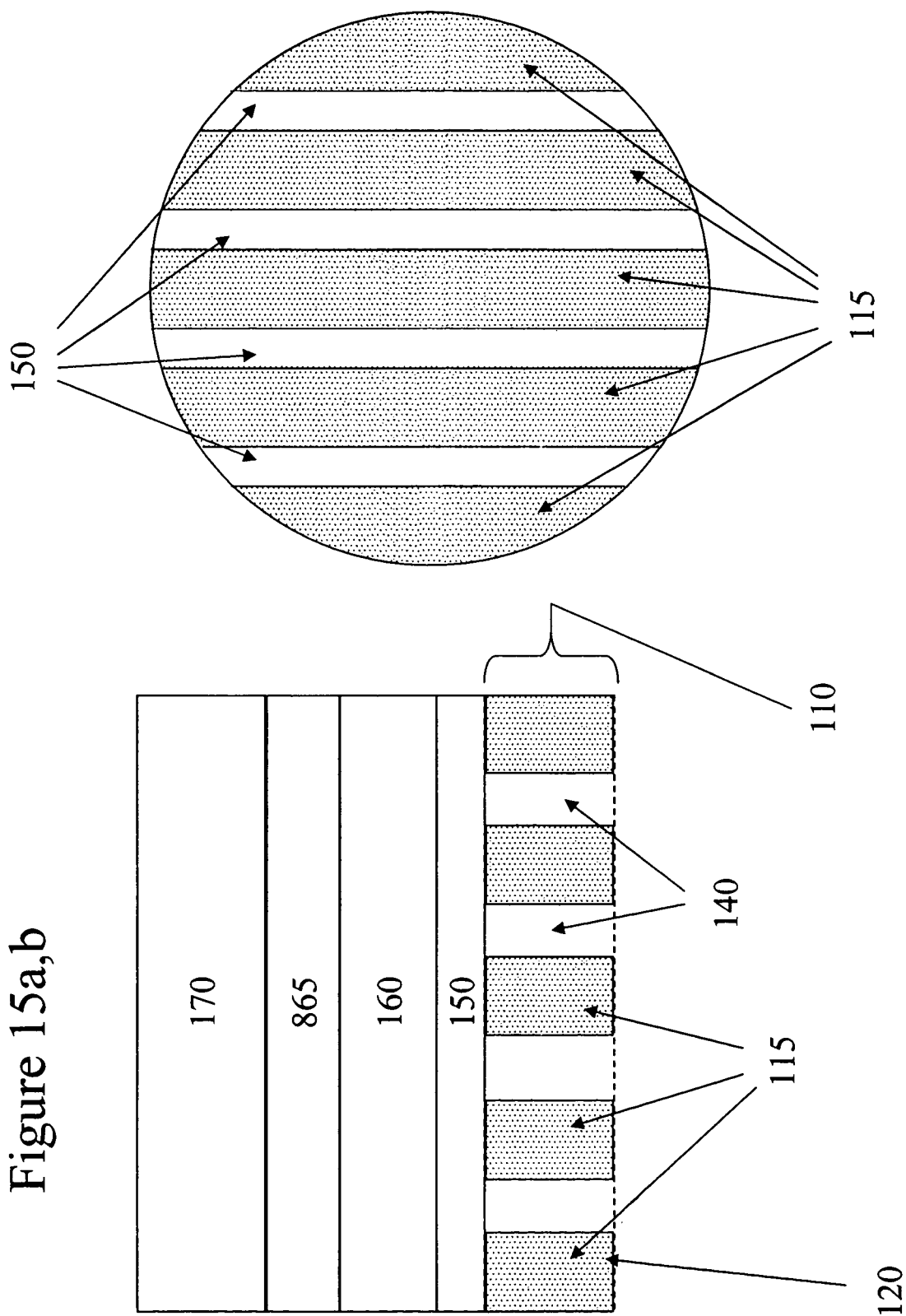
FIG. 15a, b show a schematic cross-section (15a) and a plan view (15b) of an embodiment of the present invention similar to that shown in FIG. 1a, b, except that a porous medium is interposed between the reservoir and backing components.

The porous medium 865 can be used in conjunction with an overlay backing 870, but it is not necessary to combine these optional features. For example, the porous medium 865 may also be present in a dosage form as shown in FIGS. 15a and 15b, where all of the features are the same as shown in FIGS. 1a and 1b, except that a porous medium 865 is inserted between the backing 170 and adverse agent or reservoir component 160.

The active agent component which may be a skin-contacting component, may comprise a number of additional components in addition to a polymeric material or matrix and an active agent. Additional components of the active agent or skin-contacting component can include skin penetration enhancers, drug solubilizers, plasticizers, anti-oxidants, colorants, and the like.

Examples of excipients useful as skin penetration enhancers or solubilizers in transdermal drug delivery systems include $C_8$-$C_{24}$ fatty acids such as isostearic acid, octanoic acid, and oleic acid; $C_8$-$C_{24}$ fatty alcohols such as oleyl alcohol and lauryl alcohol; lower alkyl esters of $C_8$-$C_{24}$ fatty acids such as ethyl oleate, isopropyl myristate, butyl stearate, and methyl laurate; monoglycerides of $C_8$-$C_{24}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); polyethylene glycol; propylene glycol; N,N-dimethyldodecylamine-N-oxide; terpenes, such as d-limonene, menthol, and terpineol.

In compositions of the active agent or skin-contacting component of the present invention, the skin penetration enhancers, drug solubilizers, plasticizers, and other additives can be dispersed or mixed, preferably substantially uniformly, and more preferably dissolved in the composition. Where the additive is a penetration enhancer, it is present in an amount that enhances active agent permeation through the skin compared to a like composition not containing the penetration enhancer(s) when this phenomenon is measured using a standard skin penetration model, such as set forth in U.S. Pat. No. 5,585,111 (Peterson), the disclosure of which is herein incorporated by reference in its entirety. In one embodiment, the total amount of penetration enhancer and solubilizer is less than about 40% by weight based on the total weight of the composition. In another embodiment, the total amount of penetration enhancer and solubilizer is less than about 30% based on the total weight of the composition.

Active agent or skin-contacting component compositions of the invention can be prepared by combining the polymer matrix, active agent, and optional additives, such as penetration enhancers, with an organic solvent (e.g., ethyl acetate, isopropanol, methanol, acetone, 2-butanone, ethanol, toluene, alkanes, and mixtures thereof) to provide a coating composition. The mixture is shaken or stirred until a homogeneous coating composition is obtained. The resulting composition is then applied to a release liner using conventional coating methods (such as but not limited to knife coating or extrusion die coating) to provide a predetermined uniform thickness of coating composition. Non-continuous or discontinuous coatings may be prepared using methods such as stripe coating, screen printing, and ink-jet printing.

Suitable release liners include conventional release liners comprising a known sheet material such as a polyester web, a polyethylene web, a polystyrene web, or a polyethylene-coated paper coated with a suitable fluoropolymer or silicone based coating. The release liner that has been coated with the composition is then dried and laminated onto a barrier component using conventional methods. An optional tie component, heat, and/or pressure may be used to connect the skin-contacting component with the barrier component. In addition, the skin-contacting component compositions may be directly coated onto the barrier component and subsequently dried and laminated to a release liner.

When the adverse agent or reservoir component comprises a pressure-sensitive adhesive or similar polymeric material or matrix, then the adverse agent or reservoir component compositions of the invention can be prepared using methods similar to those for preparing the active agent or skin-contacting component, with the exception that an adverse agent is used in place of the active agent to prepare the coating composition. Alternatively, the adverse agent or reservoir component can comprise a porous medium, such as a porous or microporous film. The adverse agent can be dissolved in an impregnating solvent and the porous or microporous film is soaked in the solvent for a sufficient period of time to allow the adverse agent to penetrate the pores of the film. The solvent is then dried leaving the adverse agent dispersed or mixed throughout the film. The reservoir component is laminated to the barrier side of the barrier/skin-contacting multi-laminate, optionally using heat, pressure, and/or an additional tie component to ensure adequate contact between the reservoir component and barrier.

A backing is laminated to the surface of the adverse agent or reservoir component opposed to the barrier, optionally using heat, pressure and/or an additional tie component to ensure adequate contact between the reservoir component and backing. One skilled in the art will appreciate that it may be preferred to vary the order of lamination steps depending on the types and thickness of the components comprising the dosage form.

The transdermal dosage forms of the invention can be made in the form of an article such as a tape, a patch, a sheet, a dressing or any other form known to those skilled in the art. Generally, the dosage form will be in the form of a patch of a size suitable to deliver a preselected amount of active agent through the skin.

In one embodiment, the dosage form has a surface area greater than about 1 $cm^2$. In another embodiment, the dosage form has a surface area greater than about 5 $cm^2$. In another embodiment, the dosage form has a surface area greater than 10 $cm^2$. In another embodiment, the dosage form has a surface area less than about 100 $cm^2$. In another embodiment, the dosage form has a surface area less than about 40 $cm^2$.

Dosage forms of the present invention typically comprise a release liner that covers and protects the skin-contacting surface prior to use by a patient. Suitable release liners include conventional release liners comprising a known sheet material such as a polyester web, a polyethylene web, a polypropylene web, or a polyethylene-coated paper coated with a suitable fluoropolymer or silicone based coating. Dosage forms of the present invention are typically packaged individually in a foil-lined pouch for storage. Dosage forms of the present invention may alternatively be provided in a rolled or stacked form suitable for use with a dispensing apparatus.

In certain embodiments, dosage forms of the present invention are typically packaged individually in a foil-lined pouch for storage. Dosage forms of the present invention may alternatively be provided in a rolled or stacked form suitable for use with a dispensing apparatus.

Figure 16:
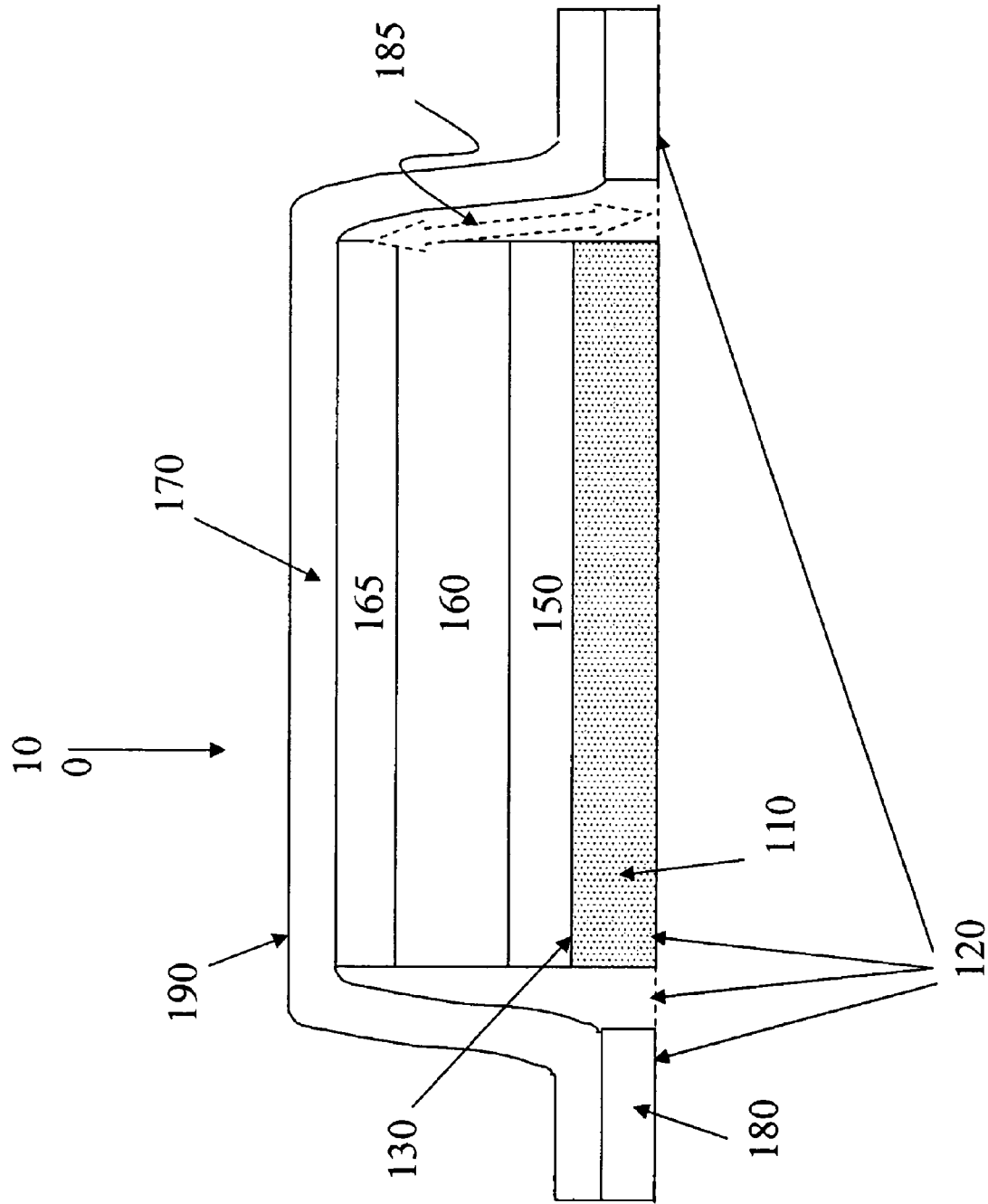
FIG. 16 shows a schematic cross-section of an embodiment of the present invention with a barrier between the active agent component and the adverse agent reservoir, and where the porous medium is adjacent to the overlay backing.

In one embodiment, shown in FIG. 16, the present invention comprises a transdermal dosage form 100 comprising an active agent component 110, which can be a skin-contacting component comprising a skin-contacting polymeric material and an active agent, an antagonist or adverse agent reservoir 160 comprising an adverse agent to the active agent, a barrier 150, and a porous medium or material 165. The active agent component defines a proximal or skin-contacting surface 120 and has a distal surface 130 opposed to, i.e., opposite to or in contraposition to, the proximal surface. The barrier 150 is present as a component that is adjacent to the distal surface of the active agent component 130 and the adverse agent reservoir 160. The porous medium or material 165 is adjacent to the adverse agent reservoir 160. An overlay backing 170 is adjacent to the porous medium 165 and provides an outer surface 190 of the dosage form 100.

The porous medium 165 is in fluid communication with the proximal surface 120. Fluid communication is meant to indicate that liquid may flow freely between the proximal surface 120 and the porous medium 165. That is, if the dosage form is immersed in a liquid such that the proximal surface is in contact with the liquid, then the liquid will also be able to contact the porous medium 165. The two-sided arrow 185 in FIG. 16 shows an area of fluid communication between the proximal surface 120 and the porous medium 165. One of the functions of the porous medium or material 165 can be to provide capillary force to the surface of the adverse agent layer in the presence of a liquid.

The active agent component 110 comprises a polymeric material and an active agent. The active agent is preferably dispersed homogeneously throughout the polymeric material, and more preferably dissolved within the polymeric material. The proximal or skin-contacting surface 120 should be sufficiently conformable when placed on a skin surface so as to make intimate contact with at least a portion of the skin surface. In one embodiment, substantially all of the polymeric material at the proximal surface 120 will make intimate contact with the skin surface.

In one embodiment, the active agent component has a thickness of no less than about 10 μm. In another embodiment, the active agent component has a thickness of no less than about 20 μm. In another embodiment, the active agent component has a thickness of no less than about 50 μm. In another embodiment, the active agent component has a thickness of no greater than about 250 μm. In another embodiment, the active agent component has a thickness of no greater than about 200 μm. In another embodiment, the active agent component has a thickness of no greater than about 150 μm.

In one embodiment, an active agent component of the present invention is a continuous, planar component in the form of a slab. In another embodiment, the active agent component may be structured or comprise channels, such that the polymeric material of the active agent component is discontinuous. Suitable active agent components can include a plurality of strips, wherein the strips are separated by channels; an annular disk with a central channel filled with air or any inert gas; and a disk with a plurality of cylindrical air channels.

The polymeric material of the active agent component comprises a polymer, preferably a polymer selected from the group consisting of acrylates, natural rubbers, polyisobutylenes, polyisoprenes, styrenic block copolymers, polyvinylethers, silicone polymers, polyurethanes, polyurethane-ureas, and mixtures thereof. The polymers can be present alone or in combination. The polymeric material may optionally contain other additives well-known to those in the art, for example, penetration enhancers, tackifiers, plasticizers, antioxidants, colorants, and the like.

In one embodiment, the polymeric material of the active agent component may comprise a pressure-sensitive adhesive. Preferred pressure-sensitive adhesives for use in the dosage forms of the invention include acrylates, polyisobutylenes, silicone polymers, and mixtures thereof. Examples of useful polyisobutylene pressure-sensitive adhesives are described in U.S. Pat. No. 5,985,317 (Venkateshwaran et al.), the disclosure of which is incorporated herein by reference in their entirety for all purposes. Examples of useful acrylate and silicone polymer pressure-sensitive adhesives, and mixtures thereof, are described in U.S. Pat. No. 5,474,783 (Miranda et al.), U.S. Published Patent Application No. 2002/0119187 A1 (Cantor et al.) and U.S. Published Patent Application No. 2003/0026829 A1 (Venkatraman et al.), the disclosures of which is incorporated herein by reference in their entirety for all purposes.

Acrylate polymers and copolymers are particularly preferred pressure-sensitive adhesives. Examples of suitable monomers for use in acrylate copolymers include alkyl acrylates, such as isooctyl, 2-ethylhexyl, n-butyl, ethyl, methyl, and dimethylhexyl, and alkyl methacrylates, such as lauryl, isodecyl, and tridecyl. Monomers containing functional groups, such as carboxylic acid, hydroxy, amide, and amino may also be incorporated into an acrylate copolymer. Examples of suitable monomers containing functional groups include acrylic acid, hydroxyalkyl acrylates containing 2 to 4 carbon atoms in the hydroxyalkyl group, acrylamide, N-vinyl-2-pyrrolidone, vinyl acetate, and alkoxyethyl acrylate in its entirety for all purposes.

Acrylate copolymers may optionally further comprise a substantially linear macromonomer copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference in its entirety for all purposes.

Other polymer materials of the active agent component may include but are not limited to polyethylene; polypropylene; ethylene/propylene copolymers; ethylene/ethylacrylate copolymers; ethylene/vinyl acetate copolymers; silicone elastomers, especially the medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly(ethylene terephthalate); butyl rubber; epichlorohydrin rubber; ethylene-vinyl alcohol copolymer; ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methylcellulose, and cellulose esters; polycarbonates; polytetrafluoroethylene; and combinations thereof. In one embodiment, the polymer matrix has a glass-transition temperature below room temperature. The polymer can, but need not necessarily, have a degree of crystallinity at room temperature. Cross-linking monomeric units or sites can be incorporated into the polymers. For example, cross-linking monomers can be incorporated into polyacrylate polymers. The cross-linking monomers provide sites for cross-linking the polymer matrix after microdispersing the active agent into the polymer. Known cross-linking monomers for polyacrylate polymers include, but are not limited to, polymethacrylic esters of polyols such as butylene diacrylate and dimethacrylate, trimethylol propane trimethacrylate, and the like. Other monomers that provide cross-linking sites include allyl acrylate, allyl methacrylate, diallyl maleate, and the like.

The active agent of the present invention may be any drug substance that is capable of being abused. Many drugs have a potential for abuse, and include, for example, narcotics, such as morphine, fentanyl, codeine, sufentanil, and oxycodone; psychostimulants, such as amphetamine, methamphetamine, and methylphenidate; methoxy substituted amphetamines, such as 3,4-methylenedioxymethamphetamine (MDMA); and benzodiazepines, such as diazepam, oxazepam, and lorazepam.

The active agent will be present in an amount such that the composition delivers a therapeutically effective amount for the condition being treated. This amount will vary according to the type of active agent used, the condition to be treated, the amount of time the composition is allowed to remain in contact with the skin of the subject, and other factors known to those of skill in the art. For example, information on dosing and the amount of opioid agonist active agent present in a transdermal dosage form is set forth in U.S. Published Patent Application No. 2002/0119187 A1, filed Sep. 26, 2001, entitled "Composition for the Transdermal Delivery of Fentanyl" by Cantor et al. and U.S. Published Patent Application No. 2003/0026829 A1, filed Mar. 15, 2002, entitled "Transdermal Administration of Fentanyl and Analogs Thereof" by Venkatraman et al. each of which are incorporated by reference herein in their entirety for all purposes. In one embodiment, the amount of active agent present in the transdermal drug delivery composition of the invention is greater than about 0.01 wt-%, based on the total weight of the composition of the active agent component. In another embodiment, the amount of active agent present in the transdermal drug delivery composition of the invention is greater than about 1.0 wt-%, based on the total weight of the composition of the active agent component. In another embodiment, the amount of active agent present in the transdermal drug delivery composition of the invention is less than about 40 wt-%, based on the total weight of the composition of the active agent component. In another embodiment, the amount of active agent present in the transdermal drug delivery composition of the invention is less than about 20.0 wt-%, based on the total weight 16 of the composition of the active agent component.

In FIG. 1, the adverse agent reservoir 160 is connected on one side to a barrier 150 component and on the other side to the porous medium 165. The reservoir may be a polymeric material, porous film, or other component suitable for containing an adverse agent. Preferably, the adverse agent reservoir 160 is capable of containing a sufficient amount of adverse agent to blunt or block at least one biological effect of the active agent or to cause at least one unpleasant side effect in a patient or animal which has absorbed the total amount of active agent in the dosage form 100. This amount can vary according to the amount and type of active agent in the dosage form. The adverse agent component comprises an adverse agent in any form or composition or reservoir which allows the adverse agent to be at least partially extracted in the presence of a solvent, including but not limited to, water, ethanol or ether, or mixtures thereof. In certain embodiments, the adverse agent can be dispersed in a polymeric material, including but not limited to, the polymeric materials which are suitable for incorporation into the active agent component.

Suitable polymeric materials or matrices for use in the adverse agent component include, but are not limited to, acrylates, natural rubbers, and/or polyisobutylenes, polyisoprenes, styrenic block copolymers, polyvinylethers, silicone polymers, polyurethanes, polyurethane-ureas, and mixtures thereof. In one embodiment, the adverse agent is preferably dispersed substantially homogeneously throughout a polymeric material. In one embodiment, the adverse agent is preferably dispersed substantially homogeneously throughout a polymeric material. In one embodiment, the adverse agent is dissolved in the polymeric material. In another embodiment, the adverse agent component includes solid crystals of adverse agent dispersed throughout the polymeric material. In certain embodiments, the polymeric matrix is preferably a pressure sensitive adhesive. Suitable pressure-sensitive adhesives include those suitable for use as the polymeric material of the active agent component. Additionally, pressure-sensitive adhesives that are not suitable for direct skin contact can be suitable for use as the polymeric material of the adverse agent.

The adverse agent component can also comprise a porous medium or material, such as a woven fabric, porous or microporous film, or other open, mesh-like material, wherein at least a portion of the pores contain adverse agent. The adverse agent can be present within the pores in any form, including but not limited to a liquid, a gel or a solid, such as a solid crystalline or powdered material. For example, the adverse agent can be mixed with a carrier, such as a viscous liquid, semi-solid or gel material. Examples of suitable materials for incorporation into the adverse agent component include, but are not limited to, microporous films formed by extruding polyethylene or polypropylene with mineral oil as described in U.S. Pat. No. 4,539,256 (Shipman), the disclosure of which is incorporated herein by reference in its entirety for all purposes.

Other polymer materials of the adverse agent component may include but are not limited to polyethylene; polypropylene; ethylene/propylene copolymers; ethylene/ethylacrylate copolymers; ethylene/vinyl acetate copolymers; silicone elastomers, especially the medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly(ethylene terephthalate); butyl rubber; epichlorohydrin rubber; ethylene-vinyl alcohol copolymer; ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methylcellulose, and cellulose esters; polycarbonates; polytetrafluoroethylene; and combinations thereof. In one embodiment, the polymer matrix has a glass-transition temperature below room temperature. The polymer can, but need not necessarily, have a degree of crystallinity at room temperature. Cross-linking monomeric units or sites can be incorporated into the polymers. For example, cross-linking monomers can be incorporated into polyacrylate polymers. The cross-linking monomers provide sites for cross-linking the polymer matrix after microdispersing the adverse agent into the polymer. Known cross-linking monomers for polyacrylate polymers include, but are not limited to, polymethacrylic esters of polyols such as butylene diacrylate and dimethacrylate, trimethylol propane trimethacrylate, and the like. Other monomers that provide cross-linking sites include allyl acrylate, allyl methacrylate, diallyl maleate, and the like. In one embodiment the polymer matrix does not allow any, or any detectable amount, of an adverse agent to diffuse out of it, particularly in those instances in which the adverse agent can penetrate a patient's skin.

In one embodiment, the adverse agent component has a thickness of no less than about 10 μm. In another embodiment, the adverse agent component has a thickness of no less than about 20 μm. In another embodiment, the adverse agent component has a thickness of no less than about 50 μm. In another embodiment, the adverse agent component has a thickness of no greater than about 250 μm. In another embodiment, the adverse agent component has a thickness of no greater than about 200 μm. In another embodiment, the adverse agent component has a thickness of no greater than about 150 μm.

The barrier 150 shown in FIG. 16 is a component that is adjacent to the distal surface of the active agent component 130 on one side and the adverse agent reservoir 160 on the other side. The barrier is permeable to and/or at least partially soluble in a solvent selected from the group consisting of water, ethanol, ether, and mixtures thereof, and the barrier is substantially impermeable to diffusion of active agent and adverse agent in the absence of said solvent. In certain embodiments, the barrier can be a dissolvable film.

In relation to the present invention, impermeability of the barrier to diffusion of active agent and adverse agent is defined such that only insignificant amounts, and preferably none, of active agent or adverse agent are able to diffuse across the barrier during ordinary use or storage of the dosage form. The precise amount that is insignificant will vary depending on the particular application for the dosage form, but it will be understood to include any amounts of active agent or adverse agent that do not significantly alter the therapeutic effect of the dosage form (e.g., the active agent concentration in the active agent component does not change significantly due to diffusion of active agent across the barrier and a pharmacologically effective amount of adverse agent does not diffuse across the barrier and into the active agent component). Any insignificant amounts of active agent or adverse agent that may diffuse across the barrier are preferably less than 5%, more preferably less than 1%, and most preferably less than 0.1% by weight of the total active agent in the dosage form. Any insignificant amounts of active agent or adverse agent that may diffuse across the barrier will preferably do so over a time period greater than 1 month, more preferably greater than 6 months, and most preferably greater than 2 years.

Suitable barriers can be films comprised of but not limited to polyesters such as polyethylene terephthalate; polypropylenes; and polyethylenes such as high density polyethylene. Suitable barriers can also be multi-componented films comprised of but not limited to polyethylene terephthalate-aluminum-polyethylene composites or polyethylene terephthalate-ethylene vinyl acetate composites. Other barriers can be comprised of polyperfluorocarbon. Other barriers may be comprised of a plasticizer and/or a polymer based material including but not limited to a cellulose polymer, such as hydroxypropyl methylcellulose, hydroxypropyl cellulose or hydroxyethyl cellulose, and/or polyvinylpyrolidine. The hydroxyethyl cellulose may be NATROSOL® 250 HNF (available from the Aqualon Division of Hercules Inc., Wilmington, Del.). The hydroxypropyl cellulose may be KLUCEL® HXAF (available from the Aqualon Division of Hercules Inc.). The plasticizer may be a compound such as but not limited to triethanolamine, triacetin, glycerol monooleate, polyethyleneglycol 600, levulinic acid, and/or mixtures thereof.

In one embodiment, the barrier thickness is greater than about 1 μm. In another embodiment, the barrier thickness is greater than about 10 μm. In another embodiment, the barrier thickness is greater than about 20 μm. In another embodiment, the barrier thickness is less than about 100 μm. In another embodiment, the barrier thickness is less than about 80 μm. In another embodiment, the barrier thickness is less than about 75 μm. In another embodiment, the barrier thickness is less than about 60 μm. In another embodiment, the barrier thickness is less than about 50 μm.

Barriers of the present invention may be formed having a discontinuous structure that can be subsequently laminated or otherwise attached to the discontinuous structure of the active agent component. It is preferred that the barrier and the polymeric material or matrix of the active agent component are fully aligned. It is not necessary for the two components to be completely registered, however, as long as the barrier serves to deter diffusion of the active agent and adverse agent through the barrier component. Discontinuous barriers of the present invention may also be formed at the same time that the discontinuities in the polymeric material or matrix of the active agent component are formed. For example, a continuous barrier film may be coated with a continuous skin-contacting polymeric matrix or laminated to a continuous skin-contacting polymeric matrix. Apertures or holes may be created in the laminate using any suitable hole-forming process, such as punching, so that aligned apertures are simultaneously created in both the barrier and the skin-contacting polymeric matrix.

Barriers of the present invention can also comprise an impermeable surface coating applied to one of the other surfaces present in the dosage form, such as the distal surface of the active agent component, which is opposed to the skin-contacting surface, or the or surface of the adverse agent component facing the active agent component. Examples of suitable coatings include fluoropolymers, such as polymers or copolymers of tetrafluoroethylene, hexafluoropropylene, and/or vinylidene fluoride. Terpolymers of tetrafluoroethylene, hexafluoropropylene, and vinylidene fluoride, such as Dyneon™ fluorothermoplastic THV are preferred coatings. In one embodiment, the thickness of impermeable surface coating is from about 0.5 to about 10 μm. In another embodiment, the thickness of impermeable surface coating is from about 1 to about 5 μm. In another embodiment, the thickness of impermeable surface coating is from about 2 to about 4 μm. In another embodiment, the barrier is a thin coating on the surface of a microporous film reservoir or adverse agent component.

In one embodiment, the barrier of the present invention is a continuous, planar component in the form of a slab. In another embodiment, the barrier may be patterned or comprise channels, such that the barrier is discontinuous. Suitable barriers can include a plurality of strips wherein the strips are separated by channels, an annular disk with a central channel filled with air or any inert gas, and a disk with a plurality of cylindrical air channels.

A number of optional features may be included with any one of the embodiments described herein such as but not limited to an overlay backing, a release rate controlling membrane, channels, and/or additional components.

As shown in FIG. 16, an overlay backing 170 extends beyond the area of the adverse agent or reservoir component 160, barrier 150, and active agent component 110 to a sufficient extent to allow the peripheral edge of overlay backing 170 to contact the skin surface of a patient. An additional channel or channels may also be present in the area between the overlay backing 170 and the periphery of the adverse agent or reservoir component 160, barrier 150, and/or active agent component 110.

The peripheral edges of the overlay backing 170 are coated with an overlay pressure sensitive adhesive (PSA) 180 that is used to secure the edges of the overlay backing 170 to a skin surface. Any pressure sensitive adhesive suitable for use in skin-contacting applications, as previously described, can be used as the overlay PSA 180. Typical examples of flexible backing materials employed as conventional tape backings which may be useful for the present invention include those made of polymer films such as polypropylene; polyethylene, particularly low density polyethylene, linear low density polyethylene, metallocene polyethylenes, and high density polyethylene; polyvinyl chloride; polyester (e.g., polyethylene terephthalate); ethylene-vinyl acetate copolymer; polyurethane; cellulose acetate; and ethyl cellulose. Backings that are componented, such as polyethylene terephthalate-aluminum-polyethylene composites, are also suitable. Fabrics and non-wovens are also suitable. In a preferred embodiment, the overlay backing is a continuous polymeric film that prevents ingress of external moisture into the adverse agent component from activities such as showering and bathing. Examples of such continuous films include polyurethane, polyethylene, and polyester.

In certain embodiments, the overlay backing 170 is large enough to define an air channel number between the periphery of the adverse agent component, the barrier and the active agent component and the inner periphery of the overlay PSA 180.

Figure 18:
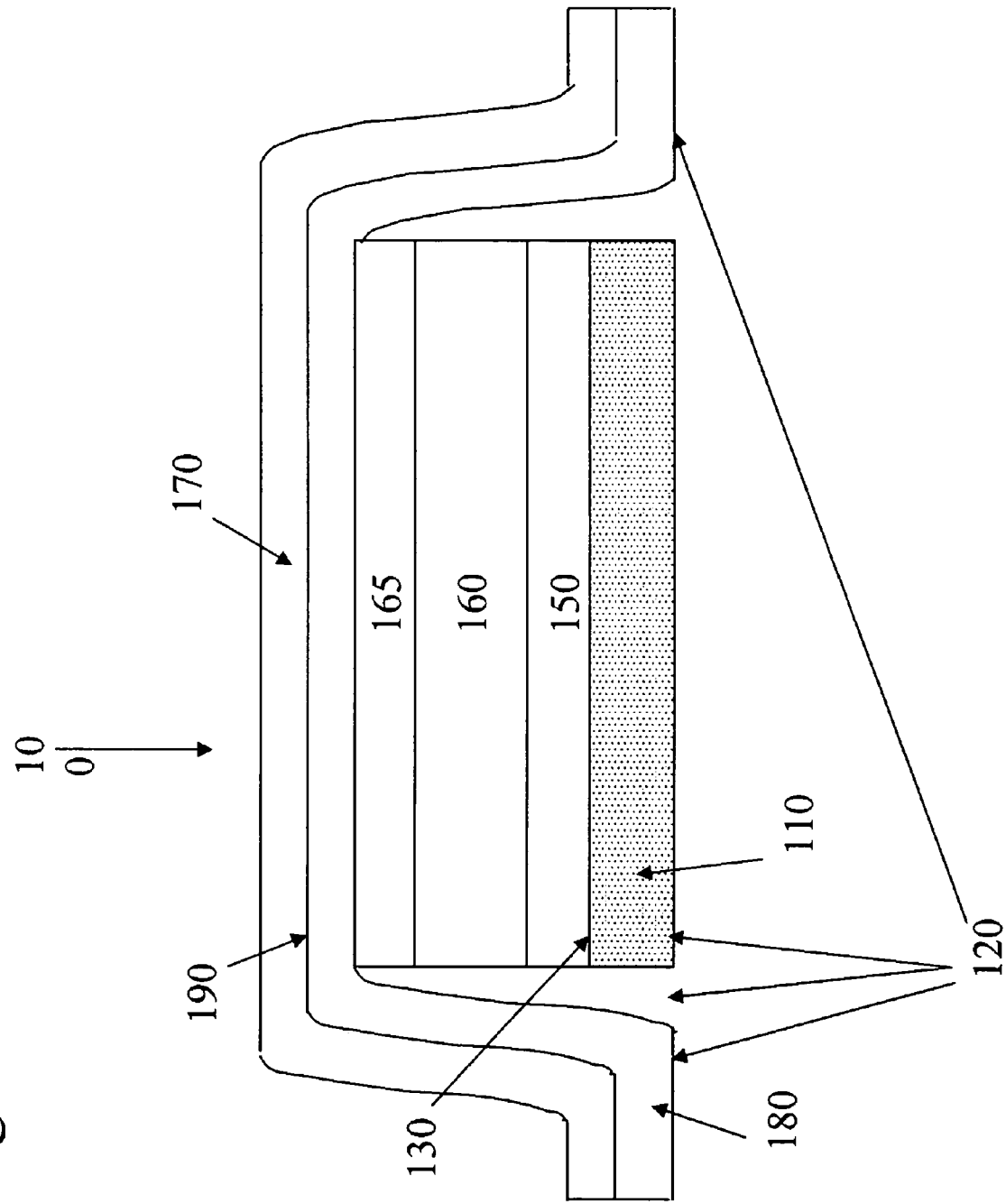
FIG. 18 shows a schematic cross-section of an embodiment of the present invention similar to FIG. 16, except that the overlay PSA is coated uniformly across the overlay backing, instead of being present only at the outer edges of the overlay backing.

As shown in FIG. 18, the overlay backing 170 is continuously coated with an overlay pressure sensitive adhesive (PSA) 180 that is used to secure the edges of the overlay backing 170 to a skin surface. In this embodiment, the overlay PSA 180 serves a dual purpose. The area of the overlay PSA 180 extending beyond the area of the porous medium 165, adverse agent reservoir 160, barrier 150, and active agent component 110 serves to secure the dosage form to a skin surface. The area of the overlay PSA 180 that does not extend beyond the adverse agent or reservoir component 160 provides secure lamination of the overlay backing 170 to the porous medium 165. An optional barrier component may be placed between the overlay PSA 180 and the porous medium 165 in order to prevent any interaction between the overlay PSA 180 and the porous medium 165. This optional component is preferably a flexible backing material as described above and is more preferably a polyethylene film.

The porous medium 165 is a material or construct characterized in that it has openings that allow the passage or absorption of liquids. Examples of a porous medium include microporous films, such as microporous films formed by extruding polyethylene or polypropylene with mineral oil as described in U.S. Pat. No. 4,539,256 (Shipman); fibrous webs; woven fabrics and textiles; open-cell foams; grooved films; and other open, mesh-like materials. A porous medium may have the appearance of a solid matrix characterized by a fine network of microscopic openings. In another aspect, it may be a structured slab or film having channels or grooves that allow the passage of liquid. It should be understood that certain structures with open channels or grooves will act as a porous medium when the open channels or grooves are adjacent to another component, such as the adverse agent reservoir.

As shown in FIG. 16, the porous medium 165 is adjacent to the adverse agent reservoir 160, such that if the dosage form 100 is immersed in a solvent bath, then the porous medium 165 allows for fluid communication of the solvent with the top surface of the reservoir 160. The porous medium 165 may align with the adverse agent reservoir 160. Alternatively, the porous medium 165 may extend beyond the area of the adverse agent reservoir 160 and may fill part or all of the void area shown in FIG. 16 where the fluid communication between the porous medium 165 and the skin-contacting surface 120 takes place.

Figure 19:
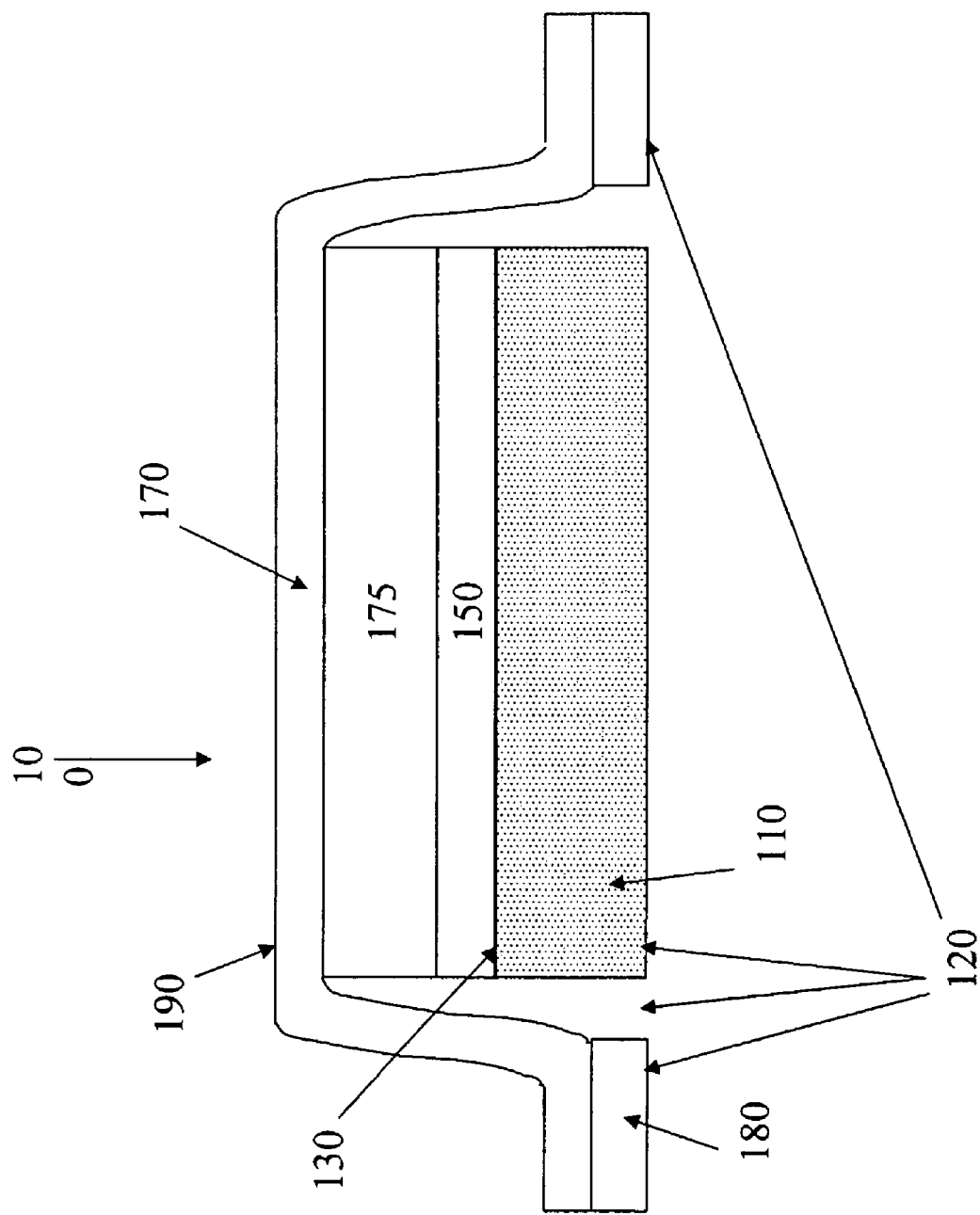
FIG. 19 shows a schematic cross-section of an embodiment of the present invention with a barrier between the active agent component and the adverse agent reservoir, and where the porous medium serves as the adverse agent reservoir.

In an alternative embodiment, shown in FIG. 19, the porous medium and adverse agent reservoir may form a single integral component 175 of the dosage form. That is, the porous medium may serve as the carrier matrix of the adverse agent reservoir.

Figure 17:
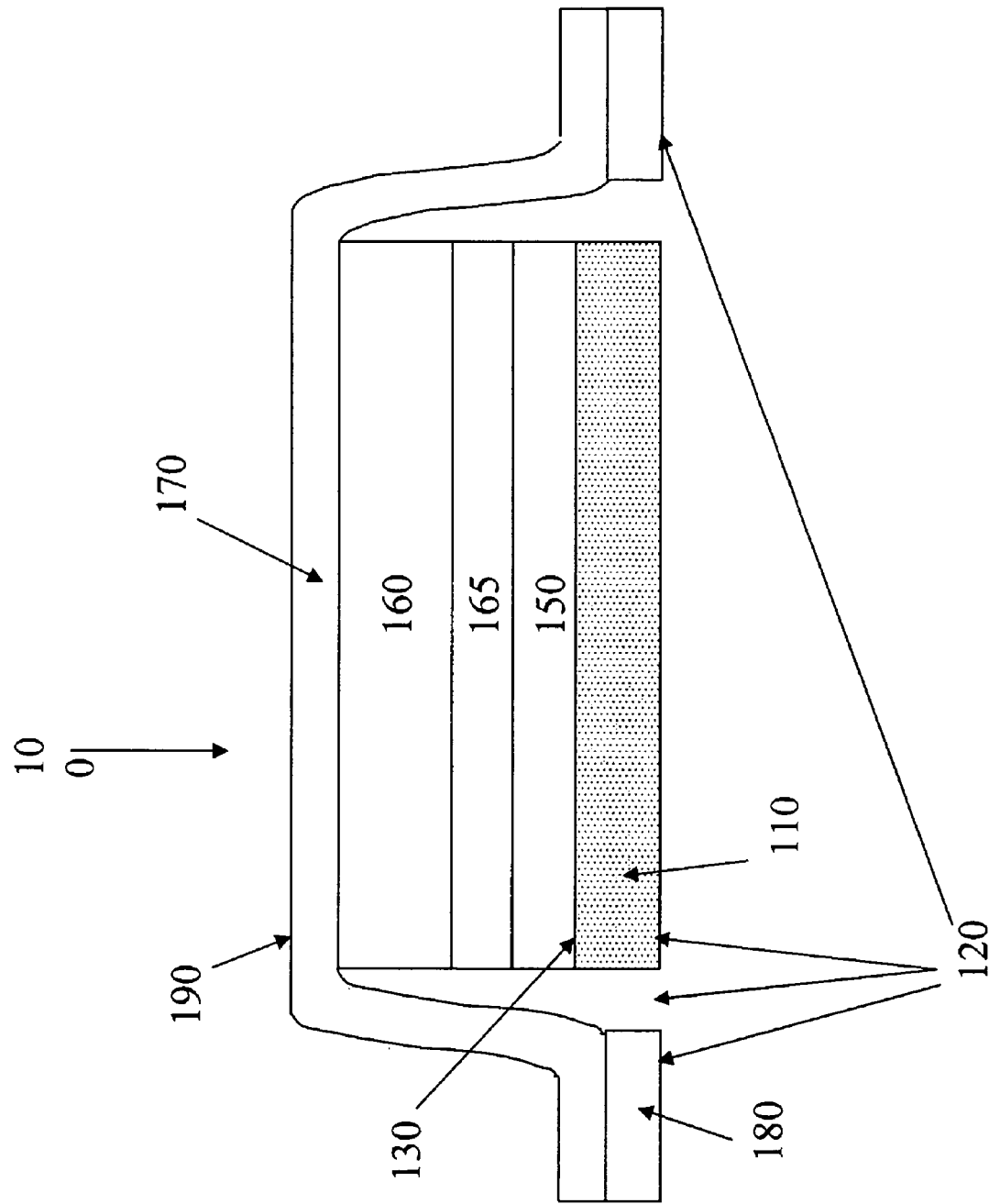
FIG. 17 shows a schematic cross-section of an embodiment of the present invention with a barrier between the active agent component and the porous medium, and where the adverse agent reservoir is adjacent to the overlay backing.

As shown in FIG. 17, the adverse agent reservoir 160 may be adjacent to the overlay backing 170, and the porous medium 165 is interposed directly between the adverse agent reservoir 160 and the barrier 150. Furthermore, the porous medium need not be present as a distinct component in contact with a major surface of the adverse agent reservoir, so long as the porous medium is adjacent to the adverse agent reservoir and is in fluid communication with the active agent component. Thus, for example, the porous medium may be an annular disk surrounding a central adverse agent reservoir, an interpenetrating network within the adverse agent reservoir, or other like configurations.

Figure 20:
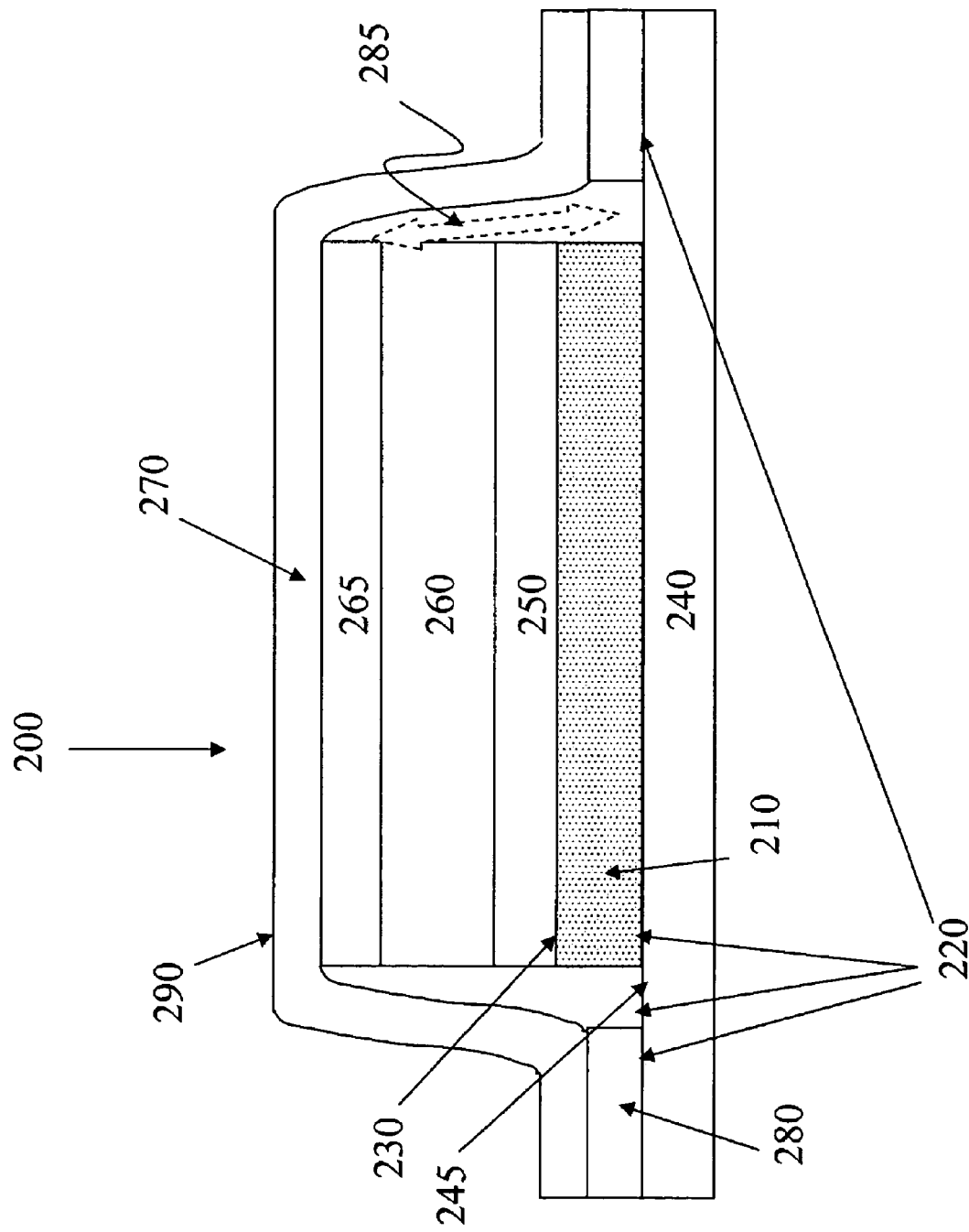
FIG. 20 shows a schematic cross-section of an embodiment of the present invention with a barrier between the active agent reservoir and the adverse agent reservoir, and where the active agent reservoir is adjacent to the barrier and the release liner.

In another embodiment, shown in FIG. 20, the present invention comprises a transdermal dosage form 200 comprising a release liner 240, an overlay backing 270, an active agent reservoir 210, an adverse agent reservoir 260, a barrier 250, and a porous medium 265. The barrier 250 is present as a component that is adjacent to active agent reservoir 210 and the adverse agent reservoir 260. The porous medium 265 is adjacent to the adverse agent reservoir 260. The overlay backing 270 is adjacent to the porous medium 265 and provides an outer surface 290 of the dosage form 200. As shown, the release liner 240 has a release surface 245 adjacent to the active agent reservoir 210. In alternative embodiments, one or more components, such as a skin-contacting adhesive and/or a rate-limiting membrane may be interposed between the active agent reservoir 210 and the release surface 245. The active agent within the active agent reservoir 210 is in diffusional communication with the release surface. "Diffusional communication" is understood to mean that a substance, such as a active agent, is able to diffuse from one area to another by passing through or across one or more solid or liquid media.

The porous medium 265 is in "fluid communication" with the release surface 245. Fluid communication is meant to indicate that liquid may flow freely between two areas such as the skin-contacting surface 220 and the release surface 245. That is, liquid present on the exposed areas of the release surface 245 will also be able to contact the porous medium 265. The two-sided arrow 285 shows the area of fluid communication between the release surface 245 and the porous medium 265.

Figure 21:
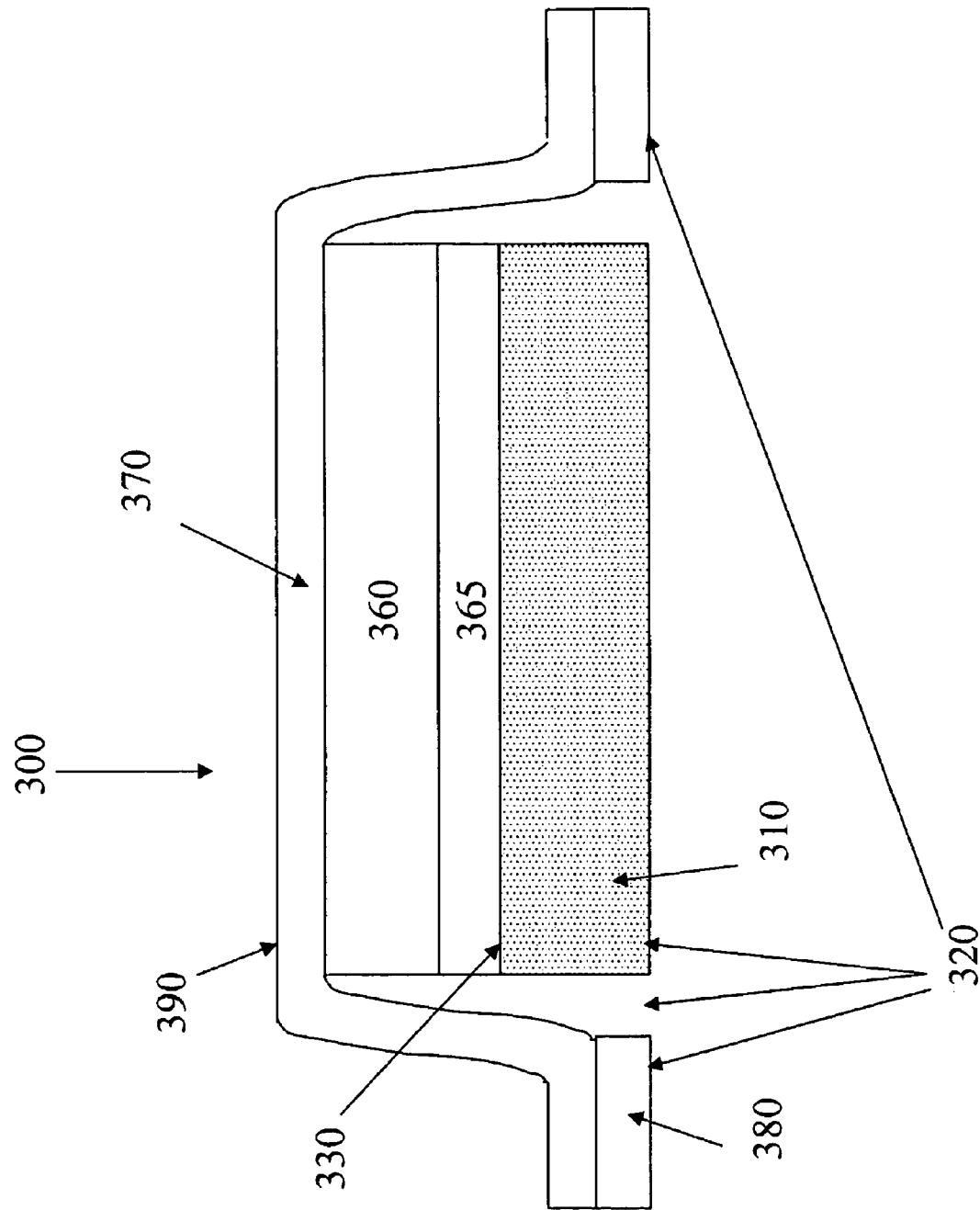
FIG. 21 shows a schematic cross-section of an embodiment of the present invention where the porous medium is adjacent to the active agent component.

In another embodiment, shown in FIG. 21, the present invention comprises a transdermal dosage form 300 comprising an active agent component 310 comprising a skin-contacting polymeric material and an active agent, an adverse agent reservoir 360 comprising an adverse agent to the active agent, and a porous medium 365. The active agent component defines a proximal, skin-contacting surface 320 and has a distal surface 330 opposed to the skin-contacting surface. The porous medium 365 is adjacent to the distal surface opposed to the skin-contacting surface 330 and the adverse agent reservoir 360. An overlay backing 370 with an overlay PSA 380 is adjacent to the adverse agent reservoir 360 and provides an outer surface 390 of the dosage form 300.

The porous medium 365 is in fluid communication with the skin-contacting surface 320. Fluid communication is meant to indicate that liquid may flow freely between the skin-contacting surface 320 and the porous medium 365. That is, if the dosage form is immersed in a liquid such that the skin-contacting surface is in contact with the liquid, then the liquid will also be able to contact the porous medium 365.

In this embodiment, adverse agent in the adverse agent reservoir 360 and active agent in the active agent component 310 should not be in diffusional communication with each other during normal storage and usage.

The active agent component may comprise a number of additional components in addition to a polymeric material and an active agent. Additional components of the active agent component can include skin penetration enhancers, drug solubilizers, plasticizers, anti-oxidants, colorants, and the like.

Examples of excipients useful as skin penetration enhancers or solubilizers in transdermal drug dosage forms include $C_8$-$C_{24}$ fatty acids such as isostearic acid, octanoic acid, and oleic acid; $C_8$-$C_{24}$ fatty alcohols such as oleyl alcohol and lauryl alcohol; lower alkyl esters of $C_8$-$C_{24}$ fatty acids such as ethyl oleate, isopropyl myristate, butyl stearate, and methyl laurate; monoglycerides of $C_8$-$C_{24}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); polyethylene glycol; propylene glycol; N,N-dimethyldodecylamine-N-oxide; terpenes, such as d-limonene, menthol, and terpineol.

In compositions of the active agent component of the present invention, the skin penetration enhancers, drug solubilizers, plasticizers, and other additives are dispersed, preferably substantially uniformly, and more preferably dissolved in the composition. Where the additive is a penetration enhancer, it is present in an amount that enhances drug permeation through the skin compared to a like composition not containing the penetration enhancer(s) when this phenomenon is measured using a standard skin penetration model, such as in U.S. Pat. No. 5,585,111 (Peterson), the disclosure of which is herein incorporated by reference. In one embodiment, the total amount of penetration enhancer and solubilizer is less than about 40% by weight based on the total weight of the composition. In another embodiment, the total amount of penetration enhancer and solubilizer is less than about 30% based on the total weight of the composition.

Active agent component compositions of the invention can be prepared by combining the polymer matrix, active agent, and optional additives, such as penetration enhancers, with an organic solvent (e.g., ethyl acetate, isopropanol, methanol, acetone, 2-butanone, ethanol, toluene, alkanes, and mixtures thereof) to provide a coating composition. The mixture is shaken or stirred until a homogeneous coating composition is obtained. The resulting composition is then applied to a release liner using conventional coating methods (e.g., knife coating or extrusion die coating) to provide a predetermined uniform thickness of coating composition. Non-continuous or discontinuous coatings may be prepared using methods such as stripe coating, screen printing, and ink-jet printing.

Dosage forms of the present invention typically comprise a release liner that covers and protects the skin-contacting surface prior to use by a patient. Suitable release liners include conventional release liners comprising a known sheet material such as a polyester web, a polyethylene web, a polystyrene web, or a polyethylene-coated paper coated with a suitable fluoropolymer or silicone based coating. The release liner that has been coated with the composition is then dried to prepare the active agent component and laminated to the other components of the dosage form using conventional methods. An optional tie component, heat, and/or pressure may be used to connect the active agent component with the barrier component. In addition, the active agent component compositions may be directly coated onto the barrier component and subsequently dried and laminated to a release liner.

When the adverse agent or reservoir component comprises a pressure-sensitive adhesive or similar polymeric material or matrix, then the adverse agent or reservoir component compositions of the invention can be prepared using methods similar to those for preparing the active agent component, with the exception that an adverse agent is used in place of the active agent to prepare the coating composition. Alternatively, the adverse agent or reservoir component can comprise a porous medium, such as a porous or microporous film. The adverse agent can be dissolved in an impregnating solvent and the porous or microporous film is soaked in the solvent for a sufficient period of time to allow the adverse agent to penetrate the pores of the film. The solvent is then removed leaving the adverse agent dispersed throughout the film.

Depending on the particular construction of the dosage form, the dried active agent component, adverse agent reservoir, porous medium, overlay backing, and optional barrier are laminated together using conventional methods. Optional tie components or heat may be used to connect one or more of the components. Alternatively, the active agent component compositions and adverse agent reservoir compositions may be directly coated onto one of the other components of the dosage form, dried, and subsequently laminated to another component or release liner.

An overlay backing is laminated to the surface of either the porous medium or the adverse agent reservoir to provide an upper surface of the dosage form, optionally using heat, pressure, and/or an additional tie component to ensure adequate contact.

One skilled in the art will appreciate that it may be preferred to vary the order of lamination steps depending on the types and thickness of the components comprising the dosage form.

In one embodiment, the dosage form will have a surface area greater than 5 cm$^2$. In another embodiment, the dosage form will have a surface area of greater than 10 cm$^2$. In another embodiment, the dosage form will have a surface area of less than 100 cm$^2$. In another embodiment, the dosage form will have a surface area of less than 40 cm$^2$.

Dosage forms of the present invention are typically packaged individually in a foil-lined pouch for storage. Dosage forms of the present invention may alternatively be provided in a rolled or stacked form suitable for use with a dispensing apparatus.

Active Agent

Any kind of active agent can be used in the dosage forms of the present invention. Examples of useful active agents include, but are not limited to, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile-dysfunction-improvement agents, immunosuppressants, anti-protozoal agents, anti-thyroid agents, anxiolytic agents, sedatives, hypnotics, neuroleptics, β-blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, and non-essential fatty acids. The dosage form can comprise more than one active agent.

More specific examples of active agents include, but are not limited to, opioids, benzodiazepines, barbiturates, and stimulants, such as methylphenidate and amphetamines, dronabinol, glutethimide, methylphenidate, nabilone, anabolic steroids, methylprylon, etchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, and detropropoxyphene.

In certain embodiments, the active agent is an opioid agonist (or "opioid"). Useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphine, dihydrocodeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures thereof.

In certain embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol and mixtures thereof. In one embodiment, the opioid agonist is oxycodone, hydromorphone or hydrocodone.

In certain embodiments, the transdermal dosage form can comprise a pharmacologically active agent that is capable of inducing a desired biological or pharmacological effect, which may include, but is not limited to, (1) affecting a living process; (2) having a prophylactic effect on an animal and preventing an undesired effect, such as preventing an infection; (3) alleviating a condition caused by, or a symptom of, a disease, e.g., pain or inflammation; and/or (4) alleviating, reducing, or eliminating a disease, condition, or symptom from the animal. The effect of the active agent may be local, such as for providing an anaesthetic effect, or it may be systemic or a combination thereof. General categories of active agents can, in one embodiment, include, but are not limited to: ACE inhibitors; adenohypophoseal hormones; adrenergic neuron blocking agents; adrenocortical steroids; inhibitors of the biosynthesis of adrenocortical steroids; alpha-adrenergic agonists; alpha-adrenergic antagonists; selective alpha-two-adrenergic agonists; androgens; anti-addictive agents; antiandrogens; antiinfectives, such as antibiotics, antimicrobials, and antiviral agents; analgesics and analgesic combinations; anorexics; antihelminthics; antiarthritics; antiasthmatic agents; anticonvulsants; antidepressants; antidiabetic agents; antidiarrheals; antiemetic and prokinetic agents; antiepileptic agents; antiestrogens; antifungal agents; antihistamines; antiinflammatory agents; antimigraine preparations; antimuscarinic agents; antinauseants; antineoplastics; antiparasitic agents; antiparkinsonism drugs; antiplatelet agents; antiprogestins; antipruritics; antipsychotics; antipyretics; antispasmodics; anticholinergics; antithyroid agents; antitussives; azaspirodecanediones; sympathomimetics; xanthine derivatives; cardiovascular preparations, including potassium and calcium channel blockers, alpha blockers, beta blockers, and antiarrhythmics; antihypertensives; diuretics and antidiuretics; vasodilators, including general coronary, peripheral, and cerebral; central nervous system stimulants; vasoconstrictors; cough and cold preparations, including decongestants; hormones, such as estradiol and other steroids, including corticosteroids; hypnotics; immunosuppressives; muscle relaxants; parasympatholytics; psychostimulants; sedatives; tranquilizers; nicotine and acid addition salts thereof; benzodiazepines; barbituates; benzothiadiazides; beta-adrenergic agonists; beta-adrenergic antagonists; selective beta-one-adrenergic antagonists; selective beta-two-adrenergic antagonists; bile salts; agents affecting volume and composition of body fluids; butyrophenones; agents affecting calcification; catecholamines; cholinergic agonists; cholinesterase reactivators; dermatological agents; diphenylbutylpiperidines; ergot alkaloids; ganglionic blocking agents; hydantoins; agents for control of gastric acidity and treatment of peptic ulcers; hematopoietic agents; histamines; 5-hydroxytryptamine antagonists; drugs for the treatment of hyperlipiproteinemia; laxatives; methylxanthines; moncamine oxidase inhibitors; neuromuscular blocking agents; organic nitrates; pancreatic enzymes; phenothiazines; prostaglandins; retinoids; agents for spasticity and acute muscle spasms; succinimides; thioxanthines; thrombolytic agents; thyroid agents; inhibitors of tubular transport of organic compounds; drugs affecting uterine motility; vitamins; and the like; or a combination thereof.

The transdermal dosage form can comprise an active component that may include, but is not limited to, flurogestone acetate, hydroxyprogesterone, hydroxyprogesterone acetate, hydroxyprogesterone caproate, medroxy-progesterone acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betamethasone acetate, cortisone, hydrocortisone, hydrocortisone acetate, corticosterone, fluocinolone acetonide, prednisolone, prednisone, triamcinolone, aldosterone, androsterone, testosterone, methyl testosterone, or a combination thereof.

The transdermal dosage form can comprise an active component that may include, but is not limited to: a) a corticosteroid, e.g., cortisone, hydrocortisone, prednisolone, beclomethasone propionate, dexamethasone, betamethasone, flumethasone, triamcinolone, triamcinolone acetonide, fluocinolone, fluocinolone acetonide, fluocinolone acetate, clobetasol propionate, or the like, or a combination thereof; b) an analgesic anti-inflammatory agent, e.g., acetaminophen, mefenamic acid, flufenamic acid, indomethacin, diclofenac, diclofenac sodium, alclofenac, ibufenac, oxyphenbutazone, phenylbutazone, ibuprofen, flurbiprofen, ketoprofen, salicylic acid, methylsalicylate, acetylsalicylic acid, 1-menthol, camphor, slindac, tolmetin sodium, naproxen, fenbufen, or the like, or a combination thereof; c) a hypnotic sedative, e.g., phenobarbital, amobarbital, cyclobarbital, lorazepam, haloperidol, or the like, or a combination thereof; d) a tranquilizer, e.g., fulphenazine, thioridazine, diazepam, flurazepam, chlorpromazine, or the like, or a combination thereof; e) an antihypertensive, e.g., clonidine, clonidine hydrochloride, bopinidol, timolol, pindolol, propranolol, propranolol hydrochloride, bupranolol, indenolol, bucumolol, nifedipine, bunitrolol, or the like, or a combination thereof; f) a hypotensive diuretic, e.g., bendroflumethiazide, polythiazide, methylchlorthiazide, trichlormethiazide, cyclopenthiazide, benzyl hydrochlorothiazide, hydrochlorothiazide, bumetanide, or the like, or a combination thereof; g) an antibiotic, e.g., penicillin, tetracycline, oxytetracycline, metacycline, doxycycline, minocycline, fradiomycin sulfate, erythromycin, chloramphenicol, or the like, or a combination thereof; h) an anesthetic, e.g., lydocaine, benzocaine, ethylaminobenzoate, or the like, or a combination thereof; i) another analgesic, e.g., acetylsalicylic acid, choline magnesium trisalicylate, acetaminophen, ibuprofen, fenoprofen, diflusinal, naproxen and the like; j) an antipruritic agent, e.g., bisabolol, oil of chamomile, chamazulene, allantoin, D-panthenol, glycyrrhetenic acid, a corticosteroid, an antihistamines and the like; k) an antimicrobial agent, e.g., methyl hydroxybenzoate, propyl hydroxybenzoate, chlorocresol, benzalkonium chlorides, nitrofurazone, nystatin, sulfacetamide, clotriamazole, or the like, or a combination thereof; l) an antifungal agent, e.g., pentamycin, amphotericin B, pyrrol nitrin, clotrimazole, or the like, or a combination thereof; m) a vitamin, e.g., vitamin A, ergocalciferol, cholecalciferol, octotriamine, riboflavin butyric acid ester, or the like, or a combination thereof; n) an antiepileptic, e.g., nitrazepam, meprobamate, clonazepam, or the like, or a combination thereof; o) an antihistamine, e.g., diphenhydramine hydrochloride, chlorpheniramine, diphenylimidazole, or the like, or a combination thereof; p) an antitussive, e.g., dextromethorphan, terbutaline, ephedrine, ephedrine hydrochloride, or the like, or a combination thereof; q) a sex hormone, e.g., progesterone, estradiol, estriol, estrone, or the like, or a combination thereof; r) an antidepressant, e.g., doxepin; s) a vasodilator, e.g., nitroglycerin, isosorbide nitrate, nitroglycol, pentaerythritol tetranitrate, dipyridamole, or the like, or a combination thereof; t) another drug, e.g., 5-fluorouracil, dihydroergotamine, desmopressin, digoxin, methoclopramide, domperidone, scopolamine, scopolamine hydrochloride, or the like, or a combination thereof; or the like; or a combination thereof.

The term "benzodiazepines" refers to benzodiazepine and active agents that are derivatives of benzodiazepine and are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate and mixtures thereof.

Barbiturates refer to sedative-hypnotic active agents derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital and mixtures thereof.

Stimulants refer to active agents that stimulate the central nervous system. Stimulants include, but are not limited to, amphetamines, such as amphetamine, dextroamphetamine resin complex, dextroamphetamine, methamphetamine, methylphenidate, methoxy substituted amphetamines, such as 3,4-methylenedioxymethamphetamine (MDMA) and mixtures thereof.

The active agent can be a pharmaceutical agent intended for delivery to the colon, including, but not limited to, agents that act locally in the colonic region to treat a colon diseases such as irritable bowel syndrome, irritable bowel disease, Crohns disease, constipation, post operative atony, gastrointestinal infections, and therapeutic agents that deliver antigenic material to the lymphoid tissue. Active agents for the treatment of colon disease include, but are not limited to 5-ASA; steroids, such as hydrocortisone and budesonide; laxatives; stool softeners; octreotide; cisapride; anticholinergics; opioids; calcium channel blockers; DNA for delivery to the cells of the colon; glucosamine; thromboxane A2 synthetase inhibitors, such as Ridogrel; 5HT3-antagonists, such as ondansetron; antibodies against infectious bacteria, such as Clostridium difficile; and antiviral agents, for example, for the prophylaxis of HIV.

The active agent can also be a pharmaceutical agent that is systemically active and for which absorption is improved in the colon region. Such active agents include polar compounds such as: heparins; insulin; calcitonins; human growth hormone (HGH); growth hormone releasing hormone (GHRH); interferons; somatostatin and analogues such as octreotide and vapreotide; erythropoietin (EPO); granulocyte colony stimulating factor (GCSF); parathyroid hormone (PTH); luteinising hormone releasing hormone (LHRH) and analogues thereof; atrial natriuretic factor (ANF); vasopressin; desmopressin; calcitonin gene related peptide (CGRP); and analgesics.

Adverse Agent

The adverse agent can be any pharmaceutical active agent which at least partially reduces or blocks at least one biological effect of at least one active agent present in the dosage form or which creates an unpleasant effect when absorbed in sufficient amount into an animal's or patient's blood stream. Examples of adverse agents include, but are not limited to, antagonists of any therapeutically active agonist. Antagonists may prevent, diminish, or delay the pharmacological effects of an active agent. In addition, antagonists may be bitter tasting substances, emetics, and/or nauseants. When an opioid agonist is used as the active agent in the dosage form of the present invention, an opioid antagonist can be used as the adverse agent. Likewise, when a benzodiazepine is used as the active agent in the dosage form of the present invention, a benzodiazepine antagonist can be used as the adverse agent. When a barbiturate is used as an active agent in the dosage form of the present invention, a barbiturate antagonist can be used as the adverse agent. When an amphetamine is used as an active agent in the dosage form of the present invention, an amphetamine antagonist can be used as the adverse agent. When the active agent is toxic when dosed above its normal therapeutic range, i.e., when there is a significant potential for an overdose, then an antidote of the toxic active agent can be used as the adverse agent.

In one embodiment, the adverse agent is an opioid antagonist. Opioid antagonists useful in the present invention include, but are not limited to, naloxone, naltrexone, nalmefene, nalbuphine, nalorphine, cyclazacine, cyclazocine, levallorphan, pharmaceutically acceptable salts thereof, and mixtures thereof.

In certain embodiments, the opioid antagonist is nalmefene, naloxone, naltrexone, or a pharmaceutically acceptable salt thereof. In another embodiment, the opioid antagonist is a naltrexone salt, such as naltrexone hydrochloride.

Useful opioid antagonist salts include salts formed from an acid and the basic nitrogen group of an opioid antagonist. Examples of opioid antagonist salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Other opioid antagonist salts include salts prepared from an antagonist having an acidic functional group, such as a carboxylic acid or sulfonic acid functional group, and a pharmaceutically acceptable inorganic or organic base. Suitable bases include, but are not limited to those identified above in Section 5.1 in the paragraph which references the term "pharmaceutically acceptable salt".

Benzodiazepine antagonists that can be used as the adverse agent of the present invention include, but are not limited to, flumazenil.

Barbiturate antagonists which can be used as the adverse agent of the present invention include, but are not limited to, amphetamines, as described herein.

Stimulant antagonists that can be used as the adverse agent of the present invention include, but are not limited to, benzodiazepines, described herein.

In another embodiment of the present invention, the adverse agent is an agent that causes an undesired physiological reaction, such as emesis. This type of adverse agent can be used with any kind of therapeutic agent including an opioid, a benzodiazepine, a barbiturate, or a stimulant. Examples of emetic agents suitable for use as the adverse agent in the present invention includes any drug that safely and effectively induces vomiting after administration including, but not limited to, ipecac and apomorphine.

In one embodiment of the present invention, the dosage form is provided such that the ratio of adverse agent to active agent released, or alternatively absorbed into a blood stream, is from about 1:10 to about 10:1. In other embodiments, the ratio of adverse agent to active agent is about is 1:5, 1:4, 1:3, 1:2, or 1:1. In other embodiments, the dosage form is provided such that the ratio of adverse agent to active agent in the dosage form is from about 1:10 to about 10:1. In other embodiments, the ratio of adverse agent to active agent is about 1:5, 1:4, 1:3, 1:2, or 1:1. In another embodiment, the ratio of adverse agent to active agent released from the dosage form when the dosage form is tampered with, e.g., chewed, extracted, mechanically violated, is from 1:5, 1:4, 1:3, 1:2, or 1:1.

Methods for Treating or Preventing Pain

In accordance with the invention, the transdermal dosage form of the invention can be used to administer to a patient, e.g., a human, an analgesically effective amount of an opioid for the treatment or prevention of pain. The transdermal dosage form can be used to treat or prevent acute or chronic pain. For example, the transdermal dosage form can be used for, but is not limited to, treating or preventing cancer pain, central pain, labor pain, myocardial infarction pain, pancreatic pain, colic pain, post-operative pain, headache pain, muscle pain, bone pain, and pain associated with intensive care.

According to the methods of the invention, in one embodiment the transdermal dosage form is contacted with the skin of the patient and an opioid is released by the transdermal dosage form and becomes absorbed through the skin. Once absorbed into the patient, an opioid is provided in an analgesically effective amount. The transdermal dosage form can provide sustained and continuous delivery of an analgesically effective amount of an opioid. In another embodiment, on administration over the skin, the transdermal dosage form exhibits a steady state drug flux of about 1 to about 10 µg/cm$^2$/hr, as disclosed in U.S. Pat. Appl. Publication No. 2003/0026829 A1 (Venkatraman et al.), the disclosure of which is incorporated herein by reference.

In one embodiment of the present invention, the method of treating pain with any one of the dosage forms described herein, wherein said dosage form can provide a ratio of adverse agent to active agent released, or alternatively absorbed into a blood stream, from about 1:10 to about 10:1 when the dosage form is used in an inappropriate manner. For example, it may be attempted to extract the active agent from the dosage form with a solvent, such as a quid or gas. In certain embodiments, the dosage form, when tampered with in such a manner, will release both adverse and active agent. In certain embodiments, the ratio of adverse agent to active agent released when tampered with is about is 1:5, 1:4, 1:3, 1:2, or 1:1. In other embodiments, the method of treating pain comprises applying a dosage form as described herein, wherein said dosage form comprises a ratio of adverse agent to active agent from about 1:10 to about 10:1. In other embodiments, the ratio of adverse agent to active agent is about is 1:5, 1:4, 1:3, 1:2, or 1:1.

Kits

The present invention is also directed to a kit comprising at least one dosage form of the invention. In one embodiment, the dosage form is present in a container, e.g., a bottle or box. In another embodiment, the kit further comprises a set of instructions directing the use of the dosage form to treat a patient, e.g., for pain. In one embodiment, the instructions may be a printed label affixed to or printed on the container. In another embodiment, the instructions may comprise a printed sheet inserted into the container or into the packaging which contains the container. The instructions may also state that the dosage form and/or its usage are designed to reduce abuse, misuse or diversion of the dosage form.

EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Test Methods and Dosage Form Components

In Vitro Skin Permeation Test Method

The skin permeation data given in the examples below was obtained using the following test method. A 5.0 cm$^2$ transdermal patch was die-cut from the center of a 10.0 cm$^2$ overlay patch (5.0 cm$^2$ active area) for use as the test sample. The release liner was removed, and the patch was applied to human cadaver skin and pressed to cause uniform contact with the skin. The resulting patch/skin laminate was placed patch side up across the orifice of the lower portion of a vertical diffusion cell. The diffusion cell was assembled and the lower portion filled with 25 mL of warm (32° C.) receptor fluid (0.1 M phosphate buffer, pH 6.8) so that the receptor fluid contacted the skin. The sampling port was covered except when in use.

The cells were maintained at 32±2° C. throughout the course of the experiment. The receptor fluid was stirred by means of a magnetic stirrer throughout the experiment to assure a uniform sample and a reduced diffusion barrier on the dermal side of the skin. The entire volume of receptor fluid was withdrawn at specified time intervals and immediately replaced with fresh fluid. The withdrawn fluid was filtered through a 0.45 µm filter. The last 1-2 mL were then analyzed for the active agent, e.g., fentanyl, using conventional high performance liquid chromatography methods (Column: Zorbax SB AQ, 50×4.6 mm, 5 µm particle size; Mobile phase: 3-20% isopropanol in 22 mM phosphate buffer; Flow Rate: 1.5 mL/min; Detector: UV at 230 nm; Injection Volume: 10 µL; Run time: 6 minutes). The cumulative amount of fentanyl penetrating through the skin was calculated and reported as µg/cm2. Unless noted, the results are reported as the average of 8 replicates.

Solvent Extraction Method

The test samples were 3.5 cm$^2$ transdermal patches. The extraction solution was chosen from one of the following solutions: buffered saline (PBS, 0.1 M phosphate buffer for pH 6.5, 0.5 M sodium chloride); diethyl ether (reagent grade with BHT preservative); deionized (DI) water; ethanol (USP, absolute); ethyl acetate (HPLC grade).

A 15 mL extraction solution was added into a 40 mL vial. The skin-adhesive side of the patch was applied to the rim of the vial, such that the patch completely covered the opening of the vial. A screw-on, teflon septum cap was placed over the patch to seal the vial. The sealed vial was stored in an upright position for not more than one hour prior to shaking.

The vial was shaken on a shaker table (IKA Labortechnik 501 Digital Shaker) set to 250 rpm. At fixed time intervals of 5, 15, and 30 minutes 0.5 mL aliquots were removed through the septum using a syringe. Each aliquot was placed into a 1 mL vial. If the extraction solvent was ethyl acetate or ether, then it was evaporated to dryness. Methanol (0.5 mL, HPLC grade) was added to the sample, mixed, and assayed for active and adverse agents by reverse-phase HPLC. If the extraction solvent was water or ethanol, then the sample was assayed directly for active and adverse agents by reverse-phase HPLC.

Mechanical Separation Method

The test samples were 10.0 $cm^2$ overlay transdermal patches (active area 5.0 $cm^2$). Ten individuals tested a single patch of each type. The testers were given diagrams indicating the individual components of the patch. The testers were also provided with a scalpel, tweezers, and adhesive tape to use as tools. Each tester was given a one-hour time period and instructed to mechanically separate the patch in an attempt to separate the active agent, e.g., fentanyl, from the adverse agent, e.g., naltrexone. Separated material believed to contain fentanyl and to be free of naltrexone was placed into a 40 mL vial, extracted with approximately 5 mL of methanol, and tested by HPLC for both fentanyl and naltrexone content. The results are reported as the average amount of fentanyl recovered from each patch, the average amount of naltrexone recovered from each patch, and the ratio of fentanyl to naltrexone recovered.

Copolymer A. Preparation of Isooctyl Acrylate/2-Hydroxyethyl acrylate/Elvacite™ 1010 Copolymer Solution A master batch was prepared by combining isooctyl acrylate (714.00 g), 2-hydroxyethyl acrylate (523.00 g), polymethylmethacrylate macromonomer (52.00 g) of ELVACITE™ 1010 available from ICI Acrylics), 2,2'-azobis(2-methylbutyronitrile) (2.60 g), ethyl acetate (1245.50 g) and isopropanol (45.50 g). The resulting solution was divided in equal portions and placed into six 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath, unsealed, diluted with 76 g methanol per bottle, mixed until homogenous, and recombined into a 1 gallon (3.8 L) glass jar. The percent solids of the resultant copolymer was 40.5%. The inherent viscosity (of a 0.15 g/dL solution of polymer in ethyl acetate measured at 27° C.) was 0.77 dL/g.

Copolymer B. Preparation of 2-Ethylhexyl Acrylate/Dimethylaminoethyl Acrylate Methyl Chloride Quaternary/Methoxy Polyethylene Glycol 400 Acrylate Copolymer Solution A master batch was prepared by combining 2-ethylhexyl acrylate (234 g), dimethylaminoethyl acrylate methyl chloride quaternary (90 g), methoxy polyethylene glycol 400 acrylate (54 g), methanol (200.84 g) and acetone (221.14 g). The resulting solution was divided in equal portions and placed into two 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath and cooled. Methanol (50 g) and acetone (50 g) were added to each bottle and mixed until homogeneous. The resulting solutions were then treated with radical initiators for an additional 6 hours at 57° C. to reduce the amount of remaining residual monomers. The resulting copolymer solutions in the two bottles were recombined into a 1 gallon (3.8 L) glass jar. The percent solids of the resultant copolymer was 36.3%. The Brookfield viscosity was 835 centipoise.

Copolymer C. Preparation of Polyurea Copolymer Solution

Polyoxypropylenediamine (198.75 g, Jeffamine® D2000, Huntsman Co., Houston, Tex.), Polyoxyalkyleneamine (66.25 g, Jeffamine® XTJ 502, Huntsman Co., Houston, Tex.), 2-methyl-1,5-pentanediamine (0.44 g), and 2-propanol (301.14 g) were added to a 1 quart (0.95 L) jar and mixed until homogeneous. Dicyclohexylmethane-4,4'-diisocyanate (35.70 g) was then added to the jar with a 2-propanol wash and mixed for 16 hours to prepare a polymer solution.

The resulting solution was knife coated at a wet thickness of 22 mil (559 μm) onto an in-process silicone coated release liner and dried for 4 minutes at 110° F. (43° C.), for 4 minutes at 185° F. (85° C.), and for 4 minutes at 200° F. (93.3° C.). The dried copolymer (161.8 g) was then added to acetone (242.7 g) to prepare a 40.1% solids solution.

Preparation of Porous Polyethylene Film

A porous polyethylene film was produced according to the method described in U.S. Pat. No. 4,539,256 (Shipman), the disclosure of which is incorporated herein by reference in its entirety for all purposes. Briefly, molten high density polyethylene (Finathene® 7208, Atofina Petrochemicals, Houston, Tex.) was mixed with a USP-grade mineral oil (Chevron Superla® White Oil 31, Chevron Products Co., San Ramon, Calif.) and extruded onto a water-cooled wheel whereupon an oil-filled membrane was formed. The oil was then removed via washing with a solvent, followed by biaxial stretching to form a 5 mil (127 μm) thick porous film. The porous film was 74% porous and had a 250 nm bubble point pore size. The surface of the film that contacts the water-cooled wheel is referred to as the "wheel" side. The porous film was rendered hydrophilic via three sequential plasma etching treatments in a silane and oxygen plasma.

Example 1

A transdermal dosage form according to FIG. 7a, b was prepared as follows.

Fentanyl (19.5 g) was added to methanol (23.5 g) and mixed until all of the fentanyl was dissolved. To this solution, copolymer (251.6 g of the solution of isooctyl acrylate/2-hydroxyethyl acrylate/Elvacite™ 1010 from Copolymer A above) was added and mixed until a uniform coating formulation was obtained. The coating formulation was knife coated onto a silicone release liner. The coated liner was oven dried for 4 minutes at 110° F. (43° C.), for 4 minutes at 185° F. (85° C.), and for 4 minutes at 200° F. (93.3+ C.). The resulting dried coating weight was 12.6 mg/$cm^2$ (the unit mg/$cm^2$ is often used in the art when dealing with components and coatings which may be less than 4 mm in thickness. The resulting coating contained 16.0 percent fentanyl. The coated liner was laminated onto an in-process silicone release liner for temporary storage of the dried fentanyl-copolymer coating.

A naltrexone solution with a concentration of 0.2658 g/mL was prepared in tetrahydrofuran. The naltrexone solution was coated onto the wheel side of the porous polyethylene film described above and dried for 20 minutes at 125° F. (51.7° C.). The resulting film had a naltrexone concentration of 3.11 mg/$cm^2$.

A fluoropolymer coating of 30% (w/w) tetrafluoroethylene-hexafluoropropylene-vinylidene fluoride terpolymer (THV 220, Dyneon, Oakdale, Minn.) in acetone was then applied to the wheel side of the naltrexone impregnated film using a #5 Mayer rod. The resulting film had a nominal dried thickness of approximately 0.15 mil (4 μm).

The in-process silicone release liner from the fentanyl coating was removed and the dried coating was laminated to the fluoropolymer coating on the porous polyethylene film to form a multilaminate construction.

Tables 1 and 2. Solvent extraction was determined using the test method described above. The results are shown in Table 3. Mechanical separation testing was performed using the test method described above. The results are shown in Table 4.

TABLE 1

In Vitro Skin Permeation Test Results

| Example Number | Average Flux Fentanyl ($\mu g/cm^2/hr$) | | | | | | | | | | |
|---|---|---|---|---|---|---|---|---|---|---|---|
| | 4 hr | 8 hr | 12 hr | 24 hr | 36 hr | 48 hr | 72 hr | 96 hr | 120 hr | 144 hr | 168 hr |
| 1 | 0.0 | 0.4 | 0.9 | 1.2 | 1.3 | 1.1 | 1.1 | 1.0 | 1.0 | 0.9 | 0.9 |
| 2 | 0.0 | 0.2 | 0.5 | 0.9 | 1.1 | 1.0 | 1.0 | 0.9 | 1.0 | 0.9 | 0.9 |
| 3 | 0.7 | 2.4 | 3.5 | 3.8 | 4.3 | 4.3 | 4.4 | 4.4 | 3.6 | 3.5 | 3.2 |

TABLE 2

In Vitro Skin Permeation Test Results

| Example Number | Average Flux Naltrexone ($\mu g/cm^2/hr$) | | | | | | | | | | |
|---|---|---|---|---|---|---|---|---|---|---|---|
| | 4 hr | 8 hr | 12 hr | 24 hr | 36 hr | 48 hr | 72 hr | 96 hr | 120 hr | 144 hr | 168 hr |
| 1 | 0.52 | 0.00 | 0.01 | 0.00 | 0.09 | 0.01 | 0.05 | 0.14 | 0.01 | 0.02 | 0.03 |
| 2 | 0.21 | 0.00 | 0.00 | 0.00 | 0.00 | 0.00 | 0.01 | 0.05 | 0.00 | 0.00 | 0.00 |
| 3 | 0.09 | 0.00 | 0.00 | 0.00 | 0.02 | 0.01 | 0.01 | 0.00 | 0.01 | 0.01 | 0.01 |

TABLE 3

Solvent Extraction Test Results

| Ex. No. | Solvent | Ratio Fentanyl/Naltrexone | | | Naltrexone Extracted [mg] | | | Fentanyl Extracted [mg] | | |
|---|---|---|---|---|---|---|---|---|---|---|
| | | 5 min | 15 min | 30 min | 5 min | 15 min | 30 min | 5 min | 15 min | 30 min |
| 1 | DI Water | 53.8 | 70.9 | 57.6 | 0.0 | 0.0 | 0.0 | 0.1 | 0.2 | 0.3 |
| 1 | PBS | 37.0 | 32.0 | 14.1 | 0.1 | 0.2 | 0.3 | 0.2 | 0.3 | 0.4 |
| 1 | Ethanol | 171 | 50.8 | 22.7 | 0.0 | 0.1 | 0.3 | 3.6 | 4.8 | 5.2 |
| 1 | Ethyl Acetate | 1.1 | 0.8 | 0.7 | 4.4 | 6.5 | 7.6 | 4.7 | 4.9 | 5.1 |
| 1 | Diethyl Ether | 4.9 | 3.9 | 2.1 | 0.9 | 2.0 | 3.3 | 4.0 | 4.3 | 4.2 |
| 2 | DI Water | 1.0 | 1.0 | 0.9 | 0.1 | 0.2 | 0.4 | 0.1 | 0.2 | 0.3 |
| 2 | PBS | 0.8 | 0.9 | 1.0 | 0.2 | 0.4 | 0.4 | 0.2 | 0.3 | 0.4 |
| 2 | Ethanol | 3.4 | 2.2 | 1.4 | 1.1 | 2.2 | 3.8 | 3.8 | 4.8 | 5.1 |
| 2 | Ethyl Acetate | 3.7 | 2.4 | 1.9 | 1.7 | 2.7 | 3.4 | 5.2 | 5.7 | 5.8 |
| 2 | Diethyl Ether | 4.5 | 2.3 | 1.5 | 1.0 | 2.1 | 3.2 | 3.9 | 4.4 | 4.6 |
| 3 | DI Water | 1.2 | 1.8 | 1.2 | 0.2 | 0.4 | 0.6 | 0.1 | 0.3 | 0.4 |
| 3 | PBS | 2.0 | 1.5 | 1.2 | 0.1 | 0.2 | 0.4 | 0.2 | 0.3 | 0.4 |
| 3 | Ethanol | 3.5 | 2.1 | 1.2 | 1.2 | 2.5 | 4.4 | 4.0 | 5.2 | 5.2 |
| 3 | Ethyl Acetate | 1.7 | 1.2 | 1.0 | 3.6 | 5.2 | 4.6 | 5.3 | 5.4 | 4.4 |
| 3 | Diethyl Ether | 2.5 | 1.2 | 0.8 | 2.2 | 3.9 | 5.8 | 3.9 | 4.5 | 4.8 |

The resulting multilaminate construction was converted into 3.5 cm² and 5.0 cm² patches. Nine approximately evenly spaced holes, each with an area of 0.013 cm², were punched through the full thickness of each 3.5 cm² patch. A Tegaderm™ dressing was adhered to the side of the porous polyethylene film opposed to the fluoropolymer coating of each 3.5 cm² patch and trimmed to an area of 3.5 cm². Fifteen approximately evenly spaced holes, each with an area of 0.013 cm², were punched through the full thickness of each 5.0 cm² patch. A Tegaderm™ dressing was adhered to the side of the porous polyethylene film opposed to the fluoropolymer coating of each 5.0 cm² patch as an overlay backing and overlay PSA as shown in FIG. 14. The Tegaderm™ dressing was trimmed so that it extended 5 mm around the edges of the 5.0 cm² patch.

Permeation of both fentanyl and naltrexone through human cadaver skin was determined using the in vitro skin permeation test method described above. The results are shown in

TABLE 4

Mechanical Separation Test Results

| Example Number | Fentanyl [mg/patch] | Naltrexone [mg/patch] | Ratio Fentanyl/Naltrexone |
|---|---|---|---|
| 1 | 1.2 | 0.7 | 1.7 |
| 2 | 1.3 | 1.4 | 0.9 |
| 3 | 0.9 | 1.4 | 0.6 |

Example 2

A transdermal dosage form according to FIG. 6*a, b* was prepared as follows.

An antagonist reservoir component was prepared as follows. Naltrexone (13.55 g) was added to copolymer (149.4 g of the solution of 2-ethylhexyl acrylate/dimethylaminoethyl acrylate methyl chloride quaternary/methoxy polyethylene glycol 400 acrylate from copolymer B above) and mixed until homogeneous. The coating formulation was knife coated onto a silicone release liner. The coated liner was oven dried for 4 minutes at 110° F. (43° C.), for 4 minutes at 185° F. (85° C.), and for 4 minutes at 200° F. (93.3° C.). The resulting dried coating weight was 14.2 mg/cm².

A dried fentanyl-copolymer coating was prepared as described in Example 1. The in-process silicone release liner was removed from the dried fentanyl-copolymer coating, and the dried fentanyl-copolymer coating was laminated to the ethylene vinyl acetate side of a 2.0 mil (51 µm) thick laminate film of polyethylene terephthalate (PET) and ethylene vinyl acetate (Scotchpak™ 9732, 3M, St. Paul, Minn.).

The resulting multilaminate construction was converted into 3.5 cm² and 5.0 cm² parts. Nine approximately evenly spaced holes, each with an area of 0.013 cm², were punched through the full thickness of each 3.5 cm² part. Fifteen approximately evenly spaced holes, each with an area of 0.013 cm², were punched through the full thickness of each 5.0 cm² part.

The PET side of each multilaminate 3.5 or 5.0 cm² part was laminated to the exposed surface of the dried naltrexone coating to form a multilaminate construction. The resulting multilaminate construction was converted into 3.5 or 5 cm² patches, respectively.

The in-process silicone release liner was removed from the dried naltrexone coating and a Tegaderm™ dressing was adhered to the dried naltrexone coating of each 3.5 cm² patch and trimmed to an area of 3.5 cm². The in-process silicone release liner was removed from the dried naltrexone coating and a Tegaderm™ dressing was adhered to the dried naltrexone coating of each 5.0 cm² patch as an overlay backing and overlay PSA as shown in FIG. 14. The Tegaderm™ dressing was trimmed so that it extended 5 mm around the edges of the 5.0 cm² patch.

Permeation of both fentanyl and naltrexone through human cadaver skin was determined using the in vitro skin permeation test method described above. The results are shown in Tables 1 and 2. Solvent extraction was determined using the test method described above. The results are shown in Table 3. Mechanical separation testing was performed using the test method described above. The results are shown in Table 4.

Example 3

A transdermal dosage form according to FIG. 6a, b was prepared as follows.

A dried naltrexone coating was prepared as follows. Naltrexone (14.00 g), acetone (35.1 g), tetrahydrofuran (13.1 g), and copolymer (140 g of a 40.1% solids solution in acetone of polyurea copolymer C above) were added together and mixed until homogeneous. The resulting composition was coated onto an in-process silicone coated release liner and dried for 4 minutes at 110° F. (43° C.), for 4 minutes at 185° F. (85° C.), and for 4 minutes at 200° F. (93.3° C.). The resulting dried coating contained 20.0 percent naltrexone. The resulting dried coating weight was approximately 15.7 mg/cm².

A dried fentanyl-copolymer coating was prepared as described in Example 1. The dried fentanyl-copolymer coating was laminated to the polyethylene terephthalate side of a 2.0 mil (51 µm) thick laminate film of polyethylene terephthalate and ethylene vinyl acetate (Scotchpak™ 9732, 3M, St. Paul, Minn.).

The resulting multilaminate construction was converted into 3.5 cm² and 5.0 cm² parts. Nine evenly spaced holes, each with an area of 0.013 cm², were punched through the full thickness of each 3.5 cm² part. Fifteen evenly spaced holes, each with an area of 0.013 cm², were punched through the full thickness of each 5.0 cm² part.

The ethylene vinyl acetate side of each multilaminate 3.5 or 5.0 cm² part was laminated to the exposed surface of the dried naltrexone coating to form a multilaminate construction. The resulting multilaminate construction was converted into 3.5 or 5 cm² patches, respectively.

The in-process silicone release liner was removed from the dried naltrexone coating and a Tegaderm™ dressing was adhered to the dried naltrexone coating of each 3.5 cm² patch and trimmed to an area of 3.5 cm². The in-process silicone release liner was removed from the dried naltrexone coating and a Tegaderm™ dressing was adhered to the dried naltrexone coating of each 5.0 cm² patch as an overlay backing and overlay PSA as shown in FIG. 14. The Tegaderm™ dressing was trimmed so that it extended 5 mm around the edges of the 5.0 cm² patch.

Permeation of both fentanyl and naltrexone through human cadaver skin was determined using the in vitro skin permeation test method described above. The results are shown in Tables 1 and 2. Solvent extraction was determined using the test method described above. The results are shown in Table 3. Mechanical separation testing was performed using the test method described above. The results are shown in Table 4.

Example 4

A transdermal dosage form according to FIG. 1a, b was prepared as follows.

Fentanyl (10.3 g) was added to methanol (12.4 g) and mixed until all of the fentanyl was dissolved. To this solution, copolymer (86.1 g of the solution of isooctyl acrylate/2-hydroxyethyl acrylate/Elvacite™ 1010 (57/39/4) from Copolymer A above) was added and mixed until a uniform coating formulation was obtained. The coating formulation was knife coated using a slotted knife onto a silicone release liner using coating dams to create stripes of adhesive. The coated stripes were approximately 5 mm wide and separated with uncoated areas that were approximately 1.5 mm wide. The coated liner was oven dried for 4 minutes at 110° F. (43° C.), for 4 minutes at 185° F. (85° C.), and for 4 minutes at 200° F. (93.3° C.). The resulting dried coating weight was approximately 10.5 mg/cm2 in the coated areas. The resulting coating contained 17.1 percent fentanyl. The coated liner was laminated onto an in-process silicone release liner for temporary storage of the dried fentanyl-copolymer coating.

A polyvinylalcohol (PVA) film was prepared from the following stock solutions. Stock solution A was prepared by adding 50.0 g of polyvinyl alcohol (87-89% hydrolyzed, 124, 000-186,000 molecular weight) into a beaker containing 450.0 g of deionized water. The mixture was warmed on a hot plate and stirred constantly until the solution was homogeneous (approximately 30 minutes). Stock solution B was prepared by adding 4.0 g of polyacrylic acid (molecular weight 1,250,000) to 196.3 g of deionized water and stirring until homogenous. Stock solution C was prepared by adding 22.9 g of glyceryl monolaurate to 37.7 g of isopropyl alcohol and 16.0 g of deionized water. The mixture was heated in an oven at 140° F. (60° C.) for 30 minutes to dissolve the glyceryl monolaurate. Stock solution A (305.0 g) was mixed with stock solution B (99.8 g) until homogeneous. To this solution, stock solution C (58.3 g) was added and mixed until homogeneous. The resulting solution had a percent solids of 11% and a composition of 61:4:35 polyvinyl alcohol:polyacrylic acid:glyceryl monolaurate.

This solution was knife coated at a wet thickness of 10 mil (254 μm) onto a silicone coated release liner. The coated liner was oven dried for 4 minutes at 185° F. (85° C.) and 6 minutes at 225° F. (107° C.) to form a PVA film. The resulting dried coating weight was approximately 2 mg/cm². The in-process silicone release liner from the dried fentanyl-copolymer coating was removed and the dried coating was laminated to the PVA film to form a PVA-fentanyl coating laminate.

A antagonist reservoir component was prepared as described in Example 2. The resulting dried coating contained 20.0 percent naltrexone. The resulting dried coating weight was approximately 14.2 mg/cm2.

The exposed surface of the dried naltrexone coating was laminated to the exposed PVA surface of the PVA-fentanyl coating laminate to form a multilaminate construction.

The resulting multilaminate construction was converted into 3.5 cm² and 5.0 cm² patches. The in-process silicone release liner was removed from the dried naltrexone coating and a Tegaderm™ dressing was adhered to the dried naltrexone coating of each 3.5 cm² patch and trimmed to an area of 3.5 cm². The in-process silicone release liner was removed from the dried naltrexone coating and a Tegaderm™ dressing was adhered to the dried naltrexone coating of each 5.0 cm² patch as an overlay backing and overlay PSA as shown in FIG. 14. The Tegaderm dressing was trimmed so that it extended 5 mm around the edges of the of the 5.0 cm² patch.

Solvent extraction was determined using the test method described above. The results are shown in Table 5. Mechanical separation testing was performed using the test method described above. The results are shown in Table 6.

TABLE 6

Mechanical Separation Test Results

| Example Number | Fentanyl [mg/patch] | Naltrexone [mg/patch] | Ratio Fentanyl/Naltrexone |
|---|---|---|---|
| 4 | 0.8 | 1.2 | 0.7 |
| 5 | 1.3 | 0.4 | 3.6 |
| 6 | 1.7 | 1.5 | 1.1 |
| 7 | 1.6 | 1.3 | 1.2 |
| 8 | NA | NA | NA |
| 9 | 1.2 | 0.5 | 2.5 |

Example 5

A transdermal dosage form according to FIG. 1a, b was prepared as follows.

Fentanyl (10.3 g) was added to methanol (12.4 g) and mixed until all of the fentanyl was dissolved. To this solution, methyl laurate (15.0 g) and copolymer (85.6 g of the solution of isooctyl acrylate/2-hydroxyethyl acrylate/Elvacite™ 1010 from Copolymer A above) were added and mixed until a uniform coating formulation was obtained. The coating formulation was knife coated using a slotted knife onto a silicone release liner using coating dams to create stripes of adhesive. The coated stripes were approximately 5 mm wide and separated with uncoated areas that were approximately 1.5 mm wide. The coated liner was oven dried for 4 minutes at 110° F. (43° C.), for 4 minutes at 185° F. (85° C.), and for 4 minutes at 200° F. (93.3° C.). The resulting dried coating weight was approximately 14.1 mg/cm2 in the coated areas. The resulting

TABLE 5

Solvent Extraction Test Results

| Ex. No. | Solvent | Ratio Fentanyl/Naltrexone | | | Naltrexone Extracted [mg] | | | Fentanyl Extracted [mg] | | |
|---|---|---|---|---|---|---|---|---|---|---|
| | | 5 min | 15 min | 30 min | 5 min | 15 min | 30 min | 5 min | 15 min | 30 min |
| 4 | DI Water | 42.3 | 16.3 | 7.7 | 0.0 | 0.1 | 0.2 | 0.1 | 0.2 | 0.3 |
| 4 | PBS | 2.2 | 1.4 | 1.0 | 0.1 | 0.2 | 0.4 | 0.2 | 0.3 | 0.4 |
| 4 | Ethanol | 1385 | 84.4 | 34.4 | 0.0 | 0.1 | 0.1 | 2.9 | 4.0 | 4.2 |
| 4 | Ethyl Acetate | 136 | 62.7 | 28.1 | 0.0 | 0.1 | 0.2 | 4.1 | 4.4 | 4.5 |
| 4 | Diethyl Ether | 377 | 131 | 55.8 | 0.0 | 0.0 | 0.1 | 3.3 | 3.8 | 3.9 |
| 5 | DI Water | 14.0 | 10.6 | 7.5 | 0.0 | 0.1 | 0.2 | 0.1 | 0.3 | 0.6 |
| 5 | PBS | 24.4 | 27.8 | 14.9 | 0.1 | 0.3 | 0.6 | 0.7 | 1.3 | 1.8 |
| 5 | Ethanol | 2254 | 227 | 101 | 0.0 | 0.0 | 0.1 | 5.0 | 7.3 | 7.6 |
| 5 | Ethyl Acetate | 68.7 | 22.7 | 10.4 | 0.1 | 0.3 | 0.8 | 5.5 | 5.7 | 5.9 |
| 5 | Diethyl Ether | 203 | 120 | 67.3 | 0.0 | 0.0 | 0.1 | 4.5 | 4.7 | 4.8 |
| 6 | DI Water | 4.5 | 1.3 | 0.6 | 0.0 | 0.1 | 0.5 | 0.1 | 0.2 | 0.3 |
| 6 | PBS | 2.2 | 1.6 | 0.9 | 0.1 | 0.2 | 0.4 | 0.2 | 0.3 | 0.4 |
| 6 | Ethanol | 152 | 35.6 | 9.1 | 0.0 | 0.2 | 0.7 | 3.1 | 4.4 | 4.7 |
| 6 | Ethyl Acetate | 68.5 | 11.4 | 3.6 | 0.1 | 0.4 | 1.2 | 4.1 | 4.4 | 4.5 |
| 6 | Diethyl Ether | 19.7 | 12.3 | 7.5 | 0.2 | 0.3 | 0.5 | 3.3 | 3.7 | 3.9 |
| 7 | DI Water | 4.0 | 0.7 | 0.5 | 0.0 | 0.4 | 0.8 | 0.1 | 0.3 | 0.4 |
| 7 | PBS | 4.6 | 2.5 | 1.5 | 0.2 | 0.5 | 1.1 | 0.6 | 1.1 | 1.5 |
| 7 | Ethanol | 320 | 67.4 | 13.3 | 0.0 | 0.1 | 0.6 | 4.4 | 5.8 | 6.1 |
| 7 | Ethyl Acetate | 71.5 | 22.2 | 4.5 | 0.1 | 0.2 | 1.2 | 5.1 | 5.1 | 5.3 |
| 7 | Diethyl Ether | 25.8 | 18.0 | 11.6 | 0.2 | 0.3 | 0.4 | 4.3 | 4.2 | 4.6 |
| 8 | DI Water | 1.7 | 1.5 | 1.2 | 0.1 | 0.2 | 0.3 | 0.1 | 0.2 | 0.2 |
| 8 | PBS | 3.6 | 1.7 | 1.1 | 0.2 | 0.4 | 1.1 | 0.1 | 0.3 | 0.4 |
| 8 | Ethanol | 9.9 | 3.5 | 1.5 | 0.4 | 1.9 | 3.9 | 2.4 | 4.1 | 4.3 |
| 8 | Ethyl Acetate | NA | NA | NA | NA | NA | NA | NA | NA | NA |
| 8 | Diethyl Ether | 3.4 | 1.5 | 0.9 | 1.6 | 4.1 | 6.5 | 3.6 | 4.1 | 4.5 |
| 9 | DI Water | 0.7 | 0.7 | 0.7 | 0.2 | 0.4 | 0.7 | 0.1 | 0.3 | 0.5 |
| 9 | PBS | 0.6 | 0.3 | 0.3 | 0.8 | 3.6 | 5.8 | 0.4 | 1.0 | 1.6 |
| 9 | Ethanol | 3.9 | 1.3 | 1.0 | 1.3 | 4.4 | 5.8 | 4.1 | 5.4 | 5.7 |
| 9 | Ethyl Acetate | 3.8 | 2.0 | 1.3 | 1.4 | 2.9 | 4.4 | 5.2 | 5.6 | 5.6 |
| 9 | Diethyl Ether | 1.5 | 1.0 | 0.8 | 2.5 | 4.8 | 6.3 | 3.3 | 4.3 | 4.7 | coating contained 17.1% fentanyl. The coated liner was laminated onto an in-process silicone release liner for temporary storage of the dried fentanyl-methyl laurate-copolymer coating.

A PVA film was prepared as described in example 4. The in-process silicone release liner from the dried fentanyl-copolymer coating was removed and the dried coating was laminated to the PVA film to form a PVA-fentanyl coating laminate.

A antagonist reservoir component was prepared as described in Example 2. The resulting dried coating contained 20.0 percent naltrexone. The resulting dried coating weight was approximately 14.2 mg/cm2.

The exposed surface of the dried naltrexone coating was laminated to the exposed PVA surface of the PVA-fentanyl coating laminate to form a multilaminate construction.

The resulting multilaminate construction was converted into 3.5 cm$^2$ and 5.0 cm$^2$ patches. The in-process silicone release liner was removed from the dried naltrexone coating and a Tegaderm™ dressing was adhered to the dried naltrexone coating of each 3.5 cm$^2$ patch and trimmed to an area of 3.5 cm$^2$. The in-process silicone release liner was removed from the dried naltrexone coating and a Tegaderm™ dressing was adhered to the dried naltrexone coating of each 5.0 cm$^2$ patch as an overlay backing and overlay PSA as shown in FIG. 14. The Tegaderm dressing was trimmed so that it extended 5 mm around the edges of the of the 5.0 cm$^2$ patch.

Solvent extraction was determined using the test method described above. The results are shown in Table 5. Mechanical separation testing was performed using the test method described above. The results are shown in Table 6.

Example 6

A transdermal dosage form according to FIG. 1*a, b* was prepared as follows.

A PVA-fentanyl coating laminate was prepared as described in Example 4. A dried naltrexone coating was prepared as described in Example 3. The exposed surface of the dried naltrexone coating was laminated to the exposed PVA surface of the PVA-fentanyl coating laminate to form a multilaminate construction.

The resulting multilaminate construction was converted into 3.5 cm$^2$ and 5.0 cm$^2$ patches. The in-process silicone release liner was removed from the dried naltrexone coating and a Tegaderm™ dressing was adhered to the dried naltrexone coating of each 3.5 cm$^2$ patch and trimmed to an area of 3.5 cm$^2$. The in-process silicone release liner was removed from the dried naltrexone coating and a Tegaderm™ dressing was adhered to the dried naltrexone coating of each 5.0 cm$^2$ patch as an overlay backing and overlay PSA as shown in FIG. 14. The Tegaderm dressing was trimmed so that it extended 5 mm around the edges of the of the 5.0 cm$^2$ patch.

Permeation through human cadaver skin was determined using the in vitro skin permeation test method described above. The results are shown in Table 1. Solvent extraction was determined using the test method described above. The results are shown in Table 2.

Example 7

A transdermal dosage form according to FIG. 1*a, b* was prepared as follows.

A PVA-fentanyl coating laminate was prepared as described in Example 5. A dried naltrexone coating was prepared as described in Example 3. The exposed surface of the dried naltrexone coating was laminated to the exposed PVA surface of the PVA-fentanyl coating laminate to form a multilaminate construction.

The resulting multilaminate construction was converted into 3.5 cm$^2$ and 5.0 cm$^2$ patches. The in-process silicone release liner was removed from the dried naltrexone coating and a Tegaderm™ dressing was adhered to the dried naltrexone coating of each 3.5 cm$^2$ patch and trimmed to an area of 3.5 cm$^2$. The in-process silicone release liner was removed from the dried naltrexone coating and a Tegaderm™ dressing was adhered to the dried naltrexone coating of each 5.0 cm$^2$ patch as an overlay backing and overlay PSA as shown in FIG. 14. The Tegaderm dressing was trimmed so that it extended 5 mm around the edges of the of the 5.0 cm$^2$ patch.

Solvent extraction was determined using the test method described above. The results are shown in Table 5. Mechanical separation testing was performed using the test method described above. The results are shown in Table 6.

Example 8

A transdermal dosage form according to FIG. 1*a, b* was prepared as follows.

A naltrexone solution with a concentration of 30.0% (w/w) was prepared in tetrahydrofuran. The naltrexone solution was coated onto the wheel side of the porous polyethylene film described above and dried for 12 minutes at 125° F. (51.7° C.). The resulting film had a naltrexone concentration of 3.2 mg/cm$^2$.

A solution having 11% percent solids and a composition of 61:4:35 polyvinyl alcohol:polyacrylic acid:glyceryl monolaurate was prepared as described in Example 4. This solution was coated with a #12 Mayer rod onto the naltrexone-loaded porous polyethylene film described above and oven dried for 10 minutes at 140° F. (60° C.) to prepare a PVA-porous polyethylene multi laminate.

A dried fentanyl-copolymer coating was prepared as described in Example 4. The in-process silicone release liner from the dried fentanyl-copolymer coating was removed and the dried coating was laminated to the PVA film to form a fentanyl-PVA-porous polyethylene multilaminate.

The resulting multilaminate construction was converted into 3.5 cm$^2$ and 5.0 cm$^2$ patches. A Tegaderm™ dressing was adhered to the porous polyethylene film of each 3.5 cm$^2$ patch and trimmed to an area of 3.5 cm$^2$. A Tegaderm™ dressing was adhered to the porous polyethylene film of each 5.0 cm$^2$ patch as an overlay backing and overlay PSA as shown in FIG. 14. The Tegaderm dressing was trimmed so that it extended 5 mm around the edges of the of the 5.0 cm$^2$ patch Solvent extraction was determined using the test method described above. The results are shown in Table 5.

Example 9

A transdermal dosage form according to FIG. 1*a, b* was prepared as follows.

A dried fentanyl-methyl laurate-copolymer coating was prepared as described in Example 5.

A naltrexone solution with a concentration of 29.9% (w/w) was prepared in tetrahydrofuran. The naltrexone solution was coated onto the wheel side of the porous polyethylene film described above and dried for 20 minutes at 125° F. (51.7° C.). The resulting film had a naltrexone concentration of 2.99 mg/cm$^2$.

A solution having 11% percent solids and a composition of 61:4:35 polyvinyl alcohol:polyacrylic acid:glyceryl monolaurate was prepared as described in Example 4. This solution was coated with a #12 Mayer rod onto the wheel side of the naltrexone-loaded porous polyethylene film described above and oven dried for 10 minutes at 140° F. (60° C.) to prepare a PVA-porous polyethylene multilaminate.

The in-process silicone release liner from the dried fentanyl-methyl laurate-copolymer coating was removed and the dried coating was laminated to the PVA film to form a fentanyl-PVA-porous polyethylene multilaminate.

The resulting multilaminate construction was converted into 3.5 cm² and 5.0 cm² patches. A Tegaderm™ dressing was adhered to the porous polyethylene film of each 3.5 cm² patch and trimmed to an area of 3.5 cm². A Tegaderm™ dressing was adhered to the porous polyethylene film of each 5.0 cm² patch as an overlay backing and overlay PSA as shown in FIG. 14. The Tegaderm dressing was trimmed so that it extended 5 mm around the edges of the of the 5.0 cm² patch. Solvent extraction was determined using the test method described above. The results are shown in Table 5. Mechanical separation testing was performed using the test method described above. The results are shown in Table 6.

Examples 10-17

In Vitro Skin Permeation Test Method

The skin permeation data given in the examples below was obtained using the following test method. The test samples were transdermal dosage forms having a total area of 5.0 cm² and an active drug-containing area of 2.0 cm² was used as the test sample. The release liner was removed, and the patch was applied to human cadaver skin and pressed to cause uniform contact with the skin. The resulting patch/skin laminate was placed patch side up across the orifice of the lower portion of a vertical diffusion cell. The diffusion cell was assembled and the lower portion filled with 25 mL of warm (32° C.) receptor fluid (0.1 M phosphate buffer, pH 6.8) so that the receptor fluid contacted the skin. The sampling port was covered except when in use.

The cells were maintained at 32±2° C. throughout the course of the experiment. The receptor fluid was stirred by means of a magnetic stirrer throughout the experiment to assure a uniform sample and a reduced diffusion barrier on the dermal side of the skin. The entire volume of receptor fluid was withdrawn at specified time intervals and immediately replaced with fresh fluid. The withdrawn fluid was filtered through a 0.45 µm filter. The last 1-2 mL were then analyzed for the active agent, e.g., fentanyl, using conventional high performance liquid chromatography methods (Column: Zorbax SB AQ, 50×4.6 mm, 5 µm particle size; Mobile phase: 3-20 wt-% isopropanol in 22 mM phosphate buffer; Flow Rate: 1.5 mL/min; Detector: UV at 230 nm; Injection Volume: 10 µL; Run time: 6 minutes). The cumulative amount of fentanyl penetrating through the skin was calculated and reported as µg/cm². Unless noted, the results are reported as the average of 8 replicates.

Solvent Extraction Method

The test samples were 3.3 cm² transdermal patches. The extraction solution was chosen from one of the following solutions: buffered saline (PBS, 0.1 M phosphate buffer for pH 6.5, 0.5 M sodium chloride); diethyl ether (reagent grade with BHT preservative); deionized (DI) water; ethanol (USP, absolute); ethyl acetate (HPLC grade).

The patch and a 15 mL extraction solution were added into a 40 mL vial. The sealed vial was vigorously shaken with a wrist-action shaker (Burrel, Model 75, speed setting: 10). At fixed time intervals of 5, 15, and 30 minutes aliquots were removed. Each aliquot was placed into an analysis vial. If the extraction solvent was ethyl acetate or ether, then it was evaporated to dryness and methanol (HPLC grade) added to the sample and mixed. Samples were assayed for active and adverse agents by reverse-phase HPLC. If the extraction solvent was water or ethanol, then the sample was assayed directly for active and adverse agents by reverse phase HPLC.

Mechanical Separation Method

The test samples were 20.0 cm² overlay transdermal patches (active area 10.5 cm²). Four individuals tested a single patch of each type. The testers were given diagrams indicating the individual components of the patch. The testers were also provided with a scalpel, tweezers, and adhesive tape to use as tools. Each tester was given a one-hour time period and instructed to mechanically separate the patch in an attempt to separate the active agent, e.g., fentanyl, from the naltrexone. Separated material believed to contain fentanyl and to be free of naltrexone was placed into 40 mL vials, extracted with approximately 5 mL of methanol, and tested by HPLC for both fentanyl and naltrexone content. The results are reported as the average amount of fentanyl recovered from each patch, the average amount of naltrexone recovered from each patch, and the ratio of fentanyl to naltrexone recovered.

Copolymer A. Preparation of Isooctyl Acrylate/2-Hydroxyethyl acrylate/Elvacite™ 1010 Copolymer Solution A master batch was prepared by combining isooctyl acrylate (714.00 g), 2-hydroxyethyl acrylate (523.00 g), polymethylmethacrylate macromonomer (52.00 g) of ELVACITE™ 1010 available from ICI Acrylics), 2,2'-azobis(2-methylbutyronitrile) (2.60 g), ethyl acetate (1245.50 g) and isopropanol (45.50 g). The resulting solution was divided in equal portions and placed into six 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath, unsealed, diluted with 76 g methanol per bottle, mixed until homogenous, and recombined into a 1 gallon (3.8 L) glass jar. The percent solids of the resultant copolymer was 40.5 wt-%. The inherent viscosity, I.V., (of a 0.15 g/dL solution of polymer in ethyl acetate measured at 27° C.) was 0.77 dL/g.

Copolymer B. Preparation of 2-Ethylhexyl Acrylate/Dimethylaminoethyl Acrylate Methyl Chloride Quaternary/Methoxy Polyethylene Glycol 400 Acrylate Copolymer Solution A master batch was prepared by combining 2-ethylhexyl acrylate (234 g), dimethylaminoethyl acrylate methyl chloride quaternary (90 g), methoxy polyethylene glycol 400 acrylate (54 g), methanol (200.84 g) and acetone (221.14 g). The resulting solution was divided in equal portions and placed into two 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath and cooled. Methanol (50 g) and acetone (50 g) were added to each bottle and mixed until homogeneous. The resulting solutions were then treated with radical scavengers for an additional 6 hours at 57° C. to reduce the amount of remaining residual monomers. The resulting copolymer solutions in the two bottles were recombined into a 1 gallon (3.8 L) glass jar. The percent solids of the resultant copolymer was 36.3 wt-%. The Brookfield viscosity was 835 centipoise.

Example 10

A transdermal dosage form according to FIG. 18 was prepared as follows.

Fentanyl (2.40 g) was added to methanol (2.80 g) and mixed until all of the fentanyl was dissolved. To this solution, copolymer (32.5 g of a 38.8 wt-% solids solution of isooctyl acrylate/2-hydroxyethyl acrylate/Elvacite™ 1010 with an inherent viscosity of 0.63 dL/g prepared according to the general procedure described for Copolymer A above) was added and mixed until a uniform coating formulation was obtained. The coating formulation was knife coated onto a silicone release liner. The coated liner was oven dried for 4 minutes at 110° F. (43° C.), for 4 minutes at 185° F. (85° C.), and for 2 minutes at 200° F. (93.3° C.). The resulting dried coating weight was 7.3 mg/cm$^2$ (the unit mg/cm$^2$ is often used in the art when dealing with components and coatings which may be less than 4 mm in thickness). The resulting coating contained 16.0 percent fentanyl. The coated liner was laminated onto the polyethylene terephthalate side of a 2.0 mil (51 µm) thick laminate film of polyethylene terephthalate and ethylene vinyl acetate (Scotchpak™ 9732, 3M, St. Paul, Minn.).

A adverse agent or reservoir component was prepared as follows. Naltrexone base (3.01 g) was added to copolymer (59.5 g of a solution of a 28.6 wt-% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was 14.4 mg/cm$^2$. The resulting coating contained 15.0 percent naltrexone. The coated liner was laminated to the ethylene vinyl acetate side of the dried fentanyl coating prepared above to form a multilaminate construction. The resulting multilaminate construction was converted into 2.0 cm$^2$ parts.

A 1.0 ounce/yd$^2$ (33.9 g/m$^2$) basis weight porous polyethylene apertured film (Style 6007, Polymer Group, Inc., North Charleston, S.C.) was ultrasonically welded to a 3.0 mil (76 µm) thick polyethylene film (CoTran™9720, 3M, St. Paul, Minn.) using a 20 kHz Dukane ultrasonic welder with a 3 inch (76.2 mm) diameter round horn and a 1:1 booster to create a porous film assembly. The anvil had 0.25 inch (6.4 mm) spacing, 0.044 inch (1118 µm) diameter pins, and a 0.01 inch (254 µm) pin height. Settings of 40 psi (0.28 Mpa), 1.5 second weld time and a 1.0 second hold time were used. The non-apertured side of the porous film assembly was laminated to a Tegaderm™ dressing and converted into 3.3 cm$^2$ parts. The release liner was then removed from the dried naltrexone coating of a 2.0 cm$^2$ part and laminated to the apertured film side of a 3.3 cm$^2$ part. Solvent extraction was determined using the test method described above. The results are shown in Table 7.

Example 11

A transdermal dosage form according to FIG. 18 was prepared as follows.

A dried fentanyl coating was prepared as described in Example 10.

An adverse agent or reservoir component containing an antagonist was prepared as follows. Naltrexone (13.55 g) was added to copolymer (149.4 g of a solution of a 28.6 wt-% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was 5.2 mg/cm$^2$. The dried naltrexone coating was divided into 3 equal pieces. A 5-component laminate of alternating dried naltrexone coatings and 3 mil (76 µm) thick polyvinyl alcohol (PVA) film (Monosol® M7030, Chris Craft Industrial Products, Inc., Gary, Ind.) was prepared by sequential lamination steps. The outer components of the 5-component laminate were dried naltrexone coatings. The silicone release liner was removed from one of the outer components of the 5-component laminate and the dried naltrexone coating was laminated to the ethylene vinyl acetate side of the dried fentanyl coating prepared above to form a multilaminate construction. The resulting multilaminate construction was converted into 2.0 cm$^2$ parts.

A 1.0 ounce/yd$^2$ (33.9 g/m$^2$) basis weight porous polyethylene apertured film (Style 6007, Polymer Group, Inc., North Charleston, S.C.) was ultrasonically welded to a 3.0 mil (76 µm) thick polyethylene film (CoTran™9720, 3M, St. Paul, Minn.) using a 20 kHz Dukane ultrasonic welder with a 3 inch (76.2 mm) diameter round horn and a 1:1 booster to create a porous film assembly. The anvil had 0.25 inch (6.4 mm) spacing, 0.044 inch (1118 µm) diameter pins, and a 0.01 inch (254 µm) pin height. Settings of 40 psi (0.28 Mpa), 1.5 second weld time and a 1.0 second hold time were used. The non-apertured side of the porous film assembly was laminated to a Tegaderm™ dressing and converted into 3.3 cm$^2$ parts. The release liner was then removed from the dried naltrexone coating of a 2.0 cm$^2$ part and laminated to the apertured film side of a 3.3 cm$^2$ part. Solvent extraction was determined using the test method described above. The results are shown in Table 7.

Example 12

A transdermal dosage form was prepared according to the same general description as Example 10 with the exception that the dried fentanyl coating had a coating weight of 8.0 mg/cm$^2$ and contained 9.6 percent fentanyl. Solvent extraction in buffered saline was determined using the test method described above. The results are shown in Table 7.

Example 13

A transdermal dosage form was prepared according to the same general description as Example 10 with the exception that the dried fentanyl coating had a coating weight of 18.6 mg/cm$^2$. Solvent extraction in buffered saline was determined using the test method described above. The results are shown in Table 7.

TABLE 7

| | | Solvent Extraction Test Results | | | | | | | | |
|---|---|---|---|---|---|---|---|---|---|---|
| | | Ratio Fentanyl/Naltrexone | | | Naltrexone Extracted [mg] | | | Fentanyl Extracted [mg] | | |
| Ex. No. | Solvent | 5 min | 15 min | 30 min | 5 min | 15 min | 30 min | 5 min | 15 min | 30 min |
| 1 | DI Water | 0.5 | 0.4 | 0.3 | 0.2 | 0.5 | 0.8 | 0.1 | 0.2 | 0.3 |
| 1 | PBS | 2.1 | 1.6 | 1.3 | 0.1 | 0.2 | 0.3 | 0.1 | 0.2 | 0.4 |
| 1 | Ethanol | 8.2 | 2.5 | 1.1 | 0.3 | 1.0 | 2.3 | 2.1 | 2.1 | 2.2 |
| 1 | Ethyl Acetate | 5.6 | 3.0 | 2.1 | 0.8 | 0.8 | 1.1 | 3.9 | 2.6 | 2.5 |

TABLE 7-continued

Solvent Extraction Test Results

| Ex. No. | Solvent | Ratio Fentanyl/Naltrexone | | | Naltrexone Extracted [mg] | | | Fentanyl Extracted [mg] | | |
|---|---|---|---|---|---|---|---|---|---|---|
| | | 5 min | 15 min | 30 min | 5 min | 15 min | 30 min | 5 min | 15 min | 30 min |
| 1 | Diethyl Ether | 3.9 | 2.5 | 1.9 | 0.5 | 0.8 | 1.0 | 2.4 | 2.3 | 2.3 |
| 2 | DI Water | 0.4 | 0.4 | 0.4 | 0.2 | 0.4 | 0.7 | 0.1 | 0.2 | 0.3 |
| 2 | PBS | 1.0 | 1.1 | 0.9 | 0.1 | 0.2 | 0.4 | 0.1 | 0.2 | 0.3 |
| 2 | Ethanol | 4.2 | 1.4 | 1.2 | 0.7 | 1.5 | 1.7 | 2.2 | 2.2 | 2.2 |
| 2 | Ethyl Acetate | 3.3 | 1.9 | 1.6 | 0.8 | 1.4 | 1.7 | 2.6 | 2.6 | 2.5 |
| 2 | Diethyl Ether | 3.2 | 1.8 | 1.4 | 0.8 | 1.7 | 1.8 | 2.4 | 3.1 | 2.5 |
| 3 | PBS | 0.8 | 0.7 | 0.6 | 0.1 | 0.3 | 0.4 | 0.1 | 0.2 | 0.2 |
| 4 | PBS | 1.1 | 1.2 | 1.1 | 0.1 | 0.2 | 0.3 | 0.2 | 0.3 | 0.4 |

Example 14

A transdermal dosage form according to FIG. 16 was prepared as follows. Dried fentanyl and naltrexone coatings were prepared according to the same general description as in Example 10 with the exception that the dried fentanyl coating had a coating weight of 14.4 mg/cm$^2$ and the dried naltrexone coating had a coating weight of 11.4 mg/cm$^2$. The multilaminate construction prepared by laminating the dried naltrexone coating to the ethylene vinyl acetate side of the dried fentanyl coating was converted into 10.5 cm$^2$ parts.

A 1.0 ounce/yd$^2$ (33.9 g/m$^2$) basis weight porous polyethylene apertured film (Style 6007, Polymer Group, Inc., North Charleston, S.C.) was converted into 10.5 cm$^2$ parts. A 3.0 mil (76 µm) thick polyethylene film (CoTran™9720, 3M, St. Paul, Minn.) was converted into 20.0 cm2 parts. Each 10.5 cm$^2$ apertured film part was ultrasonically welded to a 20.0 cm$^2$ polyethylene film part to form a porous film assembly using a 20 kHz Dukane ultrasonic welder with a 3 inch (76.2 mm) diameter round horn and a 1:1 booster. The anvil had 0.25 inch (6.4 mm) spacing, 0.044 inch (1118 µm) diameter pins, and a 0.01 inch (254 µm) pin height. Settings of 40 psi (0.28 Mpa), 25 second weld time and a 0.5 second hold time were used.

A dried adhesive coating was prepared by coating a copolymer solution (isooctyl acrylate/acrylic acid, 97:3, 31.8 wt-% solids, inherent viscosity of 1.11 dL/g) onto a silicone release liner and drying to obtain a dried coating weight of 3.5 mg/cm$^2$. The dried adhesive coating was converted into ring shaped parts with an outer diameter of 5.05 cm and an inside diameter of 3.66 cm. These ring shaped parts were then adhered to the polyethylene film portion of the porous film assembly prepared above such that the adhesive surrounded the apertured film portion of the porous film assembly.

The dried naltrexone coating of the 10.5 cm$^2$ fentanyl and naltrexone containing laminates prepared above were laminated to the apertured film portion of the porous film assembly to prepare a finished transdermal delivery patch. The resulting patches had a total area of 20.0 cm$^2$ and an active drug-containing area of 10.5 cm$^2$. Mechanical separation testing was performed as described in the method above. The results are shown in Table 8.

Example 15

A transdermal dosage form was prepared according to the same general description as Example 14 with the exception that the naltrexone reservoir component was a 5-component laminate of alternating dried naltrexone coatings and PVA components as described in Example 11. Mechanical separation testing was performed as described in the method above. The results are shown in Table 8.

TABLE 8

Mechanical Separation Test Results

| Example Number | Fentanyl [mg/dosage form] | Naltrexone [mg/dosage form] | Ratio Fentanyl/Naltrexone |
|---|---|---|---|
| 5 | 6.2 | 3.7 | 1.7 |
| 6 | 8.5 | 5.4 | 1.6 |

Example 16

A transdermal dosage form according to FIG. 16 was prepared as follows.

Fentanyl (3.44 g) was added to methanol (3.99 g) and mixed until all of the fentanyl was dissolved. To this solution, methyl laurate (5.01 g) and copolymer (29.8 g of a 38.8 wt-% solids solution of isooctyl acrylate/2-hydroxyethyl acrylate/Elvacite™ 1010 with an inherent viscosity of 0.63 dL/g prepared according to the general procedure described for Copolymer A above) was added and mixed until a uniform coating formulation was obtained. The coating formulation was knife coated onto a silicone release liner. The coated liner was oven dried for 4 minutes at 110° F. (43° C.), for 4 minutes at 185° F. (85° C.), and for 2 minutes at 200° F. (93.3° C.). The resulting dried coating weight was approximately 12.6 mg/cm$^2$. The resulting coating contained 17.2 percent fentanyl. The coated liner was laminated onto the polyethylene terephthalate side of a 2.0 mil (51 µm) thick laminate film of polyethylene terephthalate and ethylene vinyl acetate (Scotchpak™ 9732, 3M, St. Paul, Minn.).

A adverse agent or reservoir component was prepared as follows. Naltrexone (3.00 g) was added to copolymer (59.5 g of a 28.6 wt-% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was approximately 14.8 mg/cm$^2$. The coated liner was laminated to the ethylene vinyl acetate side of the dried fentanyl coating prepared above to form a multilaminate construction. The resulting multilaminate construction was converted into 2.0 cm$^2$ parts.

A porous film assembly with a ring shaped adhesive coating was prepared and adhered to the 2.0 cm² multilaminate parts following the general description in Example 14 with the exception that the final dimension of the finished transdermal patches had a total area of 5.0 cm and an active drug-containing area of 2.0 cm². Permeation of both fentanyl and naltrexone through human cadaver skin was determined using the test method described above. The results are shown in Tables 9 and 10.

Example 17

A transdermal dosage form was prepared according to the same general description as in Example 16 with the exception that the dried fentanyl coating was prepared as described in Example 14. Permeation of both fentanyl and naltrexone through human cadaver skin was determined using the test method described above. The results are shown in Table 9 and 10.

TABLE 9

In Vitro Skin Permeation Test Results

| Example Number | Average Flux Fentanyl (μg/cm2/hr) | | | | | | | | | | |
|---|---|---|---|---|---|---|---|---|---|---|---|
| | 4 hr | 8 hr | 12 hr | 24 hr | 36 hr | 48 hr | 72 hr | 96 hr | 120 hr | 144 hr | 168 hr |
| 7 | 0.0 | 0.9 | 3.6 | 4.6 | 4.8 | 5.3 | 4.7 | 4.7 | 4.2 | 3.8 | 3.6 |
| 8 | 0.5 | 0.4 | 0.5 | 1.7 | 1.9 | 2.2 | 2.1 | 2.2 | 2.2 | 2.1 | 1.9 |

TABLE 10

In Vitro Skin Permeation Test Results

| Example Number | Average Flux Naltrexone (μg/cm2/hr) | | | | | | | | | | |
|---|---|---|---|---|---|---|---|---|---|---|---|
| | 4 hr | 8 hr | 12 hr | 24 hr | 36 hr | 48 hr | 72 hr | 96 hr | 120 hr | 144 hr | 168 hr |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.60 | 0.00 | 0.28 | 0.00 | 0.12 |

Example 18

Fentanyl is a highly potent opiate analgesic that is being developed for a 7-day transdermal fentanyl product for the management of pain. To minimize its abuse potential, the incorporation of the opioid antagonist, naltrexone is under consideration. This pharmacokinetic study was conducted in support of a neuropharmacology study to determine the ratio of naltrexone required to blunt the pharmacological effects of fentanyl when fentanyl and naltrexone are co-administered at a fixed ratio by the intraperitoneal injection in male Sprague Dawley rats.

Male Sprague Dawley rats were divided into 3 groups (5 per group). Each rat received a single intraperitoneal injection of fentanyl (125 μg/kg) co-administered with naltrexone as described in Table 11A.

TABLE 11

Dosing Information

| Group | N | Treatment | Dosing |
|---|---|---|---|
| 1 | 5 | 1:1 fentanyl:naltrexone | 125 μg/kg fentanyl, 125 μg/kg naltrexone |
| 2 | 5 | 4:1 fentanyl:naltrexone | 125 μg/kg fentanyl, 31.3 μg/kg naltrexone |

TABLE 11-continued

Dosing Information

| Group | N | Treatment | Dosing |
|---|---|---|---|
| 3 | 5 | 10:1 fentanyl:naltrexone | 125 μg/kg fentanyl, 12.5 μg/kg naltrexone |

N = number of animals

Blood was collected from at predose, 10, 20, 30, 45, and 60 min, and at 1.5, 2, 4, and 6 h post fentanyl dose- The plasma obtained was stored at −20° C. until analyzed by LC-MS/MS for fentanyl. norfentanyl, naltrexone and 6-β-naltrexol concentrations. The standard curves for fentanyl and its metabolite, norfentanyl, ranged from 50 to 1000 pg/mL, whereas the standard curves for naltrexone and 6-β-naltrexol ranged from 10.1 to 505 pg/mL.

The mean pharmacokinetic metrics for fentanyl, norfentanyl and naltrexone are listed in Table 12. There was considerable variation in fentanyl and naltrexone plasma concentrations in all three groups. However, the ratio of fentanyl to naltrexone in the plasma was more consistent within the three groups across the sampling time points tested. Furthermore, the ratio of fentanyl to naltrexone plasma concentration increased with time owing to the longer plasma half-life of fentanyl. The target (dosed) ratios were reached at approximately 30 min to 1 h post dose The cage-side observations for the co-administered fentanyl and naltrexone demonstrated a lack of sedative effect of fentanyl at all 3 ratios of agonist to antagonist and at all time points studied. Although the relative concentration of fentanyl to naltrexone within the plasma of the rat increased with time, the absolute concentration of fentanyl in the plasma decreased so no clinical effects were observed.

TABLE 12

Mean Pharmacokinetic Metrics for Fentanyl, Naltrexone and Norfentanyl in Male Sprague Dawley Rats Following a Single Co-Administration of Fentanyl and Naltrexone Via Intraperitoneal Injection

| Group* | Analyte | $t_{max}$ (h) | $C_{max}$ (pg/mL) | $AUC_{inf}$ (pg·h/mL) | $t_{1/2}$ (h) |
|---|---|---|---|---|---|
| 1 | Fentanyl | 0.167 | 14916 | 3473 | 1.41 |
| | Naltrexone | 0.167 | 15099 | 9416 | 0.562 |
| | Norfentanyl | 0.350 | 2551 | 4939 | 1.69 |

TABLE 12-continued

Mean Pharmacokinetic Metrics for Fentanyl, Naltrexone and Norfentanyl in Male Sprague Dawley Rats Following a Single Co-Administration of Fentanyl and Naltrexone Via Intraperitoneal Injection

| Group* | Analyte | $t_{max}$ (h) | $C_{max}$ (pg/mL) | $AUC_{inf}$ (pg · h/mL) | $t_{1/2}$ (h) |
|---|---|---|---|---|---|
| 2 | Fentanyl | 0.167 | 22176 | 7923 | 1.40 |
|  | Naltrexone | 0.167 | 6155 | 3771 | 0.448 |
|  | Norfentanyl | 0.783 | 1907 | 5131 | 2.01 |
| 3 | Fentanyl | 0.167 | 16555 | 9519 | 1.69 |
|  | Naltrexone | 0.167 | 2116 | 1340 | 0.439 |
|  | Norfentanyl | 0.983 | 1809 | 4094 | 2.33 |

*Group 1 = 125 µg/kg fentanyl, 125 µg/kg naltrexone (1:1 fentanyl/naltexone ratio)
*Group 2 = 125 µg/kg fentanyl, 31.3 µg/kg naltrexone (4:1 fentanyl/naltrexone ratio)
*Group 3 = 125 µg/kg fentanyl, 12.5 µg/kg naltrexone (10:1 fentanyl/naltrexone ratio)

The rats were fasted overnight. Each rat within a group received a single intraperitoneal co-administration of fentanyl and naltrexone as listed in Table 13.

TABLE 13

Dosing Information

| Group | N | Treatment | Dosing |
|---|---|---|---|
| 1 | 5 | 1:1 fentanyl:naltrexone | 125 µg/kg fentanyl, 125 µg/kg naltrexone |
| 2 | 5 | 4:1 fentanyl:naltrexone | 125 µg/kg fentanyl, 31.3 µg/kg naltrexone |
| 3 | 5 | 10:1 fentanyl:naltrexone | 125 µg/kg fentanyl, 12.5 µg/kg naltrexone |

N = number of animals

Blood was collected into polypropylene tubes containing $K_2EDTA$ labeled with the following information: study number, dose group, animal number, and time of collection. Approximately 1 mL of blood was collected via the jugular vein cannula from each rat at predose, 10, 20, 30, 45 and 60 min, and at 1.5, 2, 4, and 6 h post dose. The withdrawn blood volume was replaced with heparinized blood from naïve rats. The blood samples were kept on ice until centrifuged at 4° C. (within 1 h of collection). The resulting plasma was separated and stored in appropriately labeled polypropylene containers at approximately −70° C. until analysis.

The plasma samples (0.200 mL) were analyzed for fentanyl, norfentanyl, naltrexone, and 6-β-naltrexol concentrations by the Bioanalytical Group of the Pharmacokinetics and Drug Metabolism (PKDM) department at Purdue Pharma L.P. After the addition of internal standards, the samples were subjected to solid phase extraction. The extract was dried and resuspended in 100 µL acetonitrile and analyzed by LC-MS/MS. The standard curves were linear over the range of 50 0 to 1000 pg/mL for fentanyl and norfentanyl. The naltrexone and 6-β-naltrexol standard curves were linear over the range of 10.1 to 505 pg/mL, with the limits of quantitation being defined as the ends of the standard curve. Samples that exceeded the standard curve were diluted with interference-free plasma and re-analyzed.

The non-compartmental pharmacokinetic metrics from the mean plasma concentration data were determined using Win-Nonlin, version 1.5 (Scientific Consulting, Inc.). The AUC value was estimated by the linear trapezoidal rule. Zero was used for any concentration that was less than the lower limit of quantitation (LLOQ) of the assay. The apparent $t_{1/2}$ was calculated as $t_{1/2}=0.693/\lambda$ where X is the elimination rate constant estimated from the regression of the terminal slope of the concentration versus time curve. At least 3 plasma concentrations after the peak concentration on the terminal phase were used to determine and the coefficient of determination ($R^2$) was required to be greater than or equal to 0.85.

Figure 22:
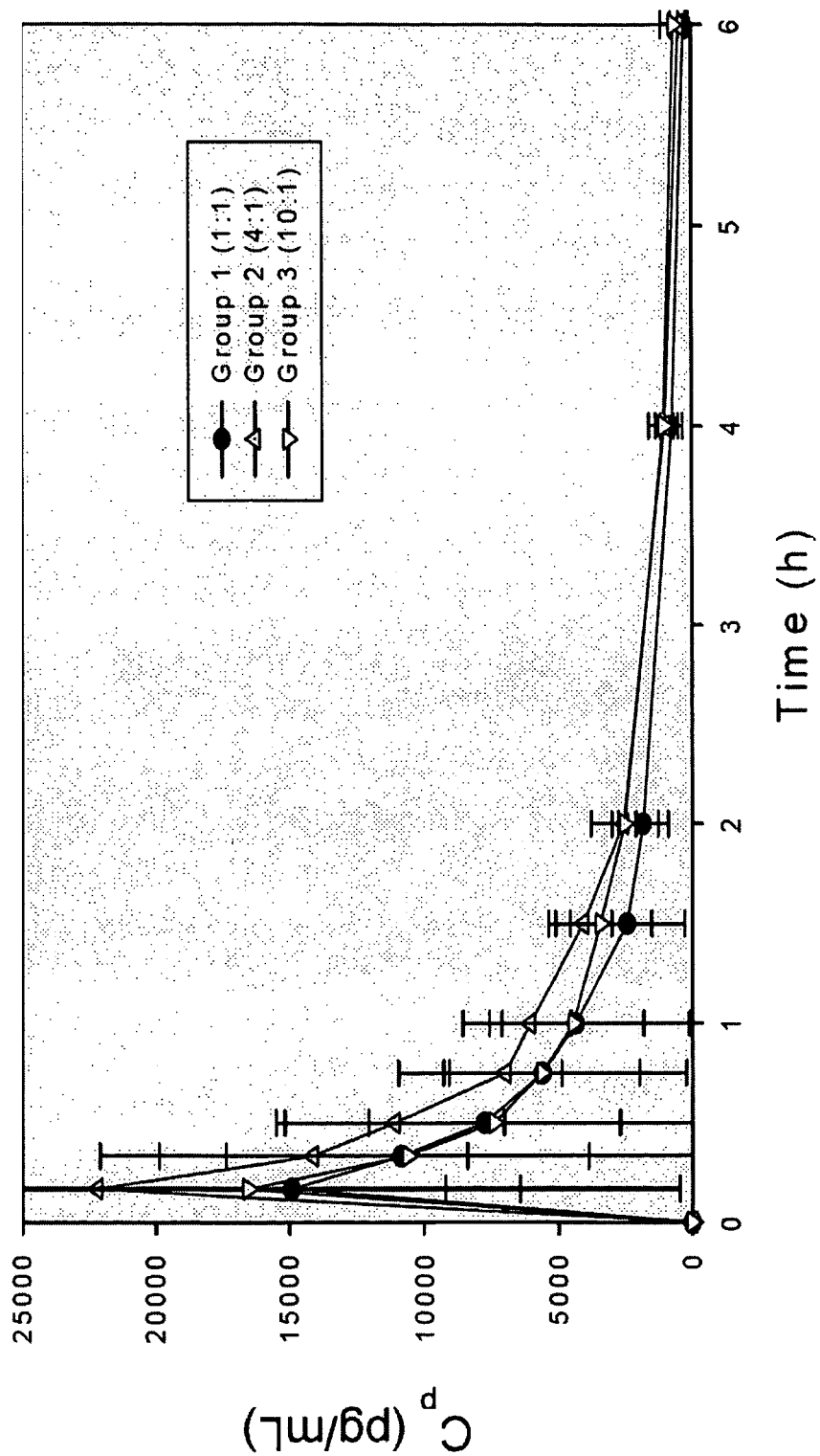
FIG. 22 shows mean (+/−) plasma concentrations of fentanyl in male sprague dawley rats following a single intraperitoneal administration of fentanyl at a dose of 125 µg/kg with varying ratios of naltrexone.
Figure 23:
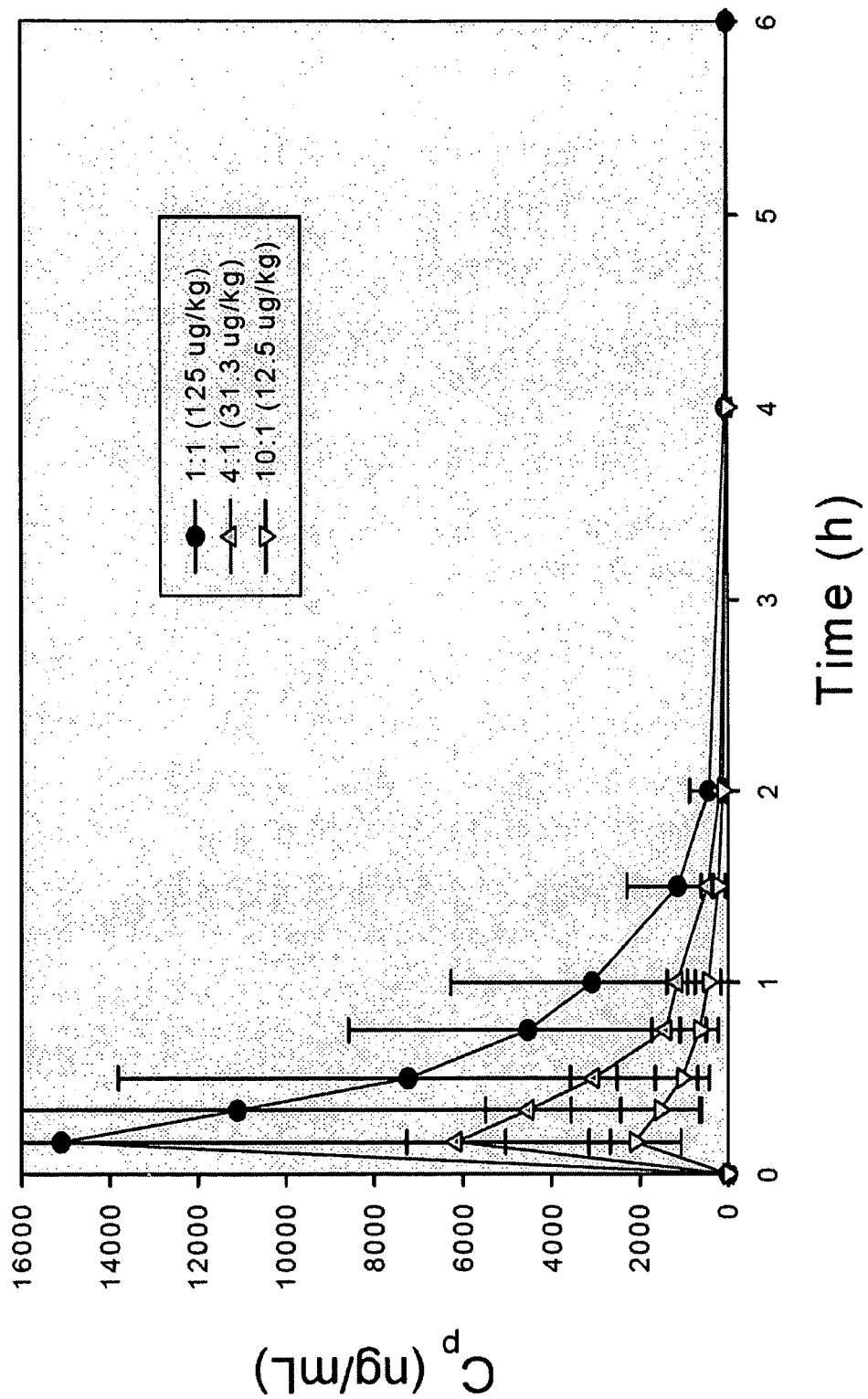
FIG. 23 shows mean (+/−) plasma concentrations of naltrexone in male sprague dawley rats following a single intraperitoneal co administration with fentanyl.
Figure 24:
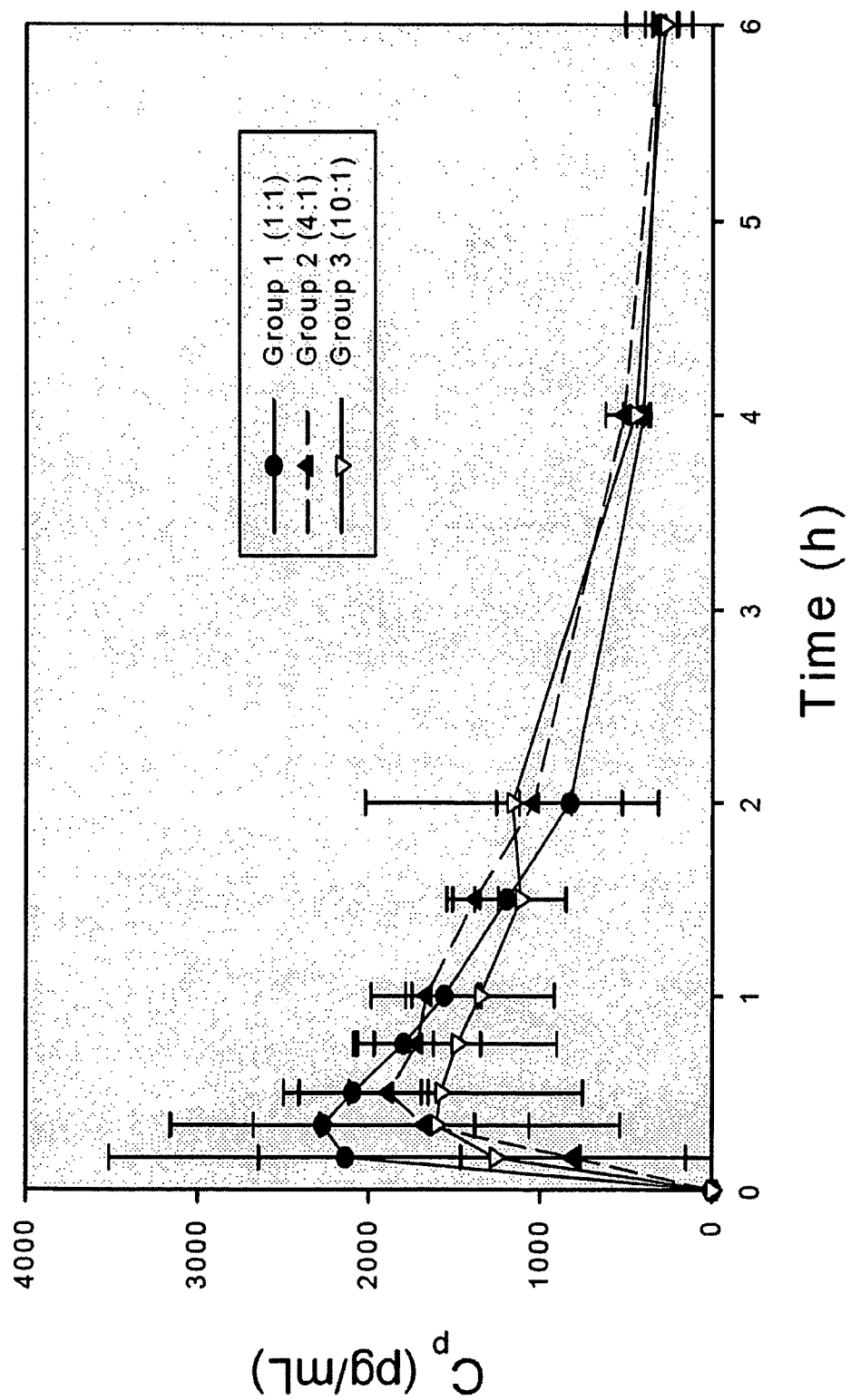
FIG. 24 shows mean (+/−) plasma concentrations of norfentanyl in male sprague dawley rats following the single intraperitoneal administration of fentanyl (125 µg/kg) with naltrexone.

The mean plasma concentration versus time profiles for fentanyl, naltrexone, and norfentanyl are plotted in FIGS. 22, 23, and 24, respectively, whereas the individual plots for fentanyl and naltrexone for each rat are provided in FIGS. 8D, 8E, and 8F for the three respective groups. The mean PK metrics for fentanyl, norfentanyl, and naltrexone are reported in Tables 14, 15, and 16, respectively. The individual PK metrics for fentanyl, norfentanyl and naltrexone are reported in Tables 17, 18, and 19 for Groups 1, 2, and 3, respectively.

Fentanyl mean plasma concentration versus time profiles are plotted in FIG. 22 whereas the individual plots for fentanyl and naltrexone for each rat are provided in FIGS. 8D, 8E, and 8F for the three respective groups. The mean pharmacolkinetic metrics for the three groups are listed in Table 11, whereas individual rat PK metrics are listed in Tables 14, 15, and 16 for Groups 1, 2, and 3, respectively. All three groups received the same dose of fentanyl. There was no difference in the mean pharmacokinetic profile or the mean pharmacolkinetic metrics for the three groups. However, the individual plasma concentration versus time profiles were highly variable. The $t_{max}$ value for all rats was 10 min, which was the first time point post injection. The $t_{1/2}$ values were similar for all three groups and ranged from 0.843 to 2.35 h (the terminal $t_{1/2}$ values were not calculable from one rat in each of Groups 1 and 3). The $C_{max}$ values ranged from 980 to 32309 pg/mL for Group 1, 10778 to 41969 pg/mL for Group 2, and 5950 to 2 78215 pg/mL for Group 3. The $AUC_{inf}$ values ranged from 7301 to 28382 pg·h/mL for Group 1, 16824 to 23552 pg·h/mL for Group 2, and 5387 to 27690 pg·h/mL for Group 3.

Figure 25:
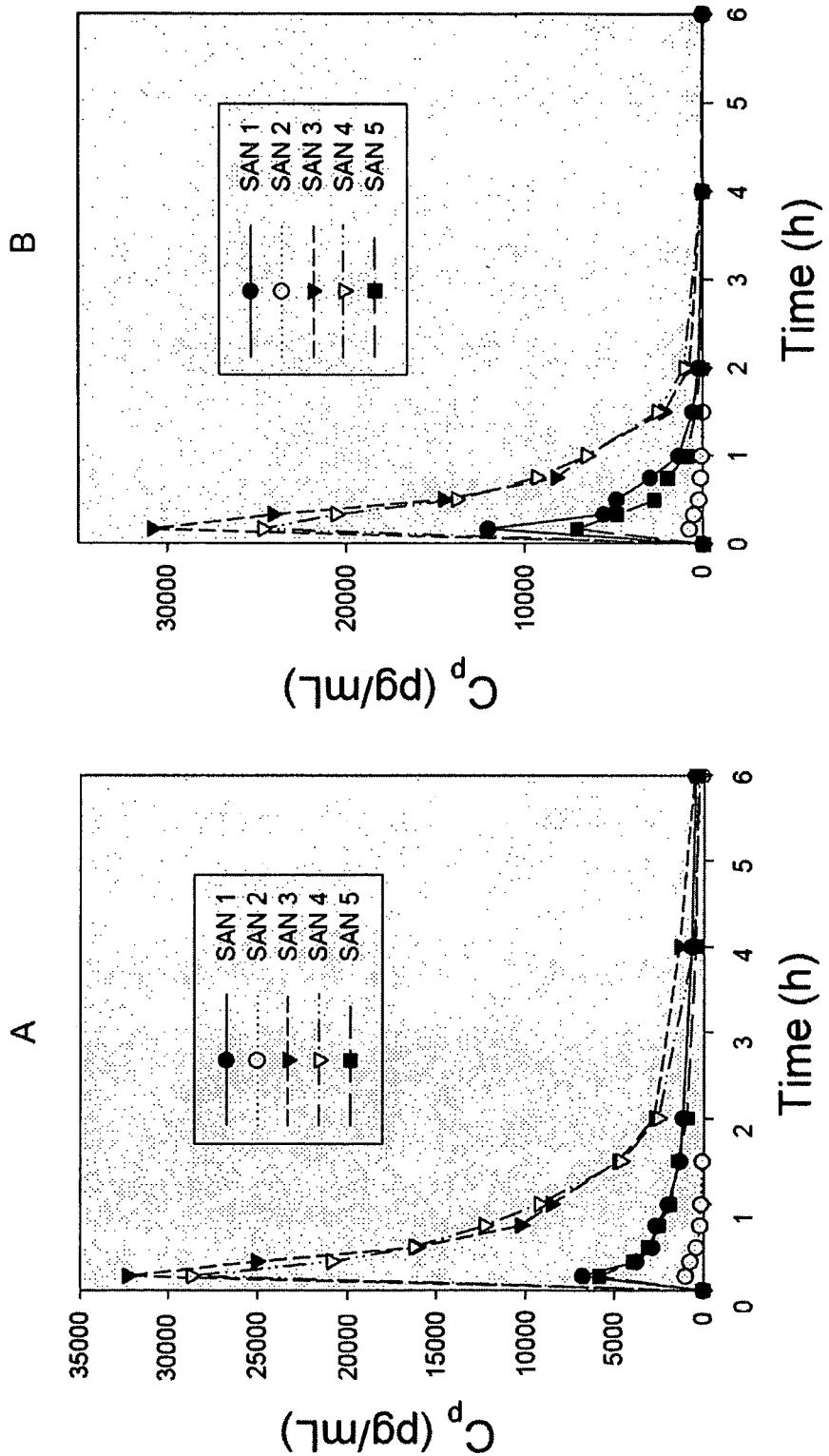
FIG. 25 shows group 1, fentanyl (A) and naltrexone (B) individual plasma concentrations in male sprague dawley rats following a single intraperitoneal co-administration of fentanyl and naltrexone (125 µg/kg each).
Figure 26:
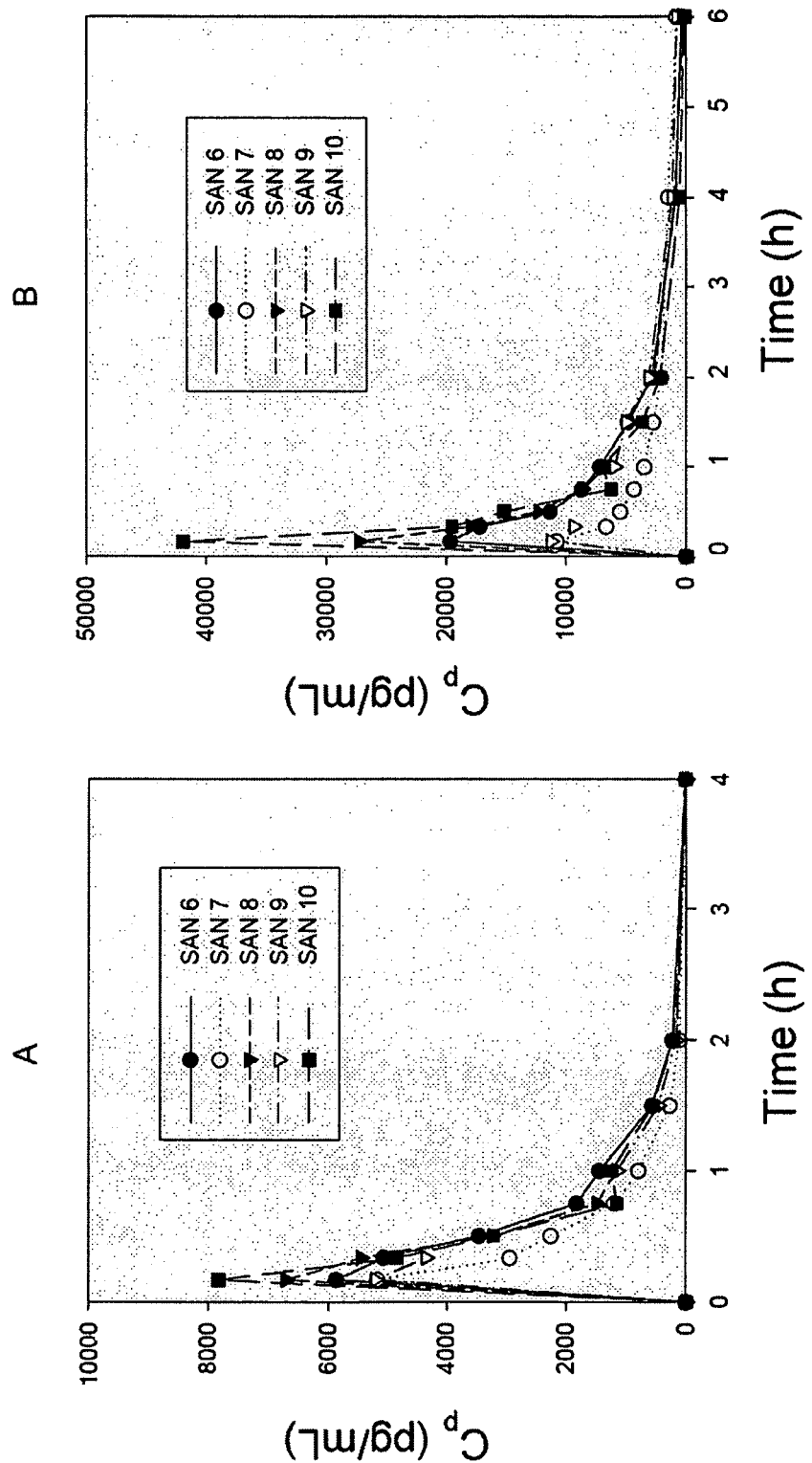
FIG. 26 shows group 2, fentanyl (A) and naltrexone (B) individual plasma concentrations in male sprague dawley rats following a single intraperitoneal co-administration of fentanyl (125 µg/kg) and naltrexone (31.25 µg/kg).
Figure 27:
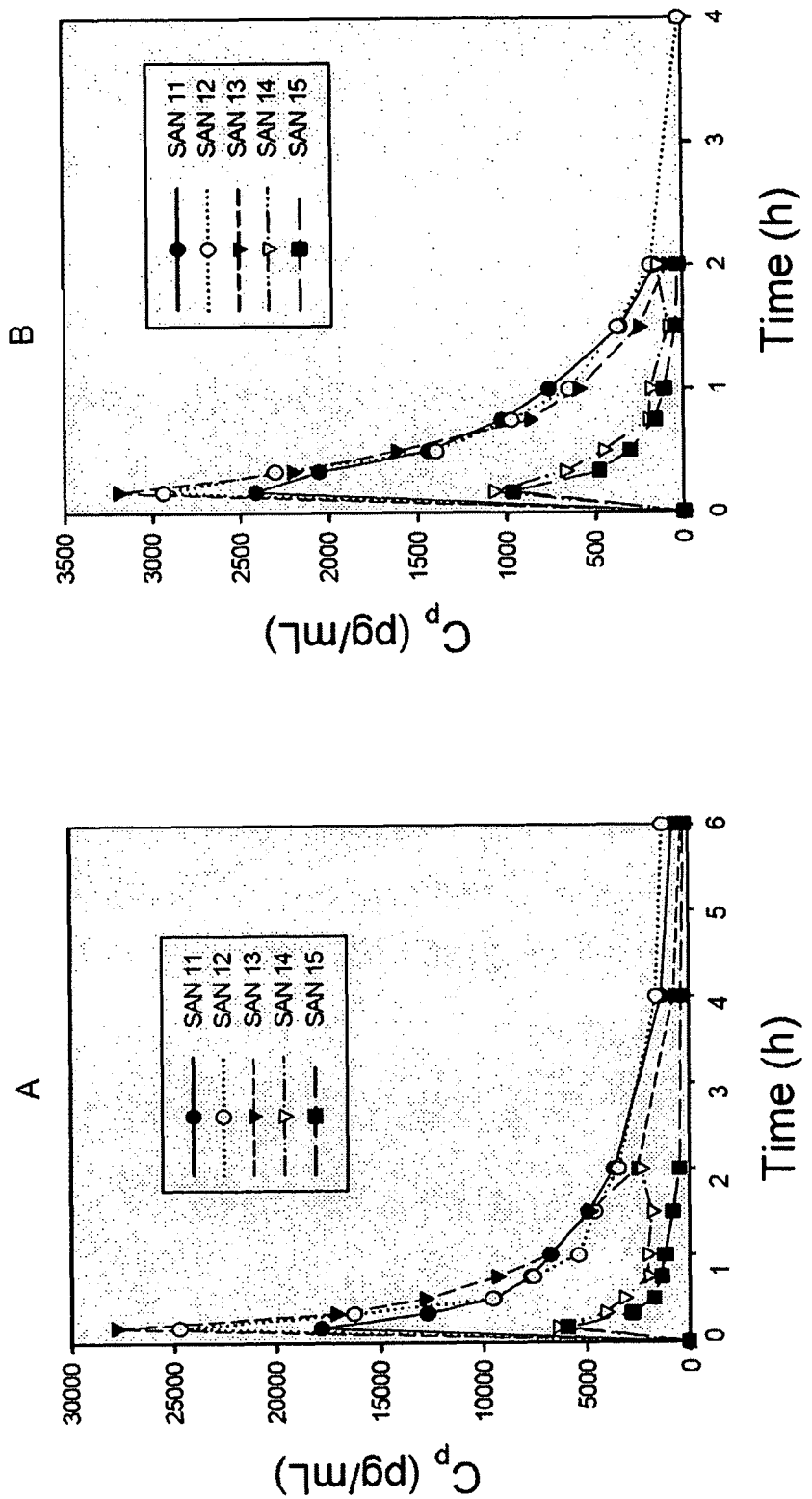
FIG. 27 shows group 3, fentanyl (A) and naltrexone (B) individual plasma concentrations in male sprague dawley rats following a single intraperitoneal co-administration of fentanyl (125 µg/kg) and naltrexone (12.5 µg/kg).

The mean plasma concentrations versus time profiles for naltrexone are plotted in FIG. 23 whereas the individual plots for fentanyl and naltrexone are provided in FIGS. 25, 26, and 27 for groups 1, 2, and 3, respectively. The mean pharmacokinetic metrics for naltrexone are recorded in Table 12, whereas individual rat pharmacokinetic metrics are listed in Tables 14, 15, and 16 for the respective groups. The individual plasma concentration versus time profiles were highly variable for Group 1 (highest dose of naltrexone). The $t_{max}$ value for all rats was 10 min, which was the first time point post injection. The $t_{1/2}$ values were similar for all three groups and ranged from 0.388 to 0.714 h (the terminal $t_{1/2}$ values were not calculable from one rat in each of Groups 1 and 3). The $C_{max}$ values ranged from 762 to 30864 pg/mL for Group 1, 5169 to 7832 pg/mL for Group 2 and 963 to 3196 pg/mL for Group 3. The $AUC_{inf}$ values ranged from 445 to 18947 pg·h/mL, 2731 to 4149 pg·h/mL, and 426 to 2092 pg·h/mL for Groups 1, 2, and 3, respectively.

The mean plasma concentrations versus time profiles for norfentanyl are plotted in FIG. 24. The mean pharmacokinetic metrics for norfentanyl are recorded in Table 16, whereas individual rat pharmacokinetic metrics are listed in Tables 17, 18, and 19 for Groups 1, 2, and 3, respectively. The plasma concentration profiles and the pharmacokinetic metrics were similar for all three groups since all rats received 125 µg/kg of fentanyl. The individual plasma concentration versus time profiles for norfentanyl were less variable than the fentanyl or naltrexone profiles. Norfentanyl concentration was proportionately higher in most of the rats with lower than average plasma concentrations of fentanyl. The $t_{max}$ values ranged from 10 min to 2.0 hours post injection. The $t_{1/2}$ values were similar to fentanyl and similar for all three groups with values ranging from 1.41 to 3.48 h (the terminal $t_{1/2}$ values were not calculable from one rat in Group 1). The $C_{max}$ values ranged from 1595 to 3572 pg/mL for Group 1, 1238 to 2273 pg/mL for Group 2 and 911 to 3019 pg/mL for Group 3. The $AUC_{inf}$ values ranged from 4897 to 6134 pg·h/mL for Group 1, 4781 to 7689 pg·h/mL for Group 2, and 4303 to 6203 pg·h/mL for Group 3.

While it was possible to quantitate 6-β-naltrexol concentrations in the plasma of the Group 1 rats, there were only a few time points/rat where concentrations were substantially above the LLOQ (10 pg/mL). No further analysis was conducted.

Figure 28:
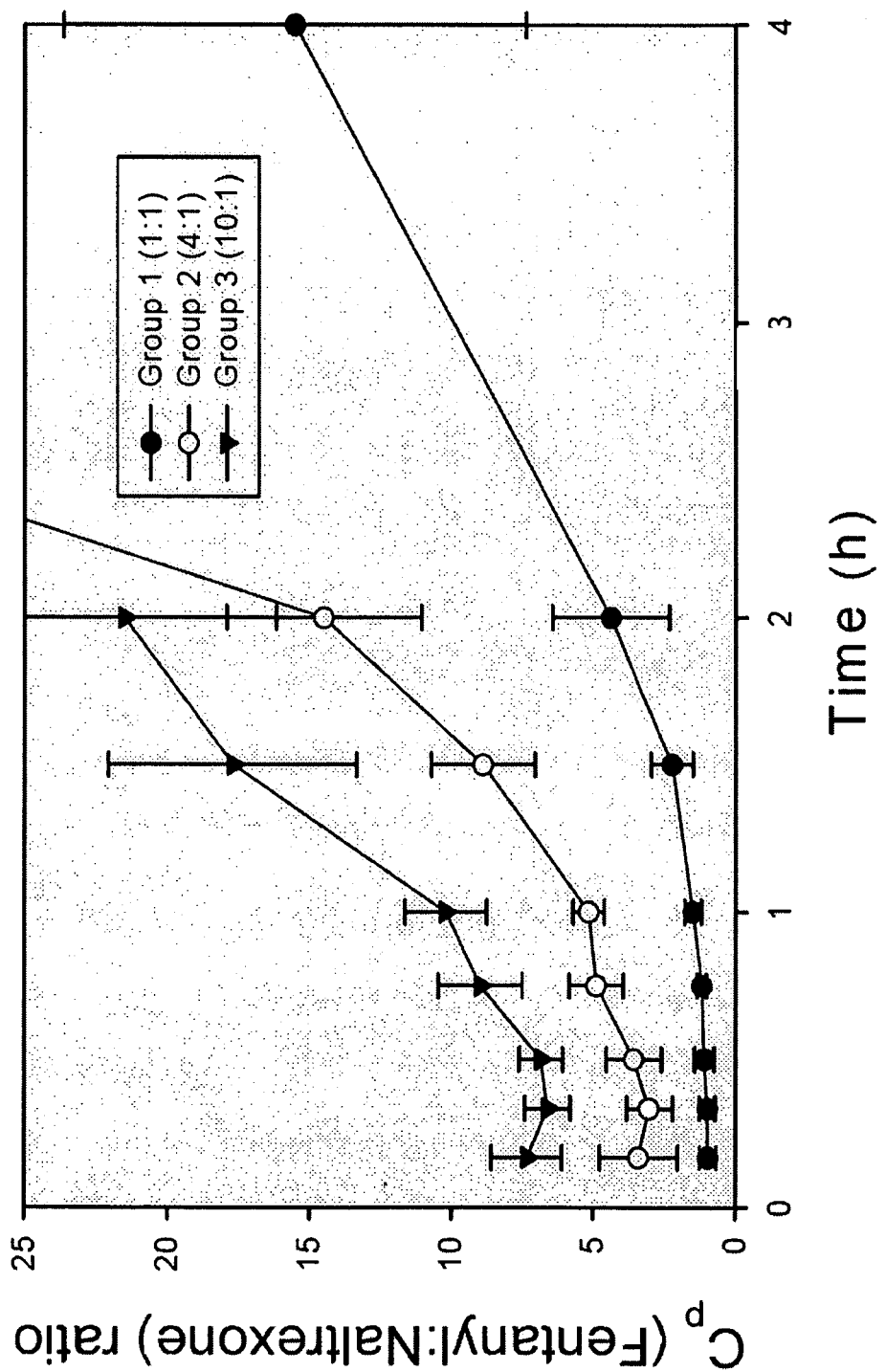
FIG. 28 shows ratio of mean plasma concentrations of fentanyl to naltrexone in male sprague dawley rats following a single intraperitoneal co-administration of fentanyl and naltrexone.

The ratios of mean plasma concentrations of fentanyl to naltrexone for the 3 groups are plotted in FIG. 28. While there was large intra-rat variability in the plasma concentrations of fentanyl and naltrexone, the variability in the plasma concentration ratio was small. The targeted plasma concentration ratios were not obtained until 0.5 to 1 h after injection. Throughout the early time points, the plasma concentration of fentanyl was proportionally lower than that of naltrexone. At later time points, the concentration ratio of fentanyl to naltrexone in the plasma of the rats increased due to the more rapid elimination of naltrexone which has a shorter plasma half-life. Although this produces a higher ratio of fentanyl to naltrexone in the plasma at later time points, the absolute concentration of fentanyl has also decreased, hence the lack of any clinical signs due to fentanyl administration in the rats.

There was no sign of sedation in any of the rats. All activity appeared to be normal throughout the 6-h of the study.

There was considerable variation in fentanyl and naltrexone plasma concentrations in all three groups. However, the ratio of fentanyl to naltrexone in the plasma was more consistent within the three groups across the sampling time points tested. Furthermore, the ratio of fentanyl to naltrexone plasma concentration increased with time owing to the longer plasma half-life of fentanyl. The target (dosed) ratios were reached at approximately 30 min to 1 h post dose. The cage-side observations for the co-administered fentanyl and naltrexone demonstrated a lack of sedative effect of fentanyl at all 3 ratios of agonist to antagonist and at all time points studied. Although the relative concentration of fentanyl to naltrexone within the plasma of the rat increased with time, the absolute concentration of fentanyl in the plasma decreased so no clinical effects were observed.

TABLE 14

Fentanyl Mean Pharmacokinetic Metrics in Male Sprague Dalwey Rats Following a Single Co-administration of Fentanyl and Naltrexone Via Intraperitoneal Injection

| PK Metric | | Group 1 | Group 2 | Group 3 |
|---|---|---|---|---|
| $C_{max}$ (pg/mL) | Mean | 14916 | 22176 | 16555 |
| | SD | 14459 | 12981 | 10134 |
| | CV (%) | 96.9 | 58.5 | 61.2 |

TABLE 14-continued

Fentanyl Mean Pharmacokinetic Metrics in Male Sprague Dalwey Rats Following a Single Co-administration of Fentanyl and Naltrexone Via Intraperitoneal Injection

| PK Metric | | Group 1 | Group 2 | Group 3 |
|---|---|---|---|---|
| $t_{max}$ (h) | Mean | 0.167 | 0.167 | 0.167 |
| | SD | 0.0 | 0.0 | 0.0 |
| | CV (%) | 0.0 | 0.0 | 0.0 |
| $AUC_{inf}$ (pg·h/mL) | Mean | 3473 | 7923 | 9519 |
| | SD | 141 | 5007 | 5215 |
| | CV (%) | 4.05 | 63.2 | 54.8 |
| $t_{1/2}$ (h) | Mean | 1.41 | 1.40 | 1.69 |
| | SD | 0.504 | 0.579 | 0.459 |
| | CV (%) | 35.7 | 41.3 | 27.2 |

TABLE 15

Naltrexone Mean PK Metrics in Male Sprague Dalwey Rats Following a Single Co-administration of Fentanyl and Naltrexone Via Intraperitoneal Injection

| PK Metric | | Group 1 | Group 2 | Group 3 |
|---|---|---|---|---|
| $C_{max}$ (pg/mL) | Mean | 15099 | 6155 | 2116 |
| | SD | 12433 | 1126 | 1042 |
| | CV (%) | 82.3 | 18.3 | 49.3 |
| $t_{max}$ (h) | Mean | 0.167 | 0.167 | 0.167 |
| | SD | 0.0 | 0.0 | 0.0 |
| | CV (%) | 0.0 | 0.0 | 0.0 |
| $AUC_{inf}$ (pg·h/mL) | Mean | 9416 | 3771 | 1340 |
| | SD | 8490 | 600 | 779 |
| | CV (%) | 90.2 | 15.9 | 58.2 |
| $t_{1/2}$ (h) | Mean | 0.562 | 0.448 | 0.439 |
| | SD | 0.118 | 0.0291 | 0.077 |
| | CV (%) | 20.9 | 6.5 | 17.6 |

TABLE 16

Norfentanyl Mean PK Metrics in Male Sprague Dalwey Rats Following a Single Co-administration of Fentanyl and Naltrexone Via Intraperitoneal Injection

| PK Metric | | Group 1 | Group 2 | Group 3 |
|---|---|---|---|---|
| $C_{max}$ (pg/mL) | Mean | 2551 | 1907 | 1809 |
| | SD | 853 | 438 | 986 |
| | CV (%) | 33.4 | 23.0 | 54.5 |
| $t_{max}$ (h) | Mean | 0.350 | 0.783 | 0.983 |
| | SD | 0.266 | 0.492 | 0.662 |
| | CV (%) | 75.9 | 62.8 | 67.4 |
| $AUC_{inf}$ (pg·h/mL) | Mean | 4939 | 5131 | 4094 |
| | SD | 435 | 917 | 801 |
| | CV (%) | 8.8 | 17.9 | 19.6 |
| $t_{1/2}$ (h) | Mean | 1.69 | 2.01 | 2.33 |
| | SD | 0.103 | 0.424 | 1.00 |
| | CV (%) | 6.1 | 21.1 | 42.8 |

TABLE 17

Individual Pharmacokinetic Metrics in Male Sprague Dalway Rats Following a Single Co-administration of Fentanyl (125 µg/kg) and Naltrexone (125 µg/kg) Via Intraperitoneal Injection

| PK Metric | Analyte | SAN 1 | SAN 2 | SAN 3 | SAN 4 | SAN 5 |
|---|---|---|---|---|---|---|
| $C_{max}$ (pg/mL) | Naltrexone | 12104 | 762 | 30864 | 24658 | 7106 |
| | Fentanyl | 6765 | 980 | 32309 | 28709 | 5815 |
| | Norfentanyl | 2474 | 3572 | 1595 | 1870 | 3245 |
| $t_{max}$ (h) | Naltrexone | 0.167 | 0.167 | 0.167 | 0.167 | 0.167 |
| | Fentanyl | 0.167 | 0.167 | 0.167 | 0.167 | 0.167 |
| | Norfentanyl | 0.167 | 0.167 | 0.750 | 0.500 | 0.167 |

TABLE 17-continued

Individual Pharmacokinetic Metrics in Male Sprague Dalway Rats Following a Single Co-administration of Fentanyl (125 µg/kg) and Naltrexone (125 µg/kg) Via Intraperitoneal Injection

| PK Metric | Analyte | SAN 1 | SAN 2 | SAN 3 | SAN 4 | SAN 5 |
|---|---|---|---|---|---|---|
| $AUC_{inf}$ (pg · h/mL) | Naltrexone | 5895 | 445 | 18947 | 18009 | 3853 |
| | Fentanyl | 8657 | NC | 28382 | 25082 | 7301 |
| | Norfentanyl | 6134 | NC | 4897 | 5842 | 5114 |
| $t_{1/2}$ (h) | Naltrexone | 0.602 | 0.388 | 0.566 | 0.540 | 0.714 |
| | Fentanyl | 1.90 | NC | 1.15 | 0.841 | 1.76 |
| | Norfentanyl | 1.80 | NC | 1.75 | 1.57 | 1.64 |

TABLE 18

Individual Pharmacokinetic Metrics in Male Sprague Dalway Rats Following a Single Co-administration of Fentanyl (125 µg/kg) and Naltrexone (31.3 µg/kg) Via Intraperitoneal Injection

| PK Metric | Analyte | SAN 6 | SAN 7 | SAN 8 | SAN 9 | SAN 10 |
|---|---|---|---|---|---|---|
| $C_{max}$ (pg/mL) | Naltrexone | 5865 | 5169 | 6705 | 5204 | 7832 |
| | Fentanyl | 19645 | 10778 | 27269 | 11220 | 41969 |
| | Norfentanyl | 1692 | 2273 | 2109 | 1238 | 2224 |
| $t_{max}$ (h) | Naltrexone | 0.167 | 0.167 | 0.167 | 0.167 | 0.167 |
| | Fentanyl | 0.167 | 0.167 | 0.167 | 0.167 | 0.167 |
| | Norfentanyl | 0.750 | 0.333 | 1.00 | 1.50 | 0.333 |
| $AUC_{inf}$ (pg · h/mL) | Naltrexone | 4149 | 2731 | 4065 | 3825 | 4132 |
| | Fentanyl | 22036 | 16824 | 23072 | 20404 | 23552 |
| | Norfentanyl | 5467 | 7689 | 6802 | 5444 | 4781 |
| $t_{1/2}$ (h) | Naltrexone | 0.426 | 0.465 | 0.431 | 0.429 | 0.492 |
| | Fentanyl | 1.11 | 2.35 | 1.12 | 1.54 | 0.891 |
| | Norfentanyl | 1.90 | 2.48 | 1.72 | 2.42 | 1.53 |

TABLE 19

Individual Pharmacokinetic Metrics in Male Sprague Dalway Rats Following a Single Co-administration of Fentanyl (125 µg/kg) and Naltrexone (12.5 µg/kg) Via Intraperitoneal Injection

| PK Metric | Analyte | SAN 11 | SAN 12 | SAN 13 | SAN 14 | SAN 15 |
|---|---|---|---|---|---|---|
| $C_{max}$ (pg/mL) | Naltrexone | 2409 | 2938 | 3196 | 1073 | 963 |
| | Fentanyl | 17851 | 24730 | 27825 | 6417 | 5950 |
| | Norfentanyl | 911 | 965 | 1457 | 2692 | 3019 |
| $t_{max}$ (h) | Naltrexone | 0.167 | 0.167 | 0.167 | 0.167 | 0.167 |
| | Fentanyl | 0.167 | 0.167 | 0.167 | 0.167 | 0.167 |
| | Norfentanyl | 1.00 | 0.750 | 1.00 | 2.00 | 0.167 |
| $AUC_{inf}$ (pg · h/mL) | Naltrexone | 1903 | 2092 | 1870 | NC | 426 |
| | Fentanyl | 23772 | 27690 | 23180 | NC | 5387 |
| | Norfentanyl | 5096 | 5245 | 4303 | 9417 | 6203 |
| $t_{1/2}$ (h) | Naltrexone | 0.460 | 0.539 | 0.363 | NC | 0.396 |
| | Fentanyl | 1.51 | 2.09 | 1.12 | NC | 2.03 |
| | Norfentanyl | 3.34 | 3.48 | 1.60 | 1.41 | 1.81 |

Example 19

This study was designed to obtain transbuccal flux data and the pharmacokinetic profile of the three different 7-day 3M transdermal fentanyl formulations and the Duragesic® formulation. The appearance in plasma and the plasma pharmacokinetic profile of naltrexone was also monitored in this study.

A group of 9 male Beagle dogs were used in a modified crossover design. In the first phase of the study, the dogs received a single buccal application of fentanyl for 30 minutes as Duragesic® gel (3 dogs) or as a Duragesic® chiclet (6 dogs). Following a 3-week washout period, the dogs received a single 30-minute buccal application of fentanyl from one of three prototype transdermal systems (3 dogs/formulation, 2Di, 1Ci or the U2b. After a second 3-week washout period, all 9 dogs were administered a single intravenous (IV) co-injection of fentanyl and naltrexone (as 45 µg/kg of each opiate).

Blood was collected from each dog in each phase of the study at predose, 5, 10, 20, 30, 45, and 60 minutes, and at 2, 3, 4, 6, 8, and 24 hours post fentanyl dose. The separated plasma was stored at −20° C. until analyzed by LC-MS-MS for fentanyl, norfentanyl, naltrexone, and 6-β-naltrexol concentrations. The standard curves for fentanyl and its metabolite ranged from 50 to 1000 pg/mL, whereas the standard curves for naltrexone and 6-β-naltrexol ranged from 10 1 to 505 pg/mL.

Following the administration of Duragesic® gel to the buccal mucosa of 3 dogs, a similar fentanyl plasma $C_{max}$ (mean of 1371 pg/mL), $AUC_{last}$ (mean of 3473 pg·h/mL) and fentanyl plasma concentration versus time profile was obtained. When a Duragesic® chiclet of 2 cm² was applied to the buccal mucosa, substantial inter-dog (n=6) variability was found in the concentration versus time profile. This was predominantly due to the variability in the making of the chiclets (i.e., the amount of gel within the 2 cm² chiclet) than in the dogs' individual absorption and pharmacokinetics. The fentanyl plasma $C_{max}$ values ranged from 1355 to 5031 pg/mL (mean of 3095 pg/mL), and the $AUC_{last}$ (mean of 7923 pg·h/mL) showed a similar inter-dog variability over the 6 dogs studied.

The 3M formulation, U2b, produced the most variability of any formulation tested in the fentanyl plasma concentration versus time profile. The $C_{max}$ values ranged from 2204 to 12900 pg/mL (mean of 6532 pg/mL) and the $AUC_{inf}$ ranged from 4337 to 15719 pg·h/mL.

Following application of the 2Di transdermal formulation to the buccal mucosa of the dogs, the fentanyl and naltrexone plasma concentration profiles as well as the associated pharmacokinetic (PK) metrics were consistent among the 3 dogs. The $C_{max}$ fentanyl ranged from 2908 to 4208 pg/mL, and the $t_{max}$ ranged from 0.3 to 0.5 hours. The $AUC_{inf}$ values ranged from 5948 to 8890 pg·h/mL, and the $t_{1/2}$ values ranged from 1.6-2.1 hours. The $C_{max}$ for naltrexone ranged from 963 to 1651 pg/mL, the $t_{max}$ ranged from 0.5 to 0.8 hours, and the $AUC_{inf}$ values ranged from 1764 to 3139 pg·h/mL. The $t_{1/2}$ values ranged from 0.8 to 1-2 hours, approximately 50% of the fentanyl $t_{1/2}$ values.

A fentanyl to naltrexone ratio as low as 2:1 was maintained from 20 minutes until approximately 90 minutes post buccal application of the 2Di transdermal formulation.

Following the application of the 1Ci transdermal formulation to the buccal mucosa of the dogs, the fentanyl and naltrexone plasma concentration profiles as well as the associated PK metrics were also consistent among the three dogs. The fentanyl plasma $C_{max}$ ranged from 7369 to 9821 pg/mL which was higher than with the 2Di formulation. The fentanyl plasma $AUC_{inf}$ values ranged from 9926 to 13168 pg·h/mL (also substantially higher than that obtained with the 2Di formulation). The associated $t_{max}$ values ranged from 0.3 to 0.5 hours, and the $t_{1/2}$ values ranged from 2.0-2.2 hours. The naltrexone metrics were similar to the naltrexone metrics with the 2Di formulation. The naltrexone plasma $C_{max}$ values with the 1Ci transdermal formulation ranged from 1011 to 1637 pg/mL, the $t_{max}$ ranged from 0.3 to 0.8 hours, and the naltrexone $AUC_{inf}$ values ranged from 1121 to 1709 pg·h/mL. The $t_{1/2}$ values or naltrexone were approximately half the value for fentanyl, from 0.90-1.0 h.

For this formulation, it was not possible to achieve a 2:1 fentanyl to naltrexone ratio in any of the 3 dogs. While the naltrexone concentration in the plasma is similar to the 2Di formulation, the plasma concentration of fentanyl was higher, most likely due to the presence of the permeation enhancer within the adhesive layer.

The cage side observations for the co-administered fentanyl plus naltrexone validated the ability of a 1:1 ratio of naltrexone to fentanyl to block the sedative effect of fentanyl. While both the 1Ci and 2Di formulations delivered naltrexone to the systemic circulation, the 2Di formulation was more effective at delivering naltrexone (faster and higher systemic concentrations) and had a slower delivery of fentanyl. This combination resulted in plasma naltrexone:fentanyl ratios as low as 1:2 from 20 to 90 minutes post application. This was also confirmed by a higher trans-buccal flux rate for naltrexone than fentanyl with the 2Di formulation.

The modified cross-over experimental design for the study was as follows:

TABLE 20

| Group[a] | N | Treatment | Phase | Dosing | Route |
|---|---|---|---|---|---|
| 1 | 3 | Duragesic ® gel | 1 | 30 µL | Buccal |
| 2 | 6 | Duragesic ® chiclet | 1 | 2 cm² | Buccal |
| 3 | 3 | U2b | 2 | 2 cm² | Buccal |
| 4 | 3 | 2Di | 2 | 2 cm² | Buccal |
| 5 | 3 | 1Ci | 2 | 2 cm² | Buccal |
| 6 | 9 | Fentanyl plus naltrexone | 3 | 45 µg/kg of each | IV |

[a] A total of 9 dogs were used in this study. The dogs from groups 1 and 2 were the same dogs used in groups 3, 4 and 5, and 6. A minimum of a 3-week washout period occurred between each phase.

All dogs in groups 1 through 5 received naloxone (20 µg/kg) as a slow (approximately 30-second) IV bolus (400 µg/mL) approximately 30 minutes prior to buccal application of fentanyl.

Group 1. Three dogs were administered 30 µL of Duragesic® gel, using a positive displacement pipette, to the area between the gum and cheek. The dogs' mouths were held closed, and pressure was applied to hold the cheek against the teeth/gums for 30 minutes. Blood samples were collected at the times indicated below.

Group 2. In six dogs, a 2 cm² (approximately) chiclet of Duragesic® was applied to the area between the gum and cheek. The dogs' mouths were held closed, and pressure was applied to hold the cheek against the teeth/gums for 30 minutes. Blood samples were collected at the times indicated below.

Group 3, 4 and 5. After a washout period of 3 weeks, the 9 dogs (from groups 1 and 2) were split into three groups. Three dogs were assigned to groups 3, 4, and 5. The dogs in group 3 had a 2 cm² U2b prototype fentanyl transdermal system placed between the gum and cheek. The dogs in group 4 received a 2 cm² transdermal patch of the 2Di formulation while those in group 5 received the 1Ci formulation applied in the same manner. The dogs' mouths were held closed and pressure was applied to hold the cheek against the teeth/gums for 30 minutes. Blood samples were collected at the times indicated below.

Group 6. Following an additional 3-week washout period, each of the nine dogs received fentanyl and naltrexone, 45 µg/kg each, as a co-injection into the non-cannulated (contralateral) cephalic vein. Blood samples were collected at the times indicated below.

Blood collection: The blood was collected into polypropylene tubes containing $K_2EDTA$, labeled with at least the following information: study number, dose group, animal number, and time of collection. Approximately 3 mL was collected via the cephalic (or saphenous) cannula from each dog at preclose, 5, 10, 20, 30, 45 and 60 min, and at 2, 3, 4, 6, and 8 hours post fentanyl dose. A 24-hour post-dose sample was obtained from the jugular or cephalic vein. The blood samples were kept on ice until separation of plasma (usually within 1 hour of collection). Blood samples were centrifuged at 4° C., and the resulting plasma separated and stored in appropriately labeled polypropylene containers at approximately −70° C. until analysis.

The plasma samples (0.200 mL) were analyzed for fentanyl, norfentanyl, naltrexone, and 6-β-naltrexol concentrations. After the addition of internal standards, the samples were subjected to solid phase extraction. The extract was dried and resuspended in 100 µL acetonitrile and analyzed by LC-MS/MS. The standard curves were linear over the range of 50.0 to 1,000 pg/mL for fentanyl and norfentanyl. The naltrexone and 6-β-naltrexol standard curves were linear over the range of 10.1 to 505 pg/mL. Samples that exceeded the standard curve were diluted with interference-free plasma and re-analyzed.

The non-compartmental pharmacokinetic metrics from the mean plasma concentration data were determined using WinNonlin, version 1.5. The AUC value was estimated by the linear trapezoidal rule. Zero was used for any concentration that was less than the LLOQ of the assay. The apparent $t_{1/2}$ was calculated as $t_{1/2}$=0.693/λ where λ is the elimination rate constant estimated from the regression of the terminal slope of the concentration versus time curve. At least 3 plasma concentrations after the peak concentration on the terminal phase were used to determine λ, and the coefficient of determination ($R^2$) was required to be greater than or equal to 0.85.

The plasma clearance of fentanyl and naltrexone was calculated by WinNonlin from the I.V. data for each dog. These values were used to calculate the transbuccal flux of fentanyl and naltrexone for each dog with the various formulations administered.

$$Flux = \frac{AUC_{buccal} \times Clearance_{IV}}{Area_{patch} \times t_{buccal-application}}$$

The calculated results are an approximation since the equation assumes steady-state delivery which in the dog model normally takes one hour (Cassidy, J. P., et al., "Controlled buccal delivery of buprenorphine," *J. Controlled Release* 25:21-29 (1993)).

The mean PK metrics for fentanyl, naltrexone, and norfentanyl are listed in Tables 21, 22, and 23, respectively.

Figure 29:
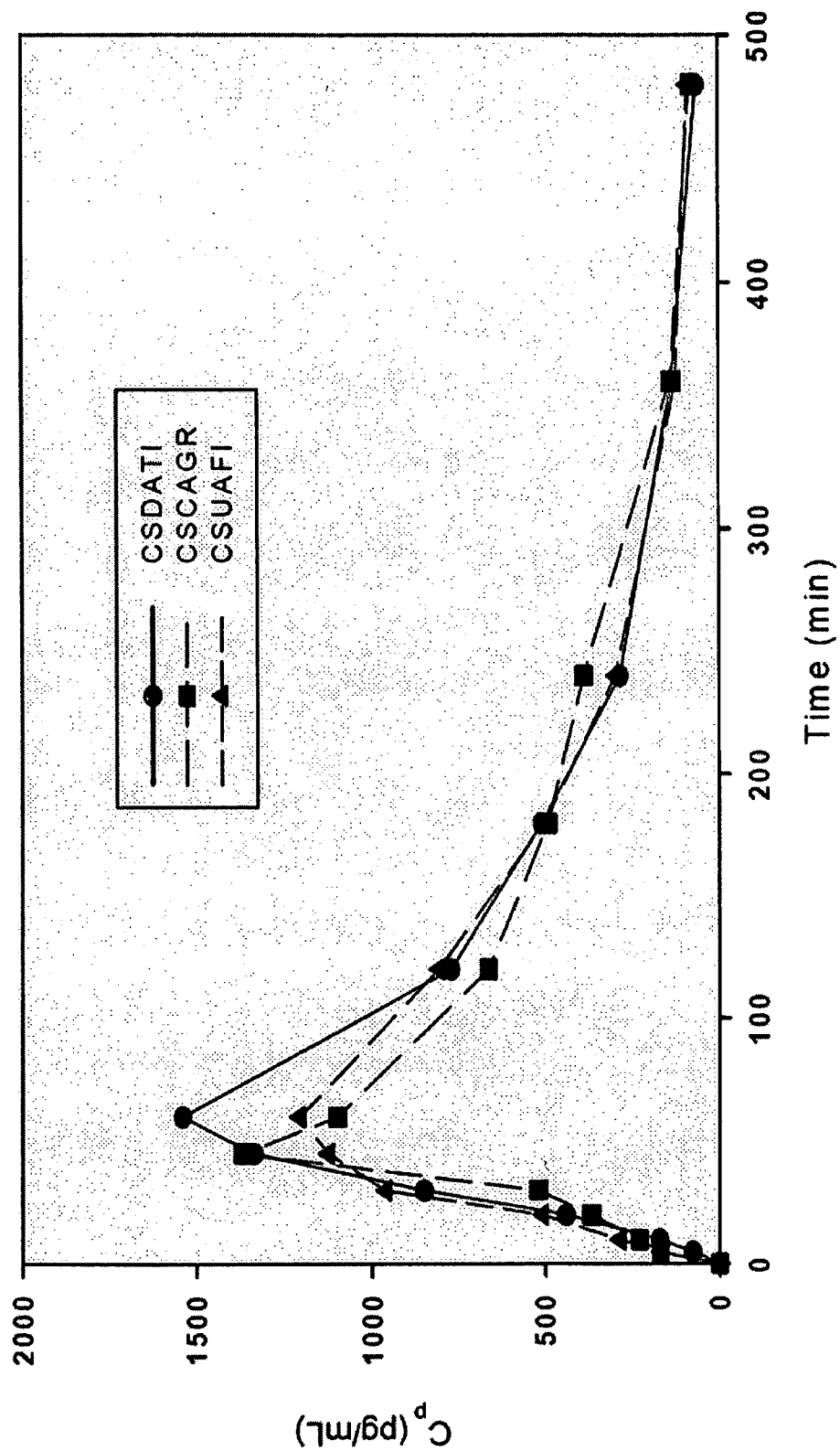
FIG. 29 shows individual plasma concentrations of fentanyl following the buccal administration of 30 µl (approximately 0.9 mg fentanyl free-base) Duragesic® gel to male beagle dogs.

The individual fentanyl plasma concentration versus time profiles for the buccal application of 30 μL of Duragesic® gel to dogs (animal numbers CSDATI, CSCAGR, and CSUAFI) are plotted in FIG. 29 and the individual PK metrics are listed in Table 24. The plasma concentration profiles and the PK metrics were similar for all three dogs. The $C_{max}$ values ranged from 1206 to 1539 pg/mL while the $t_{max}$ values were approximately 1 hour (0.75-100 h) The $AUC_{inf}$ values ranged from 3555 to 3763 pg·h/mL while $t_{1/2}$ ranged from 1.6 to 18 hours.

Figure 30:
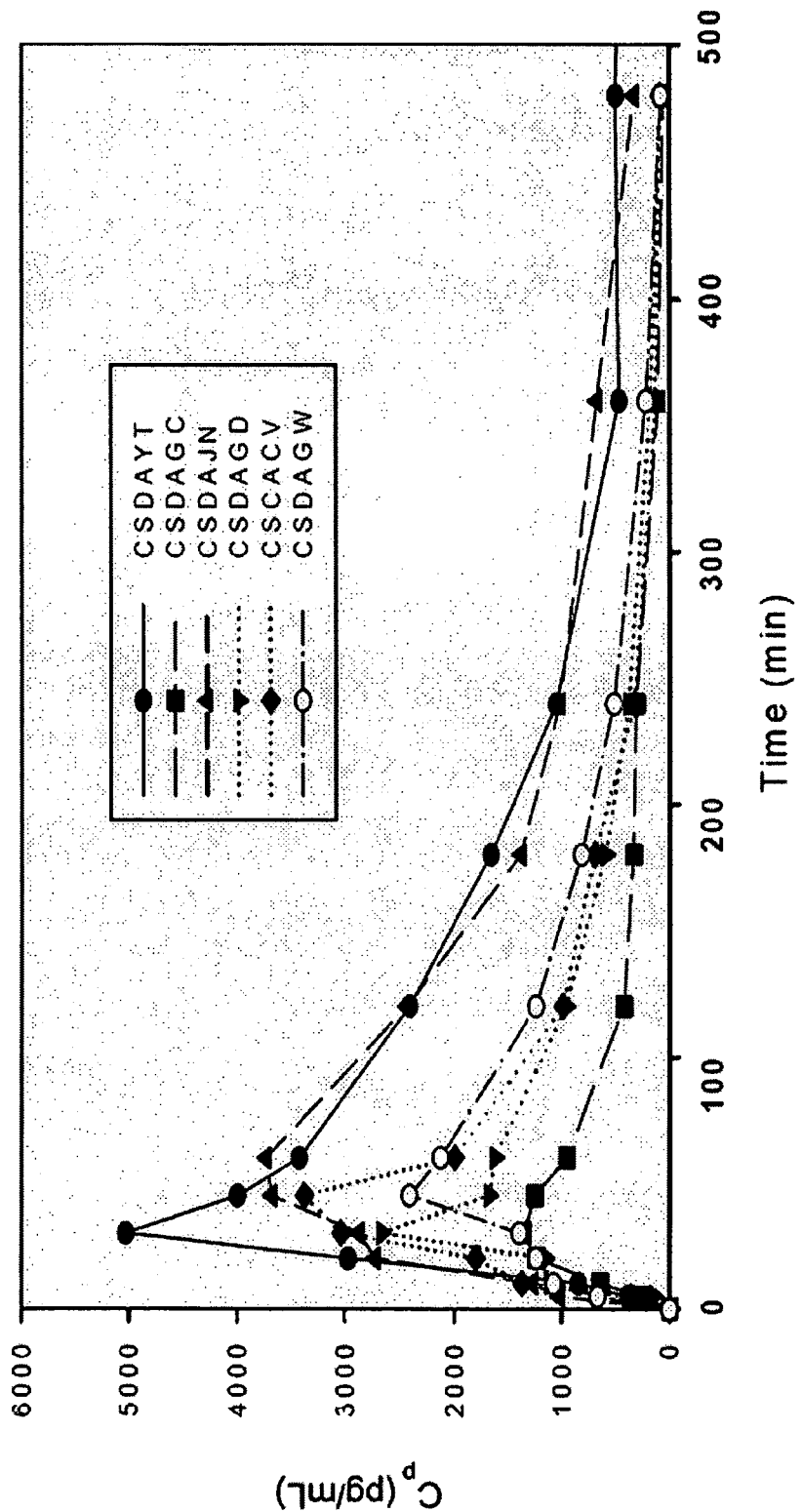
FIG. 30 shows individual plasma concentrations of fentanyl following the 30 minute application of a 2 $cm^2$ Duragesic® chiclet to the buccal mucosa of male beagle dogs.

The individual fentanyl plasma concentration versus time profiles for the 30-minute buccal application of a 2 cm² chiclet of Duragesic® are plotted in FIG. 30. Individual PK metrics are listed in Table 22. The plasma concentration profiles and the PK metrics demonstrated a wide variability among the 6 dogs (animal numbers CSCACV, CSDAGC, CSDAGD, CSDAGW, CSDAJN, and CSDAYT). The $C_{max}$ ranged from 1355 to 5031 pg/mL, the $t_{max}$ ranged from 0.5 to 1 hour, and the $AUC_{inf}$ values ranged from 3175 to 16683 pg·h/mL. The $t_{1/2}$ ranged from 1.5 to 2.1 hour in the 5 dogs where the 24-hour plasma concentration of fentanyl was BLQ. For dog CSDAGC, a gamma phase of elimination was detected with a $t_{1/2}$ of 5-0 hours.

Figure 31:
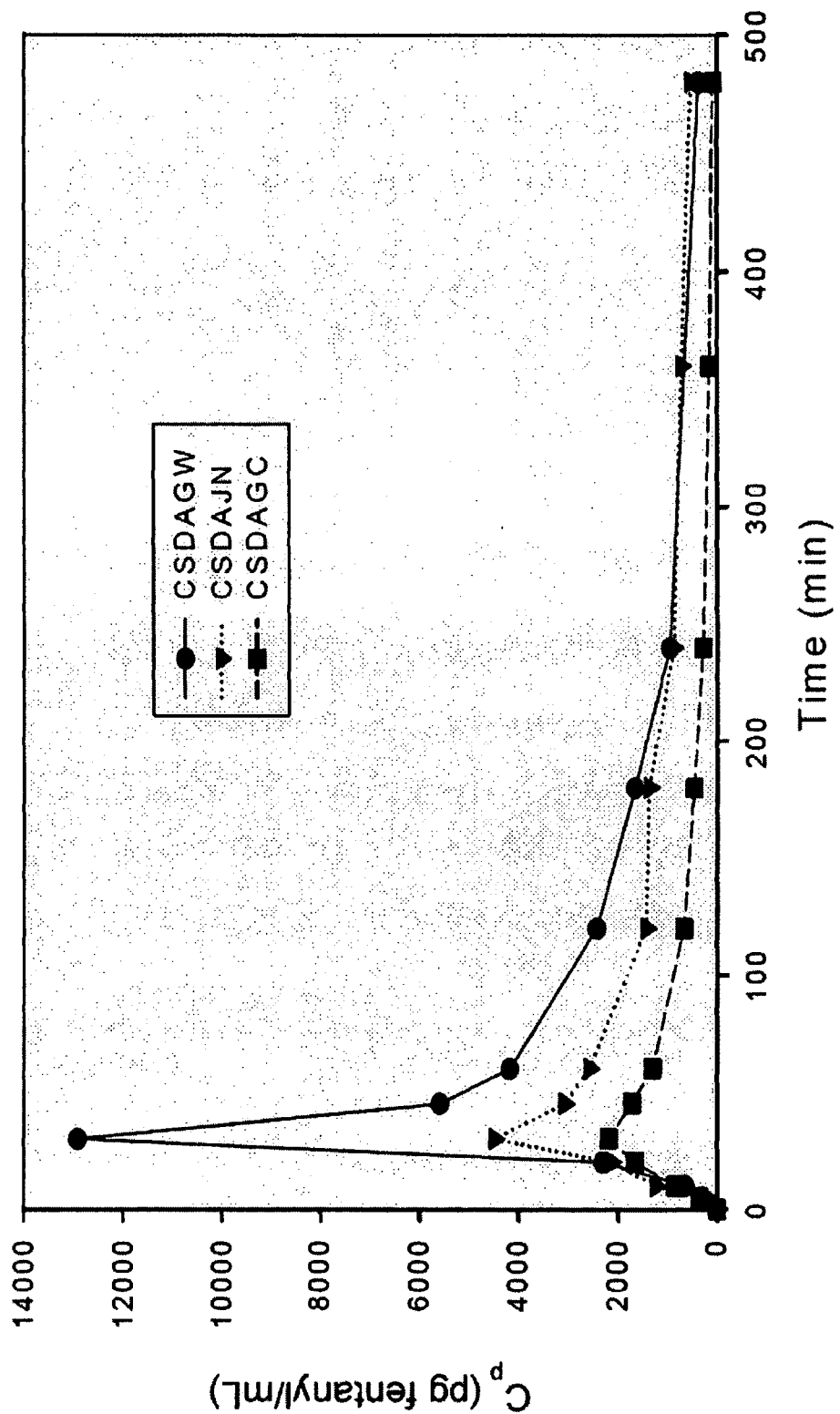
FIG. 31 shows individual plasma concentrations of fentanyl following the 30 minute application of a 2 $cm^2$ U2b transdermal formulation to the buccal mucosa of male beagle dogs.

The individual fental plasma concentration versus time profiles for the 30-minute buccal application of a 2 cm² of formulation U2b (no naltrexone in the formulation) to dogs CSDAGW, CSDAJN, and CSDAGC are plotted in FIG. 31. The individual PK metrics are listed in Table 26. Dog CSDAGW had an extremely high $C_{max}$ when compared to the other two dogs ($C_{max}$ ranged from 2204 to 12900 pg/mL). While the $t_{max}$ was 0.50 hours for all three dogs, the $AUC_{inf}$ values ranged from 4337 to 15719 pg·h/mL with dog CSDAGC providing the low value and the other two dogs at the upper end. The $t_{1/2}$ ranged from 2.1 to 4.1 hours.

Figure 33:
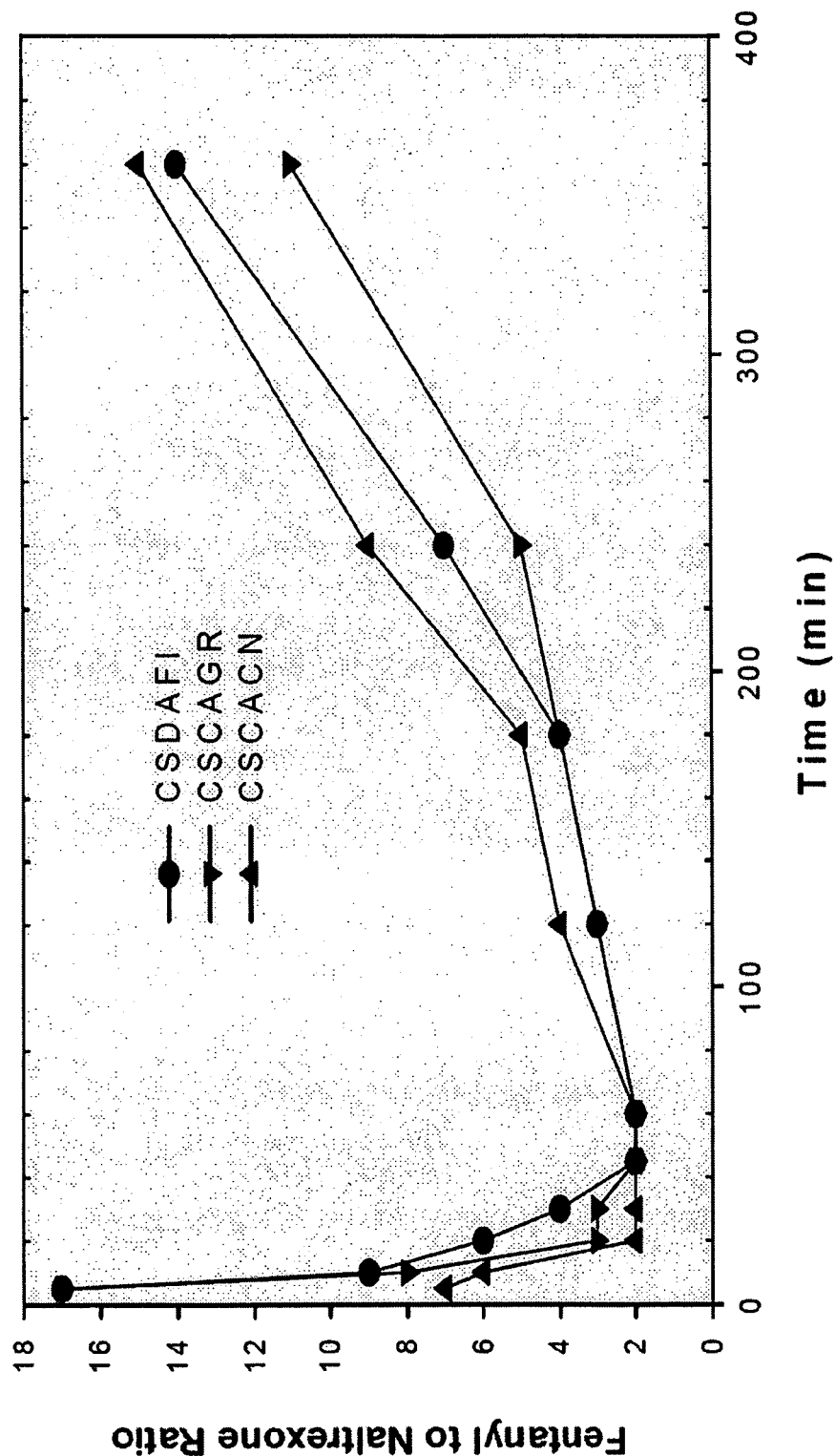
FIG. 33 shows individual plasma concentration ratio of fentanyl to naltrexone following the 30 minute application of a 2 $cm^2$ 2Di transdermal formulation to the buccal mucosa of male beagle dogs.

The individual fentanyl and naltrexone plasma concentration versus time profiles for the 30-minute buccal application of a 2 cm² formulation −2Di to dogs CSDAFI, CSCAGR, and CSGACN are plotted in FIG. 33. Individual PK metrics are listed in Table 27. The fentanyl plasma concentration profiles as well as the associated PK metrics were consistent among the 3 dogs. A similar inter-dog consistency was observed for naltrexone. The fentanyl plasma $C_{max}$ values ranged from 2908 to 4208 pg/mL and the $t_{max}$ values ranged from 0.3 to 0.5 hours. The fentanyl plasma $AUC_{inf}$ values ranged from 5948 to 8890 pg·h/mL, and the $t_{1/2}$ values ranged from 1.6-2.1 hours. The naltrexone plasma $C_{max}$ values ranged from 963 to 1651 pg/mL, the $t_{max}$ ranged from 0.5 to 0.8 hours, and the naltrexone plasma $AUC_{inf}$ values ranged from 1764 to 3139 pg·h/mL. The $t_{1/2}$ values ranged from 0.8-1.2 hours approximately 50% of the fentanyl $t_{1/2}$ values.

Figure 32:
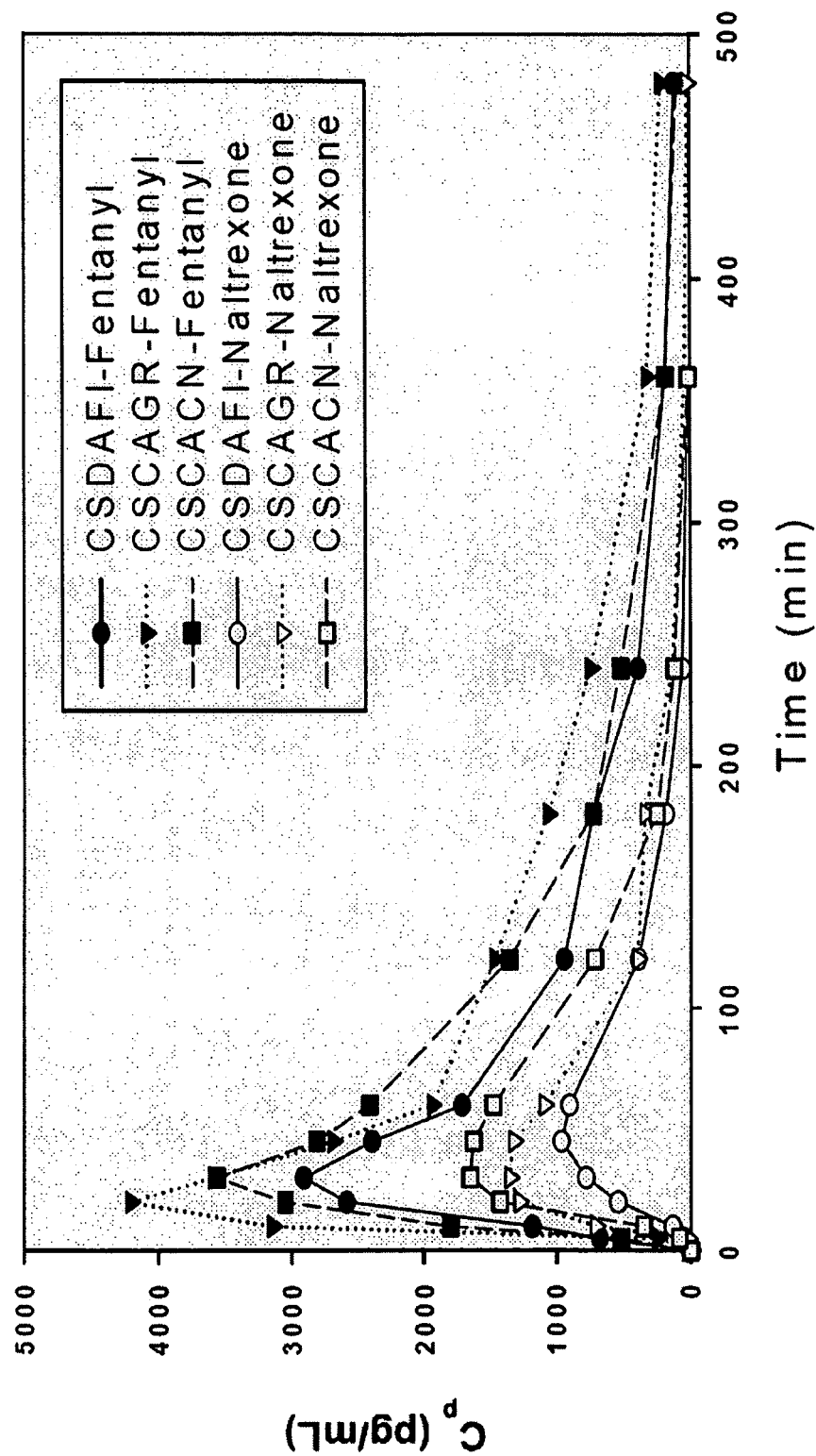
FIG. 32 shows individual plasma concentrations of fentanyl and naltrexone following the 30 minute application of a 2 $cm^2$ 2Di transdermal formulation to the buccal mucosa of male beagle dogs.

The ratios of fentanyl to naltrexone plasma concentrations are plotted in FIG. 32. A ratio as low as 2 fentanyl to one naltrexone was maintained from 20 until 90 minutes post buccal application.

The individual fentanyl and naltrexone plasma concentration vs. time profiles for the 30 minute buccal application of a 2 cm² formulation 1Ci to dogs CSDAGD, CSDATI, and CSDAYT are plotted in FIG. 8G, and the individual PK metrics are listed in Table 28. Similar to the 2Di formulation, the fentanyl plasma concentration profiles and the PK metrics were consistent among the 3 dogs. A similar inter-dog consistency was observed for naltrexone. The fentanyl plasma $C_{max}$ ranged from 7369 to 9821 pg/mL, the $t_{max}$ ranged from 0.3 to 0.5 h, and the fentanyl plasma $AUC_{inf}$ values ranged from 9926 to 13168 pg*hr/mL. The $t_{1/2}$ values ranged from 2.0-2.2 h. The naltrexone plasma $C_{max}$ ranged from 1011 to 1637 pg/mL, the $t_{max}$ ranged from 0.3 to 0.8 h, and the naltrexone plasma $AUC_{inf}$ values ranged from 1121 to 1724 pg*h/mL. The $t_{1/2}$ values for naltrexone were approximately half the value for fentanyl, ranging from 0.90 to 1.0 h.

Figure 34:
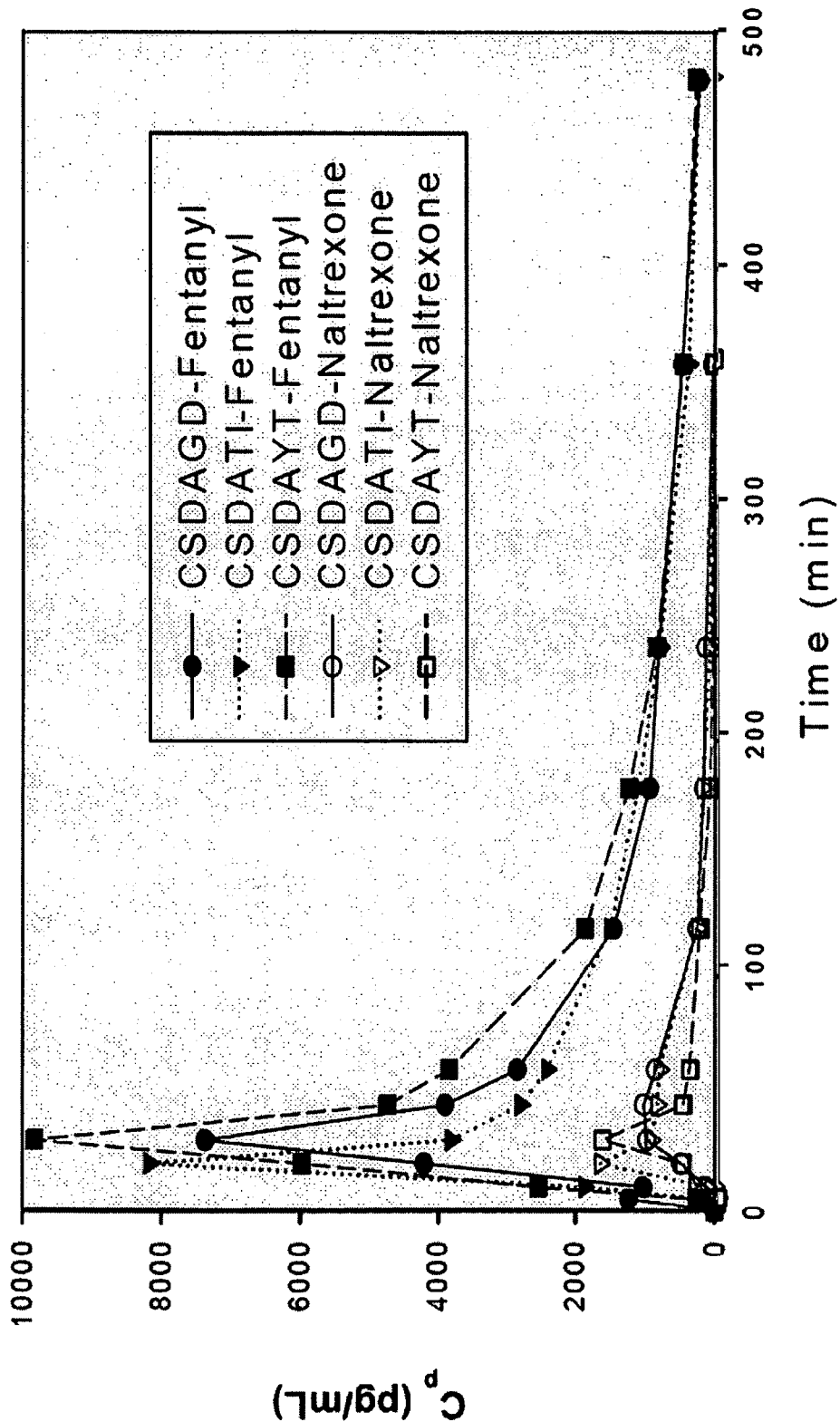
FIG. 34 shows individual plasma concentrations of fentanyl and naltrexone following the 30 minute application of a 2 $cm^2$ 1Ci transdermal formulation to the buccal mucosa of male beagle dogs.
Figure 35:
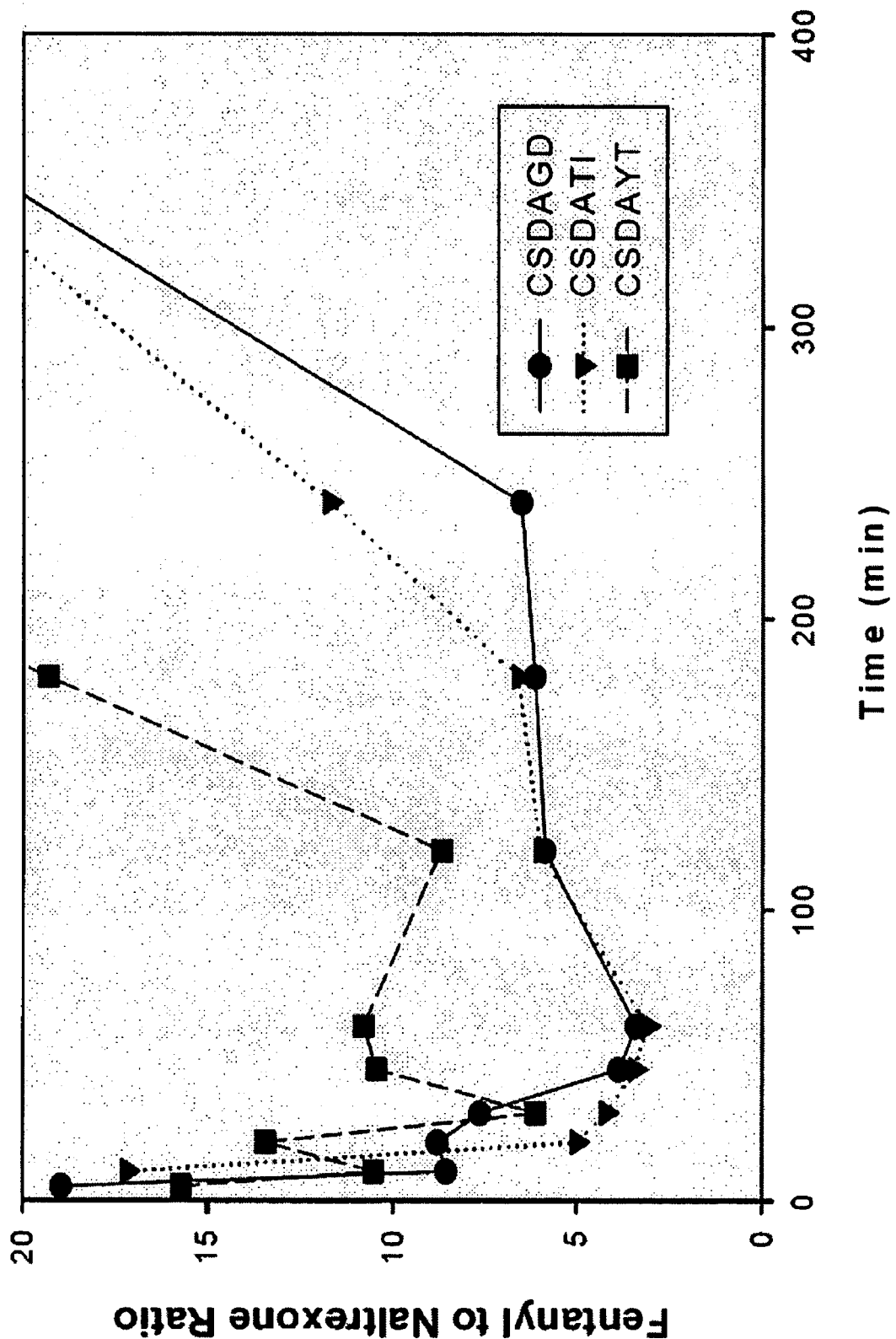
FIG. 35 shows individual plasma concentration ratios of fentanyl and naltrexone following the 30 minute application of a 2 $cm^2$ 1Ci transdermal formulation to the buccal mucosa of male beagle dogs.

The ratio of fentanyl to naltrexone plasma concentrations are plotted in FIG. 34. It was not possible to achieve a 2 fentanyl to 1 naltrexone ratio in any of the 3 dogs with the 1Ci formulation. While the naltrexone concentration in the plasma was similar to the 2Di formulation, the plasma concentration of fentanyl was higher, most likely due to the presence of the permeation enhancer within the adhesive layer.

Figure 36:
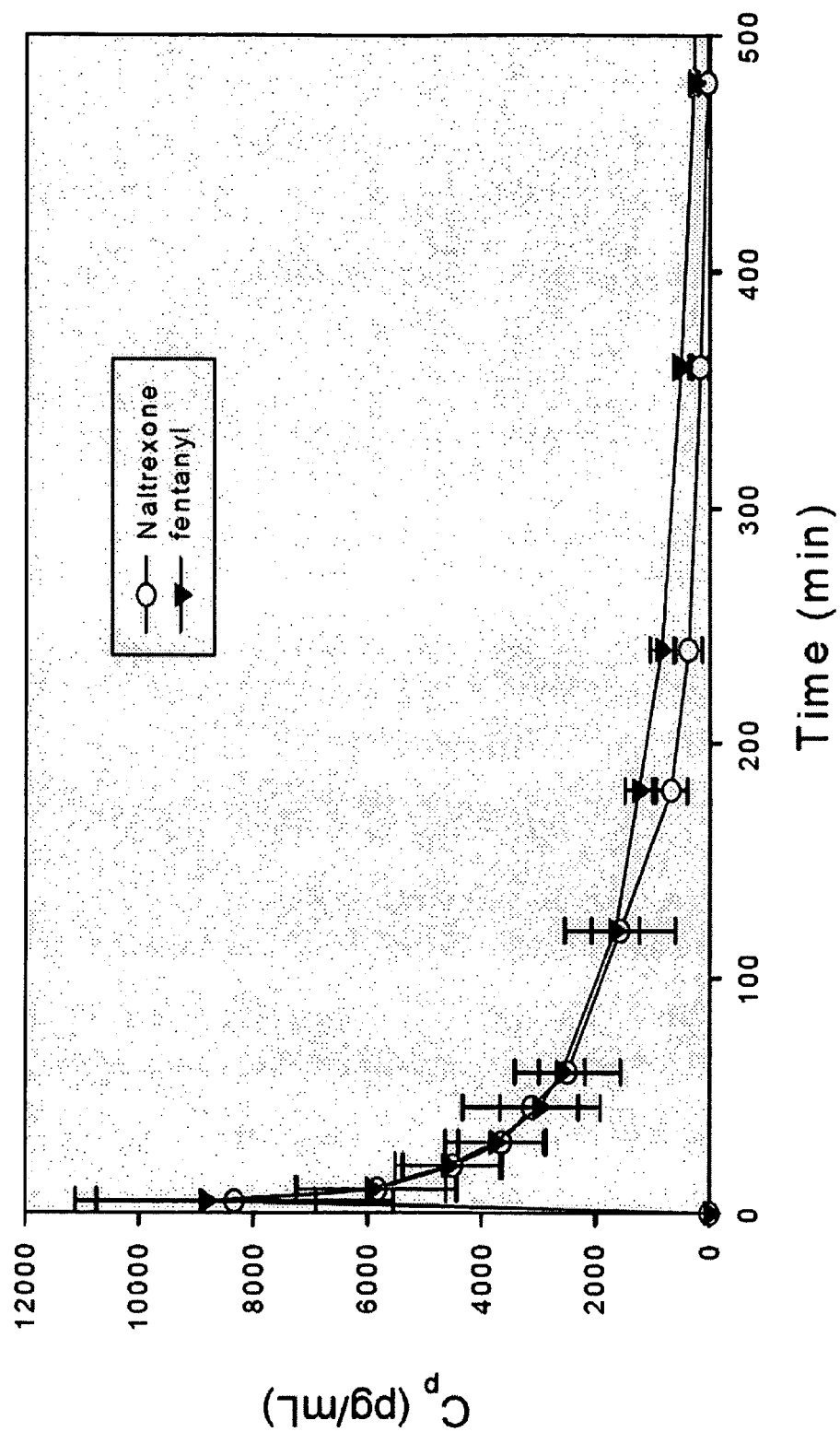
FIG. 36 shows mean plasma concentrations of fentanyl and naltrexone following the IV co-administration of 45 µg/kg of fentanyl and naltrexone to male beagle dogs.
Figure 37:
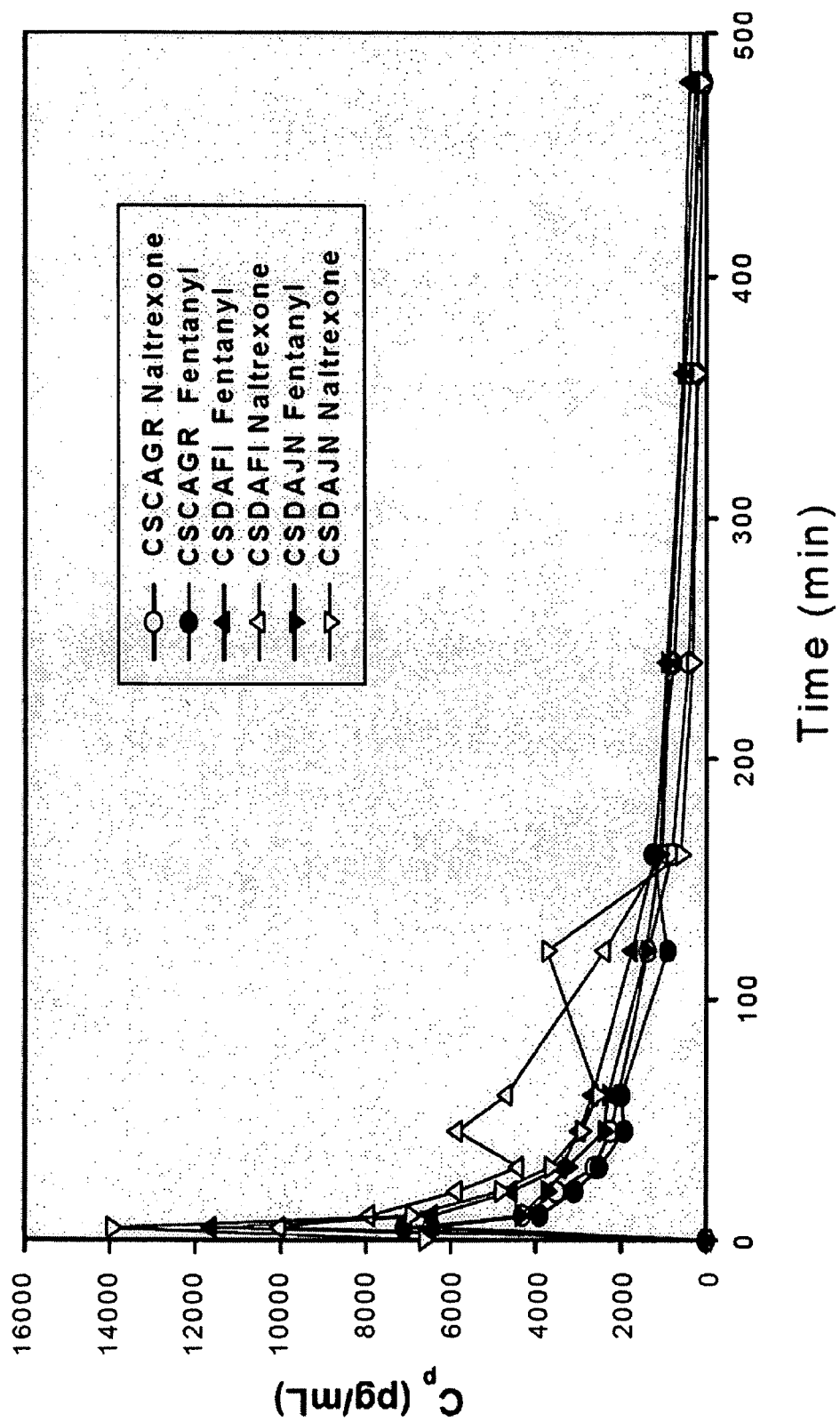
FIG. 37 shows individual plasma concentrations of fentanyl and naltrexone following the iv co-administration of 45 µg/kg of fentanyl and naltrexone to male beagle dogs.
Figure 38:
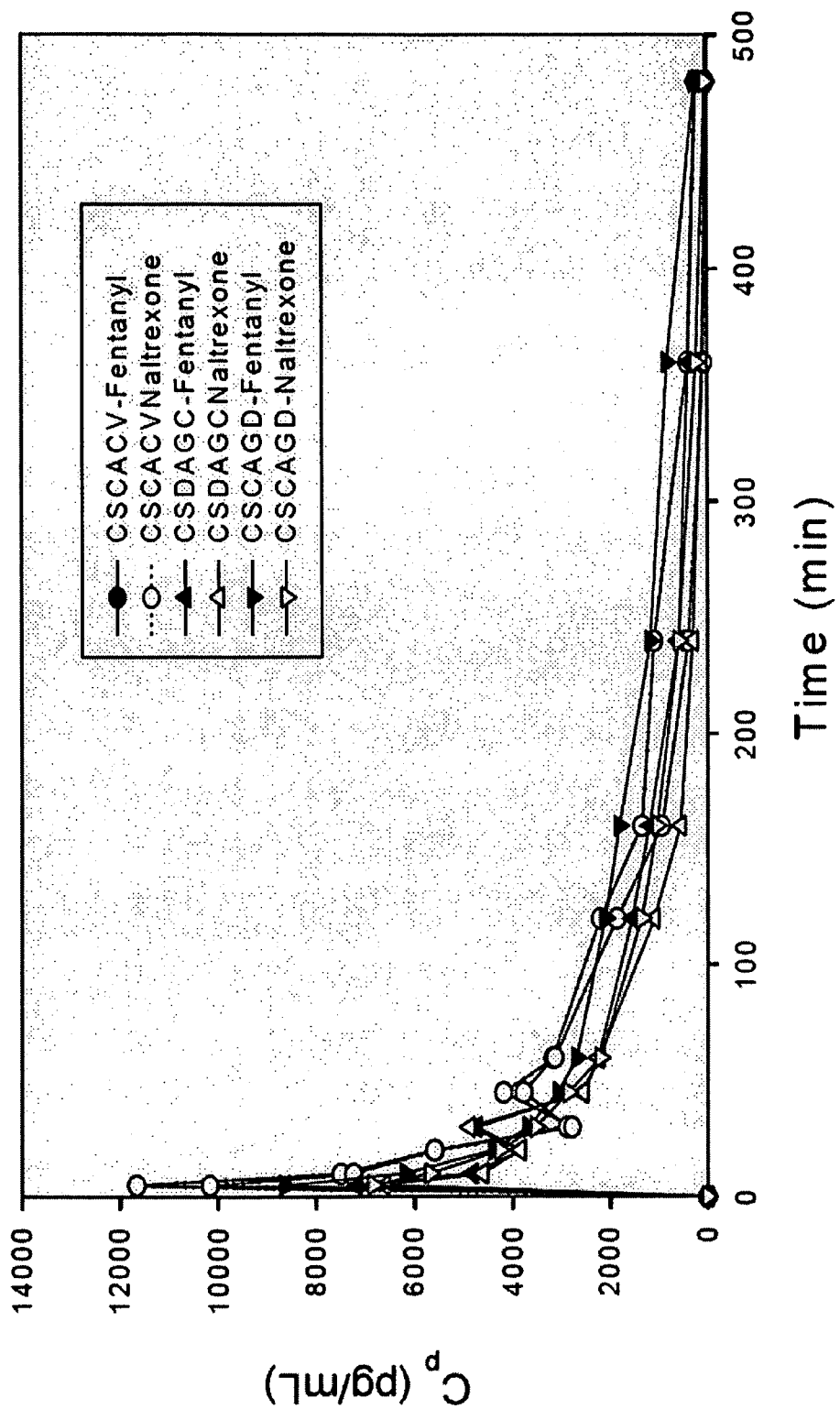
FIG. 38 shows individual plasma concentrations of fentanyl and naltrexone following the IV co-administration of 45 µg/kg of fentanyl and naltrexone to male beagle dogs.
Figure 39:
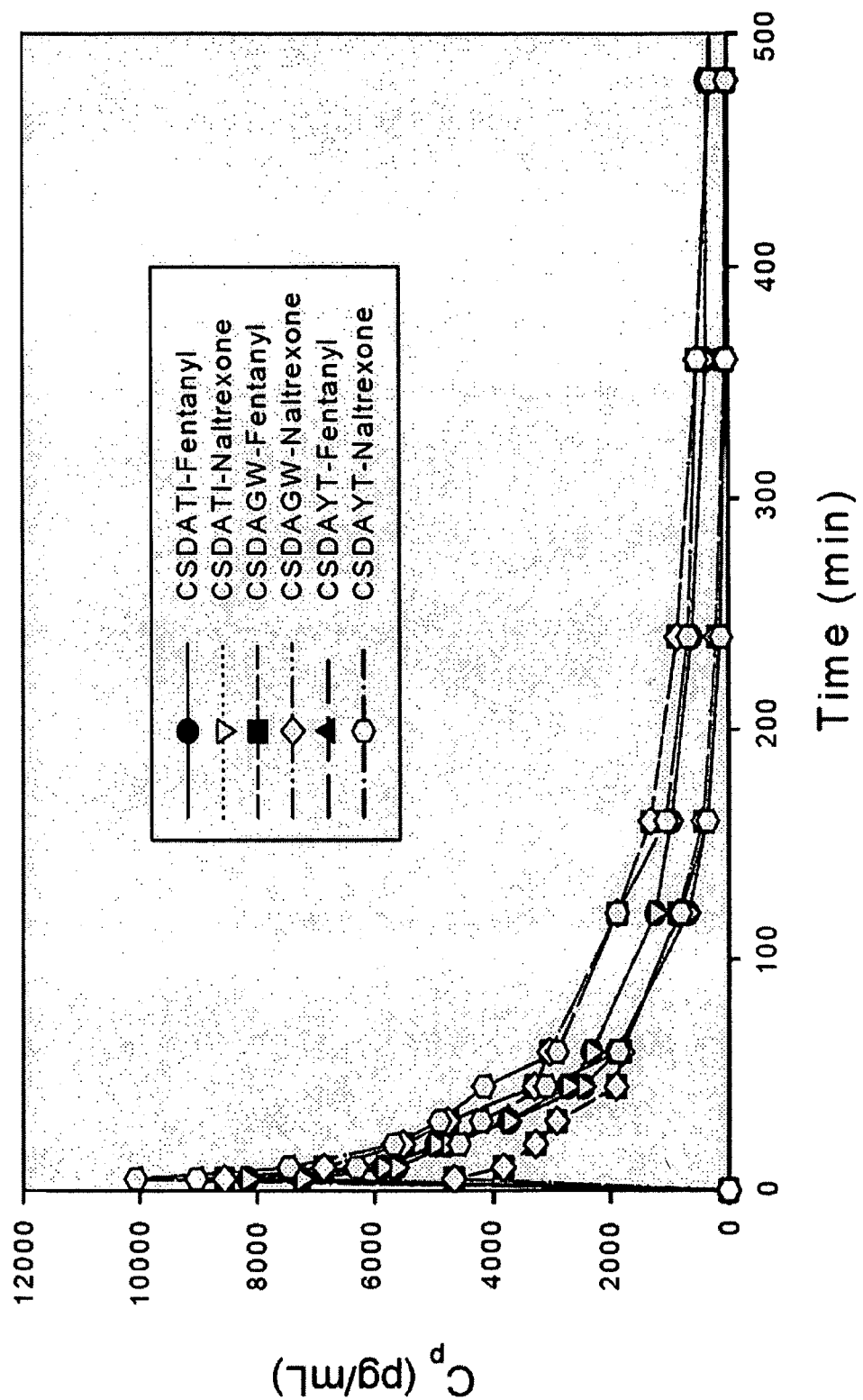
FIG. 39 shows individual plasma concentrations of fentanyl and naltrexone following the IV co-administration of 45 µg/kg of fentanyl and naltrexone to male beagle dogs.

The mean fentanyl and naltrexone plasma concentration versus time profiles following the co-administration of 45 μg/kg of the fentanyl and naltrexone are plotted in FIG. 36. The individual profiles are plotted in FIGS. 37, 38, and 39. The individual PK metrics for both fentanyl and naltrexone are listed in Table 29. The plasma concentration profiles of fentanyl were similar to the plasma profiles of naltrexone for each of the dogs. Within each dog, the PK metrics for fentanyl and naltrexone resulting from the co-administration of equal concentrations of fentanyl and naltrexone were similar for the two compounds. The fentanyl $C_{max}$ ranged from 6445 to 11655 pg/mL while the naltrexone $C_{max}$ ranged from 4658 to 113941 pg/mL. The fentanyl $AUC_{inf}$ values ranged from 8628 to 15516 pg·h/mL whereas the naltrexone $AUC_{inf}$ values were lower and ranged from 5408 to 14027 pg*h/mL. The major difference was in the $t_{1/2}$ values which were shorter for naltrexone and ranged from 0.915 to 1.31 hours as compared to 1.76 to 6.30 hours for fentanyl.

While it was possible to quantitate 6 β-naltrexol concentrations in the plasma of most of the dogs, there were only a few timepoints/dog where concentrations were above the lower LOQ (10 pg/mL).

The IV clearance of fentanyl and naltrexone was used to determine transbuccal flux from the various formulations. The only consistent flux was obtained from the Duragesic® gel. All other formulations showed variable transbuccal flux. As expected, in most cases the transbuccal flux of fentanyl mirrored the flux of naltrexone.

Figure 40:
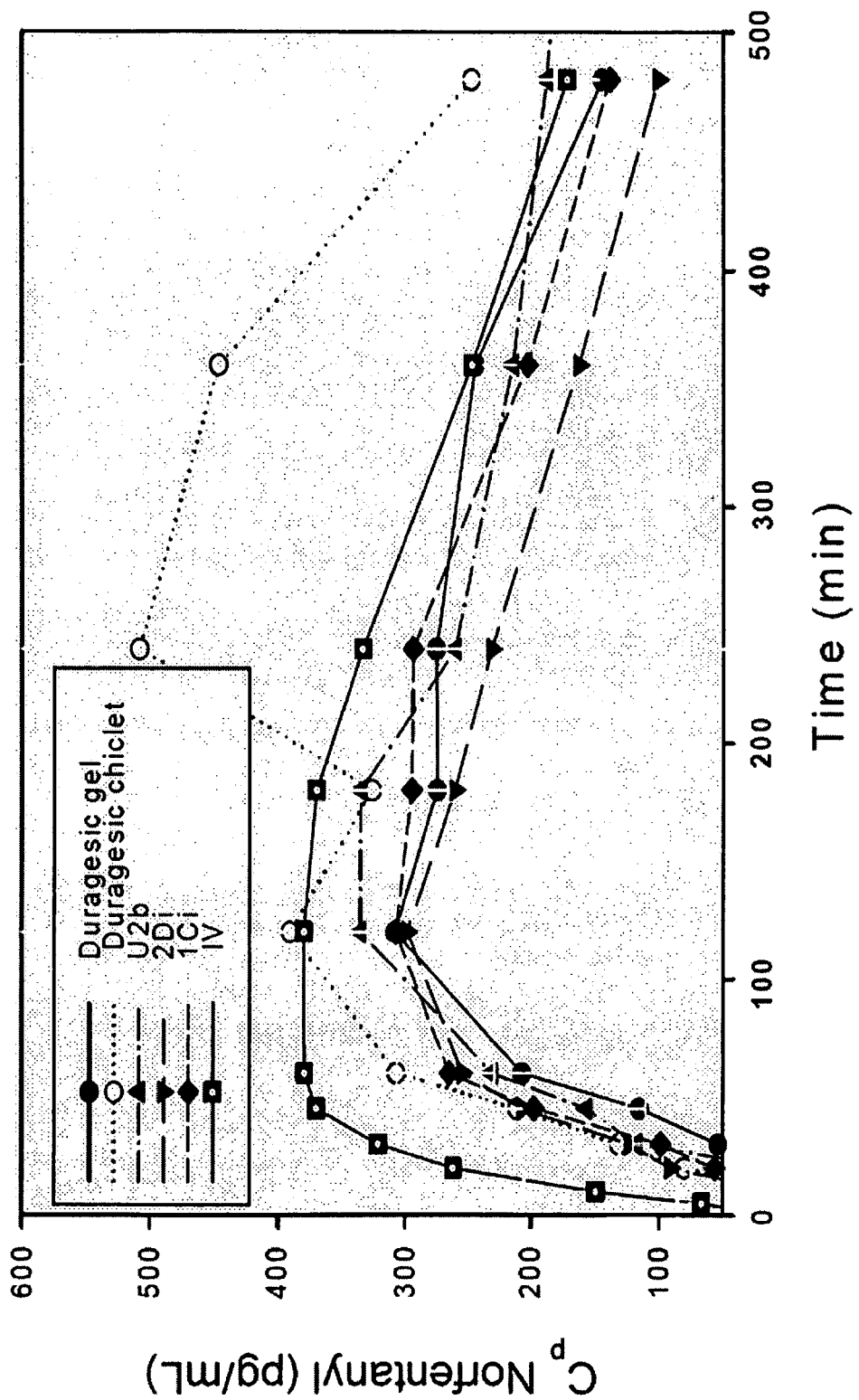
FIG. 40 shows mean plasma concentrations of norfentanyl following a single administration of fentanyl to male beagle dogs.

The plasma mean concentration of norfentanyl versus time is plotted in FIG. 40. The mean plasma concentration never exceeded 600 pg/mL. There was a lag of 20 to 30 minutes between the appearance of fentanyl and of quantifiable norfentanyl plasma concentrations for all buccal applications. Similar to and in agreement with the fentanyl plasma concentrations, there is a large standard deviation about the mean plasma concentrations for norfentanyl at most time points. The individual norfentanyl metrics are found in Tables 24 to 29 while the mean metrics based on formulation are found in Table 23.

The plasma samples were analyzed for the human metabolite of naltrexone, 6-β-naltrexol. As was expected, there were very few samples with quantifiable concentrations of this chemical since it is known that naltrexone is not significantly metabolized to this material in the dog.

Sedation of varying degrees was observed with all of the buccal applications. There was a trend between higher fentanyl plasma concentration and a greater likelihood of sedation, but this was not absolute and was not quantitative. Sedation was not observed during the IV phase of the study.

The Duragesic® gel produced a pharmacokinetic profile that was consistent across the three dogs. The variability inherent in freezing and cutting a 2 $cm^2$ chiclet from the Duragesic® patch produced an inter-dog variable pharmacokinetic profile. The chiclets also produced a mean $C_{max}$ value that was approximately three times higher than 30 μL of gel while the mean $AUC_{last}$ value was approximately twice as large from the chiclet as from the gel. The actual amount of gel within the chiclet was not determined.

The cage side observations for the co-administered fentanyl plus naltrexone validated the ability of a 1:1 ratio of naltrexone to fentanyl to block the sedative effect of fentanyl. The 1Ci and 2Di formulations were able to deliver naltrexone to the systemic circulation. The 2Di formulation was more effective at delivering the naltrexone (faster and at higher systemic concentrations) and had a slower fentanyl delivery (similar mean as the Duragesic® chiclet). This combination resulted in plasma naltrexone:fentanyl ratios as low as 1:2 from 20 to 90-minutes post application. This was also confirmed with the calculation of transbuccal flux when the calculated flux of naltrexone was greater than fentanyl for the 2Di formulation.

7. TABLES

TABLE 21

Mean PK Metrics for Fentanyl Following the Administration of Fentanyl Via Buccal Application or IV Administration in Beagle Dogs

| PK Metric | Formulation | Duragesic Gel | Duragesic Chiclet | U2b | 2Di | 1Ci | IV |
|---|---|---|---|---|---|---|---|
| $C_{max}$ | Mean | 1371 | 3095 | 6532 | 3561 | 8454 | 8828 |
| (pg/mL) | SD | 167 | 1258 | 5632 | 650 | 1250 | 1914 |
|  | CV (%) | 12.1 | 40.7 | 86.2 | 18.3 | 14.8 | 21.7 |
| $t_{max}$ (h) | Mean | 0.9 | 0.7 | 0.5 | 0.4 | 0.4 | 0.1 |
|  | SD | 0.144 | 0.20 | 0 | 0.098 | 0.0981 | 0.000 |
|  | CV (%) | 15.7 | 30.62 | 0 | 22.1 | 22.1 | 0 |
| $AUC_{last}$ | Mean | 3473 | 7923 | 9519 | 6987 | 10550 | 11579 |
| (pg-h/ | SD | 141 | 5007 | 5215 | 1296 | 1650 | 2475 |
| mL) | CV (%) | 4.05 | 63.2 | 54.8 | 18.6 | 15.6 | 21.4 |
| $t_{1/2}$ (h) | Mean | 1.7 | 2.3 | 2.8 | 1.8 | 2.1 | 2.9 |
|  | SD | 0.149 | 1.33 | 1.13 | 0.262 | 0.116 | 1.57 |
|  | CV (%) | 8.67 | 58.2 | 40.0 | 14.4 | 5.51 | 54.3 |

TABLE 22

Mean PK Metrics for Naltrexone Following the Administration of Fentanyl Via Buccal Application or IV Administration in Beagle Dogs

| PK Metric | Formulation | Duragesic Gel | Duragesic Chiclet | U2b | 2Di | 1Ci | IV |
|---|---|---|---|---|---|---|---|
| $C_{max}$ | Mean |  |  |  | 1322 | 1417 | 8330 |
| (pg/ | SD | N/A | N/A | N/A | 345 | 352 | 2773 |
| mL) | CV (%) |  |  |  | 26.1 | 24.8 | 33.3 |
| $t_{max}$ (h) | Mean |  |  |  | 0.58 | 0.53 | 0.08 |
|  | SD | N/A | N/A | N/A | 0.144 | 0.210 | 0.000 |
|  | CV (%) |  |  |  | 24.7 | 39.8 | 0 |
| $AUC_{last}$ | Mean |  |  |  | 2499 | 1496 | 8605 |
| (pg-h/ | SD | N/A | N/A | N/A | 694 | 339 | 2881 |
| mL) | CV (%) |  |  |  | 27.8 | 22.7 | 33.5 |
| $t_{1/2}$ (h) | Mean |  |  |  | 0.9 | 0.9 | 1.1 |
|  | SD | N/A | N/A | N/A | 0.212 | 0.0367 | 0.147 |
|  | CV (%) |  |  |  | 23.1 | 3.9 | 13.2 |

TABLE 23

Mean PK Metrics for Norfentanyl Following the Administration of Fentanyl Via Buccal Application or IV Administration in Beagle Dogs

| PK Metric | Fentanyl source | Duragesic ® gel | Duragesic ® chiclet | U2b | 2Di | 1Ci | IV |
|---|---|---|---|---|---|---|---|
| $C_{max}$ (pg/mL) | Mean | 311 | 636 | 343 | 304 | 309 | 417 |
| | SD | 121 | 591 | 184 | 69.0 | 51.0 | 139 |
| | CV (%) | 38.9 | 92.9 | 53.6 | 22.6 | 16.5 | 33.3 |
| $t_{max}$ (h) | Mean | 2.3 | 3.2 | 2.7 | 1.7 | 3.0 | 1.5 |
| | SD | 0.577 | 1.83 | 0.577 | 0.577 | 1.00 | 0.814 |
| | CV (%) | 24.7 | 57.9 | 21.7 | 34.6 | 33.3 | 55.3 |
| $AUC_{last}$ (pg-h/mL) | Mean | 1814 | 2905 | 2761 | 1587 | 4450 | 2379 |
| | SD | 683 | 2112 | 1836 | 332 | 692 | 714 |
| | CV (%) | 37.6 | 72.7 | 66.5 | 20.9 | 15.5 | 30.0 |
| $t_{1/2}$ (h) | Mean | 3.14[1] | 3.48 | 6.12 | 3.54 | 20.8 | 4.36 |
| | SD | NA | 1.17 | 1.92 | 0.885 | NC | 1.80 |
| | CV (%) | NA | 33.5 | 31.3 | 25.0 | NC | 41.2 |

[1])only able to accurately calculate for one dog.

TABLE 24

Individual PK Metrics for Beagle Dogs Following the Application of 30 µL (approximately 0.9 mg fentanyl) Duragesic ® Gel to the Buccal Mucosa

| PK Metric | Drug Substance | CSUAFI | CSCAGR | CSDATI |
|---|---|---|---|---|
| $C_{max}$ (pg/mL) | Fentanyl | 1206 | 1367 | 1539 |
| | Norfentanyl | 289 | 202 | 441 |
| $t_{max}$ (h) | Fentanyl | 1.00 | 0.75 | 1.00 |
| | Norfentanyl | 2.00 | 3.00 | 2.00 |
| $AUC_{inf}$ (pg-h/mL) | Fentanyl | 3683 | 3555 | 3763 |
| | Norfentanyl | 1665 | 1218 | 2558 |
| $t_{1/2}$ (h) | Fentanyl | 1.76 | 1.85 | 1.56 |
| | Norfentanyl | NC | NC | 3.14 |
| Buccal flux ($\mu g/cm^2$-h) | Fentanyl | 10.9 | 18.5 | 15.9 |

*Since $t_{1/2}$ could not be calculated for norfentanyl in many of the dogs, $AUC_{last}$ was used.

TABLE 25

Individual PK Metrics for Beagle Dogs Following the Application of a 2 $cm^2$ Duragesic ® Chiclet to the Buccal Mucosa

| PK Metric | Drug Substance | CSCACV | CSDAGC | CSCAGD | CSDAGW | CSDAJN | CSDAYT |
|---|---|---|---|---|---|---|---|
| $C_{max}$ (pg/mL) | Fentanyl | 3377 | 5031 | 2666 | 2409 | 3729 | 1355 |
| | Norfentanyl | 346 | 435 | 211 | 901 | 1722 | 201 |
| $t_{max}$ (h) | Fentanyl | 0.75 | 0.50 | 0.50 | 0.75 | 1.00 | 0.50 |
| | Norfentanyl | 4.00 | 2.00 | 2.00 | 6.00 | 4.00 | 1.00 |
| $AUC_{inf}$ (pg-h/mL)* | Fentanyl | 5958 | 16683 | 5092 | 6162 | 12572 | 3175 |
| | Norfentanyl | 1985 | 2359 | 1342 | 3592 | 6860 | 1293 |
| $t_{1/2}$ (h) | Fentanyl | 1.53 | 4.97 | 1.64 | 1.52 | 2.09 | 1.99 |
| | Norfentanyl | 3.29 | NC | NC | NC | 2.42 | 4.73 |
| Buccal flux ($\mu g/cm^2$-h) | Fentanyl | 20.35 | 73.41 | 16.64 | 20.93 | 53.84 | 9.21 |

*Since $t_{1/2}$ could not be calculated for norfentanyl in many of the dogs, $AUC_{last}$ was used.

TABLE 26

Individual PK Metrics for Beagle Dogs Following the Application of a 2 $cm^2$ U2b (3M formulation) Transdermal Patch to the Buccal Mucosa

| PK Metric | Drug Substance | CSDAGC | CSDAGW | CSDAJN |
|---|---|---|---|---|
| $C_{max}$ (pg/mL) | Fentanyl | 2204 | 12900 | 4492 |
| | Norfentanyl | 158 | 526 | 346 |
| $t_{max}$ (h) | Fentanyl | 0.50 | 0.50 | 0.50 |
| | Norfentanyl | 3.00 | 2.00 | 3.00 |
| $AUC_{inf}$ (pg-h/mL) | Fentanyl | 4337 | 15719 | 13207 |
| | Norfentanyl | 2085 | 3714 | 5200 |
| $t_{1/2}$ (h) | Fentanyl | 2.05 | 2.29 | 4.11 |
| | Norfentanyl | 7.60 | 3.96 | 6.80 |
| Buccal flux ($\mu g/cm^2$-h) | Fentanyl | 19.1 | 53.4 | 56.6 |

TABLE 27

Individual PK Metrics for Beagle Dogs Following the Application of a 2 $cm^2$ 2Di (3M formulation) Transdermal Patch to the Buccal Mucosa

| PK Metric | Drug Substance | Tatoo CSCACN | Tatoo CSDAFI | Tatoo CSCAGR |
|---|---|---|---|---|
| $C_{max}$ (pg/mL) | Fentanyl | 3567 | 2908 | 4208 |
| | Norfentanyl | 349 | 225 | 338 |
| | Naltrexone | 1651 | 963 | 1353 |

TABLE 27-continued

Individual PK Metrics for Beagle Dogs Following the Application of a 2 cm² 2Di (3M formulation) Transdermal Patch to the Buccal Mucosa

| PK Metric | Drug Substance | Tatoo CSCACN | Tatoo CSDAFI | Tatoo CSCAGR |
|---|---|---|---|---|
| $t_{max}$ (h) | Fentanyl | 0.50 | 0.50 | 0.33 |
| | Norfentanyl | 2.00 | 1.00 | 2.00 |
| | Naltrexone | 0.50 | 0.75 | 0.50 |
| $AUC_{inf}$ (pg-h/mL) | Fentanyl | 7279 | 5948 | 8890 |
| | Norfentanyl | 2303 | 1785 | 2187 |
| | Naltrexone | 3139 | 1764 | 2656 |
| $t_{1/2}$ (h) | Fentanyl | 1.57 | 1.78 | 2.09 |
| | Norfentanyl | 3.12 | 4.56 | 2.95 |
| | Naltrexone | 0.785 | 0.804 | 1.16 |
| Buccal flux ($\mu g/cm^2$-h) | Fentanyl | 24.9 | 17.6 | 46.4 |
| | Naltrexone | 57.3 | 22.6 | 64.1 |

TABLE 28

Individual PK Metrics for Beagle Dogs Following the Application of a 2 cm² 1Ci (3M formulation) Transdermal Patch to the Buccal Mucosa

| PK Metric | Drug Substance | Tatoo CSDAGD | Tatoo CSDATI | Tatoo CSDAYT |
|---|---|---|---|---|
| $C_{max}$ (pg/mL) | Fentanyl | 7369 | 8173 | 9821 |
| | Norfentanyl | 335 | 341 | 250 |
| | Naltrexone | 1011 | 1637 | 1602 |
| $t_{max}$ (h) | Fentanyl | 0.50 | 0.33 | 0.50 |
| | Norfentanyl | 4.00 | 3.00 | 2.00 |
| | Naltrexone | 0.75 | 0.33 | 0.50 |
| $AUC_{inf}$ (pg-h/mL) | Fentanyl | 10579 | 9926 | 13168 |
| | Norfentanyl* | 4822 | 4875 | 3652 |
| | Naltrexone | 1709 | 1724 | 1121 |
| $t_{1/2}$ (h) | Fentanyl | 2.24 | 2.01 | 2.09 |
| | Norfentanyl | NC | 20.9 | 20.7 |
| | Naltrexone | 0.986 | 0.912 | 0.950 |
| Buccal flux ($\mu g/cm^2$-h) | Fentanyl | 34.6 | 41.9 | 38.2 |
| | Naltrexone | 35.6 | 51.1 | 30.5 |

*Since $t_{1/2}$ could not be calculated for norfentanyl in one of the dogs and the other 2 had r² values just above 0.85, the $AUC_{last}$ is listed.

TABLE 29

Individual PK Metrics Following the IV administration of 45 μg of Fentanyl and Naltrexone to Male Beagle Dogs

| PK Metric | Drug Substance | CSCAGR | CSDAFI | CSDAJN | CSCACV | CSDAGC | CSCAGD | CSDATI | CSDAGW | CSDAYT |
|---|---|---|---|---|---|---|---|---|---|---|
| $C_{max}$ (pg/mL) | Fentanyl | 7096 | 11629 | 6445 | 11655 | 7184 | 8638 | 8166 | 8564 | 10072 |
| | Norfentanyl | 514 | 293 | 593 | 657 | 341 | 378 | 339 | 387 | 254 |
| | Naltrexone | 6460 | 10026 | 13941 | 10159 | 6610 | 6853 | 7228 | 4658 | 9036 |
| $t_{max}$ (h) | Fentanyl | 0.08 | 0.08 | 0.08 | 0.08 | 0.08 | 0.08 | 0.08 | 0.08 | 0.08 |
| | Norfentanyl | 0.5 | 2.0 | 2.0 | 0.8 | 1.0 | 3.0 | 2.0 | 1.0 | 1.0 |
| | Naltrexone | 0.08 | 0.08 | 0.08 | 0.08 | 0.08 | 0.08 | 0.08 | 0.08 | 0.08 |
| $AUC_{inf}$ (pg-h/mL) | Fentanyl | 8628 | 15211 | 10508 | 13176 | 10227 | 13767 | 10655 | 13252 | 15516 |
| | Norfentanyl | 3511 | 4418 | 5329 | 4161 | 2639 | 3505 | 2577 | 2662 | NC |
| | Naltrexone | 7458 | 14027 | 12236 | 9869 | 7540 | 8648 | 6078 | 5408 | 6623 |
| $t_{1/2}$ (h) | Fentanyl | 1.85 | 4.83 | 2.17 | 1.76 | 2.06 | 2.14 | 2.38 | 2.61 | 6.30 |
| | Norfentanyl | 4.1 | 8.5 | 4.2 | 3.0 | 3.9 | 4.7 | 4.0 | 2.5 | NC |
| | Naltrexone | 1.31 | 1.25 | 1.24 | 0.992 | 1.10 | 1.20 | 0.946 | 1.04 | 0.915 |
| Clearance (mL/h) | Fentanyl | 5216 | 2958 | 4283 | 3415 | 4400 | 3269 | 4224 | 3396 | 2900 |
| | Naltrexone | 6034 | 3208 | 3678 | 4560 | 5969 | 5204 | 7404 | 8322 | 6794 |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

All publications, patents and patent applications mentioned in this specification are herein incorporated by reference in their entirety into the specification to the same extent as if each individual publication, patent or patent application was specifically and individually indicated to be incorporated herein by reference in their entirety for all purposes.

What is claimed is:

1. A transdermal dosage form comprising:
   an active agent component having a proximal, skin contacting surface and a distal surface and comprising an opioid agonist;
   an adverse agent component having a proximal surface and a distal surface and comprising an opioid antagonist;
   a backing;
   a barrier having a proximal surface and a distal surface that is interposed between the active agent component and the adverse agent component, wherein one or more channels extend completely from the proximal surface of the active agent component to the distal surface of the barrier and terminate prior to the proximal surface of the adverse agent component;
   wherein air is disposed in one or more channels;
   and wherein the barrier is permeable to a solvent selected from the group consisting of water, ethanol, ether, and mixtures thereof, and wherein the barrier is impermeable to diffusion of opioid agonist and opioid antagonist in the absence of said solvent.

2. A transdermal dosage form of claim 1, wherein the active agent component further comprises a polymeric material and the opioid agonist is dispersed in the polymeric material.

3. A transdermal dosage form according to claim 2, wherein the opioid agonist is homogeneously dispersed in the polymeric material.

4. A transdermal dosage form according to claim 1, further comprising an adhesive component connecting the adverse agent component and the barrier.

5. A transdermal dosage form according to claim 1, wherein the adverse agent component is interposed between the barrier and a portion of the backing.

6. A transdermal dosage form according to claim 5, wherein the backing is a continuous, polymeric film.

7. A transdermal dosage form according to claim 5, wherein the backing is an overlay backing.

8. A transdermal dosage form according to claim 1, wherein the adverse agent component comprises a pressure-sensitive adhesive and the opioid antagonist is dispersed in the pressure-sensitive adhesive.

9. A transdermal dosage form according to claim 8, wherein the pressure-sensitive adhesive comprises an acrylate pressure-sensitive adhesive.

10. A transdermal dosage form according to claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, a pharmaceutically acceptable salt thereof, and mixtures of two or more of the foregoing.

11. A transdermal dosage form according to claim 1, wherein the opioid antagonist is selected from the group consisting of naloxone, naltrexone, nalmefene, nalbuphine, nalorphine, cyclazacine, cyclazocine, levallorphan, a pharmaceutically acceptable salt thereof, and mixtures of two or more of the foregoing.

12. A transdermal dosage form according to claim 1, wherein the opioid agonist is fentanyl or a pharmaceutically acceptable salt thereof.

13. A transdermal dosage form according to claim 1, wherein the opioid antagonist is naltrexone or a pharmaceutically acceptable salt thereof.

14. A transdermal dosage form according to claim 13, wherein the opioid agonist is fentanyl or a pharmaceutically acceptable salt thereof.

15. A method of transdermal delivery of an active agent from a tamper-resistant dosage form comprising: (a) providing a transdermal dosage form according to claim 1; and (b) applying the dosage form to a portion of the skin or mucosa of a patient for a period sufficient to achieve the desired therapeutic result.

16. A transdermal dosage form according to claim 1, wherein said transdermal dosage form can deliver, when tampered with, a ratio of opioid antagonist to opioid agonist of about 1 to about 10 to a ratio of about 1 to about 1.

17. A transdermal dosage form according to claim 16, wherein said opioid agonist is fentanyl and said opioid antagonist is naltrexone.

18. A transdermal dosage form according to claim 2, wherein the opioid antagonist is an antagonist to the opioid agonist.

19. A transdermal dosage form according to claim 1, wherein the barrier is at least partially soluble in a solvent selected from the group consisting of water, ethanol, ether, and mixtures thereof.

20. A transdermal dosage form according to claim 1, wherein the barrier is permeable to water, ethanol, and mixtures thereof.

* * * * *